(12) United States Patent
Kim et al.

(10) Patent No.: US 10,966,675 B2
(45) Date of Patent: Apr. 6, 2021

(54) MEDICAL IMAGING APPARATUS AND METHOD OF OPERATING SAME

(71) Applicant: SAMSUNG ELECTRONICS CO., LTD., Suwon-si (KR)

(72) Inventors: Seung-hoon Kim, Suwon-si (KR); Si-won Park, Suwon-si (KR); Se-hui Kim, Anyang-si (KR); Do-hyeong Hwang, Gunpo-si (KR); Sung-jin Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 499 days.

(21) Appl. No.: 15/722,554

(22) Filed: Oct. 2, 2017

(65) Prior Publication Data
US 2018/0035959 A1  Feb. 8, 2018

Related U.S. Application Data

(63) Continuation of application No. 14/838,870, filed on Aug. 28, 2015, now Pat. No. 9,814,435.

(30) Foreign Application Priority Data

Aug. 28, 2014  (KR) .................. 10-2014-0113349
Aug. 12, 2015  (KR) .................. 10-2015-0113857

(51) Int. Cl.
*A61B 6/00* (2006.01)
*A61B 6/06* (2006.01)

(52) U.S. Cl.
CPC .............. *A61B 6/469* (2013.01); *A61B 6/465* (2013.01); *A61B 6/467* (2013.01); *A61B 6/5241* (2013.01);
(Continued)

(58) Field of Classification Search
CPC .......... A61B 6/06; A61B 6/463; A61B 6/465; A61B 6/469; A61B 6/467; A61B 6/5241; A61B 6/4233; A61B 6/542
See application file for complete search history.

(56) References Cited

U.S. PATENT DOCUMENTS 8,396,184 B2   3/2013  Shinno
2005/0169425 A1*  8/2005  Takasawa .............. A61B 6/547
                                              378/97
(Continued)

FOREIGN PATENT DOCUMENTS

CN  103505229 A  1/2014
CN  103906471 A  7/2014
(Continued)

OTHER PUBLICATIONS

Communication dated Dec. 7, 2015, issued by the International Searching Authority in counterpart International Application No. PCT/KR2015/009049 (PCT/ISA/220, PCT/ISA/210, PCT/ISA/237).

(Continued)

*Primary Examiner* — Chih-Cheng Kao
(74) *Attorney, Agent, or Firm* — Sughrue Mion, PLLC

(57) ABSTRACT

A medical imaging apparatus is provided. The medical image apparatus includes an output unit; and a controller configured to control the output unit to display an image obtained by photographing an object and to display, over the image, a top indicator for setting a top limit for an area to be X-rayed and at least one guideline indicating a bottom limit for the area to be X-rayed according to the top indicator and the number of partial photographing operations.

24 Claims, 55 Drawing Sheets

(52) U.S. Cl.
CPC .............. *A61B 6/06* (2013.01); *A61B 6/4233* (2013.01); *A61B 6/542* (2013.01)

(56) References Cited

U.S. PATENT DOCUMENTS

| | | |
|---|---|---|
| 2005/0169427 A1 | 8/2005 | Halsmer et al. |
| 2007/0242806 A1 | 10/2007 | Borgmann et al. |
| 2009/0060125 A1* | 3/2009 | Tsuyuki .................. A61B 6/032 378/19 |
| 2011/0249791 A1* | 10/2011 | Wang ....................... A61B 6/08 378/62 |
| 2011/0249792 A1 | 10/2011 | Lalena et al. |
| 2011/0249799 A1 | 10/2011 | Lalena et al. |
| 2012/0128125 A1 | 5/2012 | Jabri et al. |
| 2012/0163539 A1* | 6/2012 | van der Veen ....... A61N 5/1049 378/65 |
| 2012/0183126 A1* | 7/2012 | Cho ......................... A61B 6/06 378/150 |
| 2013/0022172 A1* | 1/2013 | Lee ......................... A61B 6/463 378/63 |
| 2013/0077745 A1 | 3/2013 | Wang et al. |
| 2013/0294569 A1 | 11/2013 | Yoshikawa et al. |
| 2013/0343523 A1 | 12/2013 | Lee et al. |
| 2014/0037057 A1 | 2/2014 | Kim |
| 2014/0056408 A1 | 2/2014 | Tajima |
| 2014/0169521 A1 | 6/2014 | Nakanishi et al. |

FOREIGN PATENT DOCUMENTS

| | | |
|---|---|---|
| JP | 2011-125486 A | 6/2011 |
| JP | 2012-147978 A | 8/2012 |
| JP | 2013-039197 A | 2/2013 |
| KR | 10-2013-0059489 A | 6/2013 |
| KR | 10-2013-0142850 A | 12/2013 |
| WO | 2013154167 A1 | 10/2013 |

OTHER PUBLICATIONS

Communication dated Jul. 19, 2017 issued by the European Patent Office in counterpart Application No. 15835969.5.
Communication dated Nov. 28, 2019, from the State Intellectual Property Office of People's Republic of China in counterpart Application No. 201580059303.3.
Communication dated Jun. 24, 2020 by the European patent Office in counterpart European patent Application No. 19215788.1.
Communication dated Sep. 1, 2020 by the State Intellectual Property Office of P.R. China in counterpart Chinese Patent Application No. 201580059303.3.

* cited by examiner

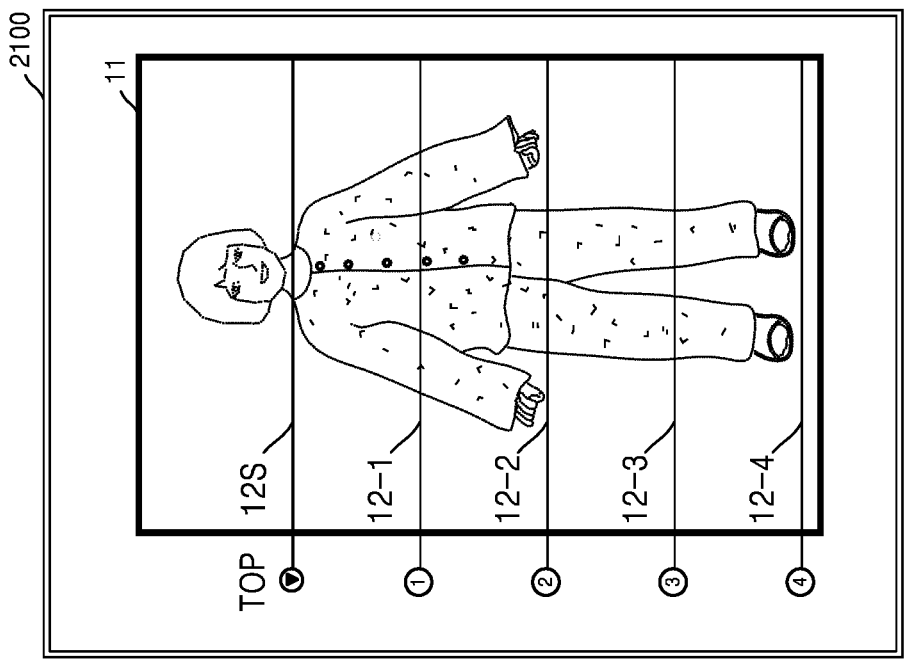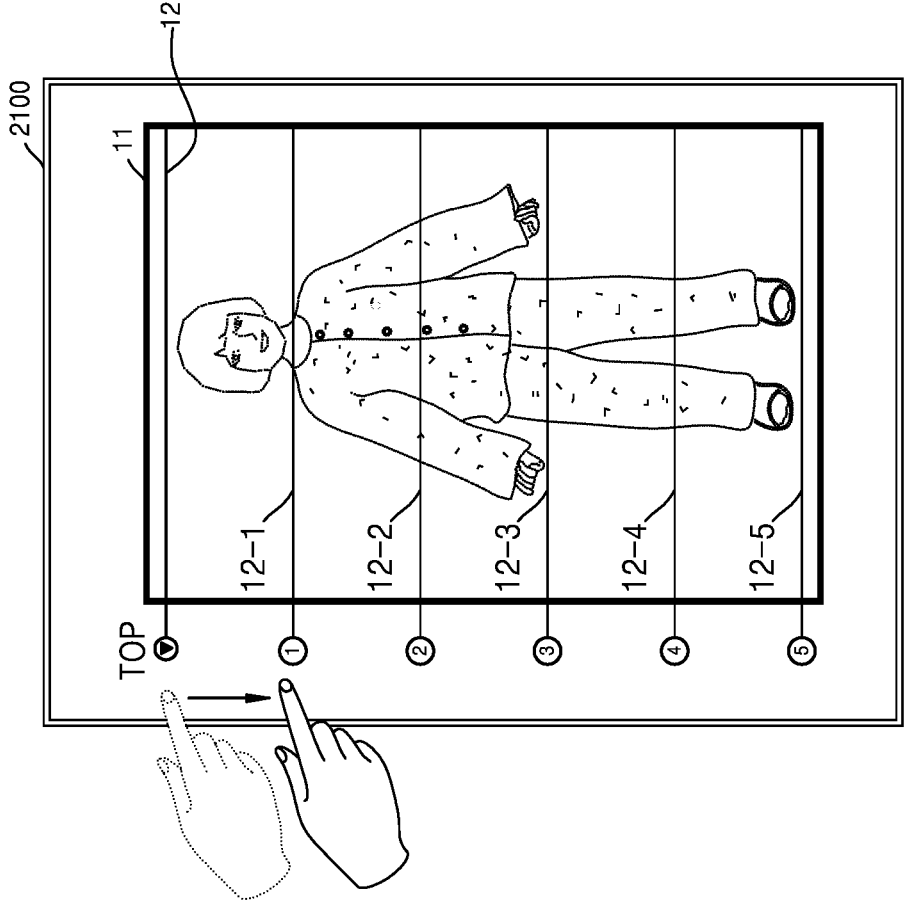

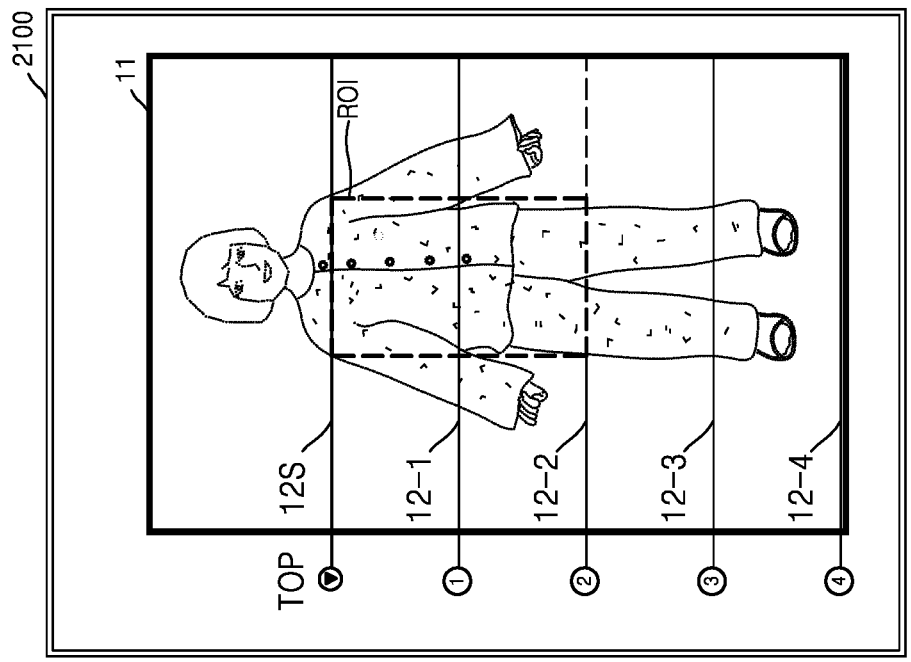
FIG. 11A
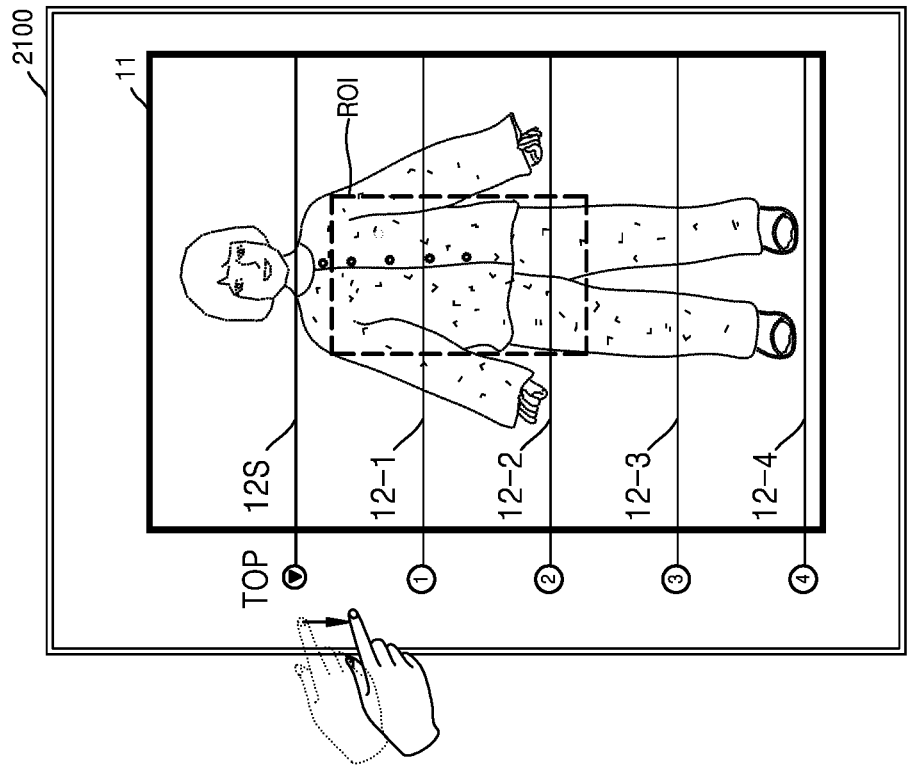
FIG. 11B

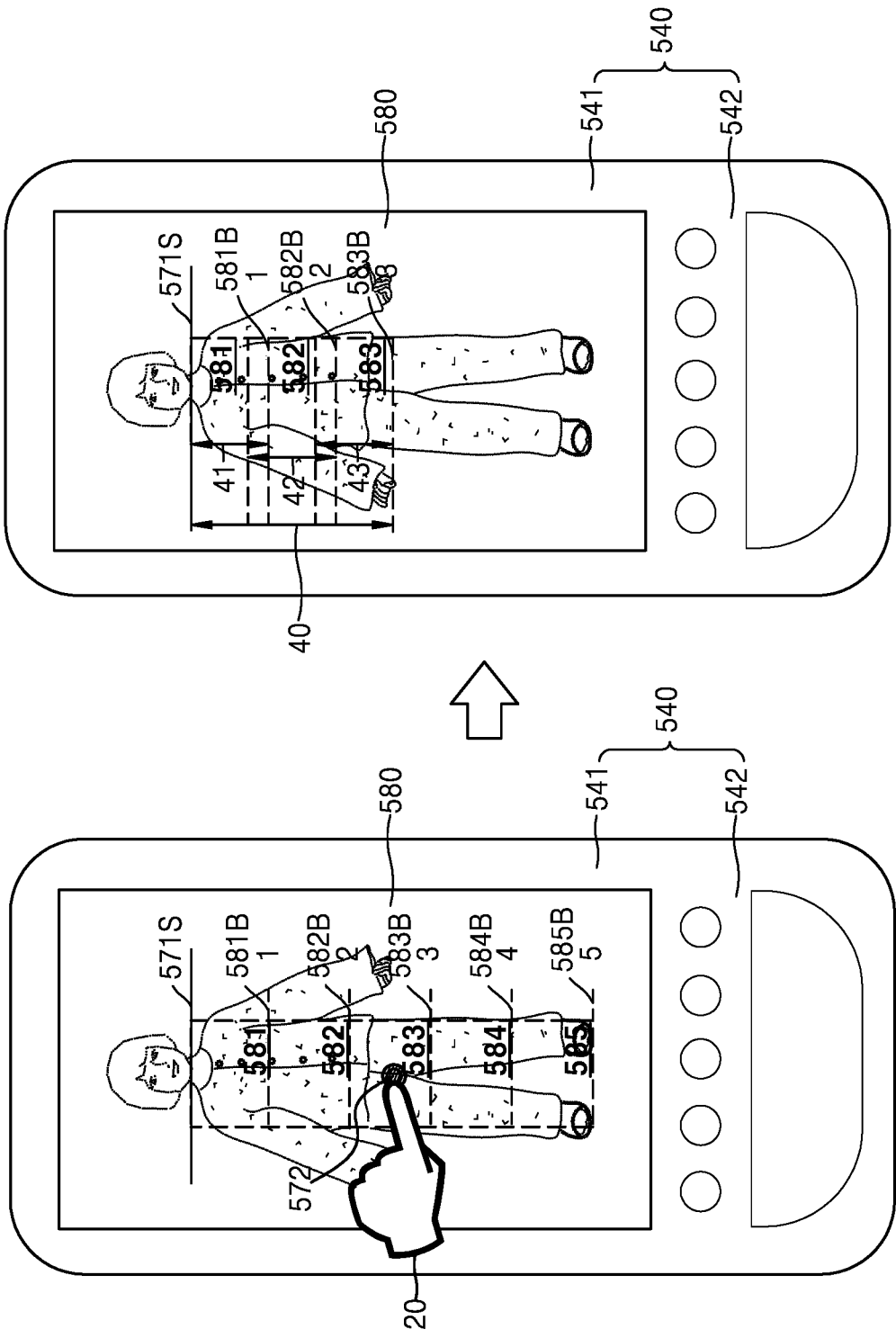

MEDICAL IMAGING APPARATUS AND METHOD OF OPERATING SAME

CROSS-REFERENCE TO RELATED APPLICATIONS

This a continuation of U.S. application Ser. No. 14/838,870 filed Aug. 28, 2015, which claims priority from Korean Patent Application No. 10-2014-0113349, filed on Aug. 28, 2014, and Korean Patent Application No. 10-2015-0113857, filed on Aug. 12, 2015, in the Korean Intellectual Property Office, the disclosures of which are incorporated herein by reference in their respective entireties.

BACKGROUND

1. Field

Exemplary embodiments relate to medical imaging apparatuses and methods of operating the same, and more particularly, to medical imaging apparatuses and methods of operating the same which are capable of preventing excessive X-ray irradiation.

2. Description of the Related Art

Medical imaging apparatuses are used to acquire medical images showing an internal structure of an object. The medical imaging apparatuses are non-invasive examination devices that capture and process images of details of structures, tissue, fluid flow, etc., inside a body, and then provide the images to a user. A user, e.g., a medical practitioner, may use medical images output from the medical imaging apparatuses to diagnose a patient's condition and diseases.

A representative example of such medical imaging apparatuses is an X-ray apparatus. X-rays are a form of electromagnetic radiation having wavelengths of between 0.01 angstroms (Å) and 100 angstroms, and may be widely used in medical apparatuses for imaging the inside of a living body or in non-destructive testing equipment for industrial use due to their ability to penetrate objects.

An X-ray apparatus may acquire X-ray images of an object by transmitting X-rays emitted from an X-ray source through an object and detecting a difference in intensities of the transmitted X-rays via an X-ray detector. The X-ray images may be used to examine an internal structure of an object and to diagnose the object with a disease. The X-ray apparatus facilitates easy observation of an internal structure of an object by using a principle in which a penetrating power of an X-ray varies based on the density of the object and atomic numbers of atoms constituting the object. As a wavelength of an X-ray decreases, the penetrating power of the X-ray increases and the X-ray images become brighter.

SUMMARY

Provided are medical imaging apparatuses and methods of operating the same which are capable of preventing excessive X-ray irradiation.

Additional aspects will be set forth in part in the description which follows and, in part, will be apparent from the description, or may be learned by practice of the presented exemplary embodiments.

In an aspect of one or more exemplary embodiments, a medical imaging apparatus includes an output device and a controller. The controller is configured to control the output device to display an image obtained by photographing an object and to display, over the image, a top indicator that relates to setting a top limit for an area to be X-rayed and at least one guideline that indicates a bottom limit for the area to be X-rayed based on the top indicator and a number of partial photographing operations.

The medical imaging apparatus may further include an input device configured to receive a user input that relates to adjusting a position of the top indicator on the image. The output device may be configured to display at least one guideline that is changed based on the adjusted position of the top indicator.

The input device may be further configured to receive a user input that relates to setting a bottom limit for the area to be X-rayed.

The controller may be further configured to determine the number of partial photographing operations based on the bottom limit and to partition an area between the top indicator and the bottom limit in the image into regions for the partial photographing operations based on the determined number of partial photographing operations. The output device may be further configured to display the regions of the partial photographing operations on the image.

The output device may be further configured to highlight overlapping portions between the regions for the partial photographing operations.

The output device may be further configured to display a bottom indicator that relates to setting the bottom limit for the area to be X-rayed. The received user input that relates to setting the bottom limit for the area to be X-rayed may be used for adjusting a position of the bottom indicator.

The controller may be further configured to determine the number of partial photographing operations to be performed on an area between the top and bottom indicators, to partition the area between the top and bottom indicators in the image into equally sized regions based on the determined number of partial photographing operations, and to control the output device to display at least one guideline that indicates a respective bottom limit for each of the regions.

When the input device receives a user input that relates to adjusting a position of at least one of the top and bottom indicators, the controller may be further configured to redetermine the number of partial photographing operations based on the adjusted position of the at least one of the top and bottom indicators, to repartition an area between the top and bottom indicators into equally sized regions based on the redetermined number of partial photographing operations, and to control the output device to redisplay the changed at least one guideline that indicates the bottom limit for each of the regions.

The output device may be further configured to display a plurality of automatic exposure control (AEC) markers in each of the regions for the partial photographing operations displayed on the image, such that each respective one of the plurality of AEC markers indicates a corresponding one of a plurality of AEC chambers included in an X-ray detector during a partial photographing operation with respect to each of the regions for the partial photographing operations.

The controller may be further configured set an on/off state of each of the AEC markers and to turn on or off each respective AEC chamber in the X-ray detector based on the set on/off state of each corresponding one of the AEC markers during a partial photographing operation.

The input device may be further configured to receive a user input that relates to setting an on/off state of an AEC marker selected from among the AEC markers displayed on the image.

The controller may be further configured to detect, from among the AEC markers displayed on the image, an AEC chamber which is located outside the object, and to turn off the detected AEC chamber.

The medical imaging apparatus may further include an image acquirer configured to acquire the image by photographing the object.

The medical imaging apparatus may further include an X-ray radiator configured to radiate an X-ray. The controller may be further configured to determine the number of partial photographing operations based on the bottom limit, to partition an area between the top indicator and the bottom limit in the image into regions for the partial photographing operations based on the determined number of partial photographing operations, and to control the X-ray radiator to perform the partial photographing operations on the regions.

The controller may be further configured to acquire a plurality of partial X-ray images via the partial photographing operations and to obtain an X-ray image of the area between the top indicator and the bottom limit by combining the partial X-ray images.

The X-ray radiator may include a collimator configured to adjust a region to be irradiated with X-rays. The controller may be further configured to control the collimator such that the region to be irradiated with X-rays corresponds to each of the regions for the partial photographing operations.

The medical imaging apparatus may further include a communicator configured to receive the image obtained by photographing the object from an X-ray apparatus.

The controller may be further configured to determine the number of partial photographing operations based on the bottom limit and to control the X-ray apparatus to perform a partial photographing operation on a portion of the object that corresponds to an area between the top indicator and the bottom limit in the image based on the determined number of partial photographing operations.

The controller may be further configured to acquire a plurality of partial X-ray images via the partial photographing operations and to combine the partial X-ray images, thereby obtaining an X-ray image of the area between the top indicator and the bottom limit.

The medical imaging apparatus may further include an input device configured to receive a user input that relates to selecting a partial imaging mode, such that when the partial imaging mode is selected, the output device is further configured to display the top indicator and the at least one guideline on the image.

In another aspect, one or more exemplary embodiments provides a medical imaging apparatus that includes an output device and a controller. The controller is configured to control the output device to display an image obtained by photographing an object and to display, on the image, a plurality of Automatic Exposure Control (AEC) markers that respectively indicate positions of a plurality of AEC chambers included in an X-ray detector.

The controller may be further configured to set an on/off state of each of the AEC markers and to turn on or off each respective AEC chamber in the X-ray detector based on the set on/off state of each corresponding one of the AEC markers.

The medical imaging apparatus may further include an input device configured to receive a user input that relates to setting an on/off state of an AEC marker selected from among the AEC markers.

The controller may be further configured to detect, from among the AEC markers, an AEC chamber which is located outside the object and to turn off the detected AEC chamber.

The output device may be further configured to display, on the image, a collimation area that corresponds to a region to be irradiated with X-rays radiated by an X-ray radiator.

The medical imaging apparatus may further include an input device configured to receive a user input that relates to adjusting the collimation area on the image.

The controller may be further configured to adjust a collimator included in the X-ray radiator based on the adjusted collimation area.

The medical imaging apparatus may further include an input device configured to receive a user input that relates to an instruction for turning on of a lamp of a collimator. The output device may be further configured to display the AEC markers on the image that is obtained by photographing the object when the lamp of the collimator is turned on.

The medical imaging apparatus may further include an image acquirer configured to acquire the image by photographing the object.

The medical imaging apparatus may further include a communicator configured to receive the image from an X-ray apparatus.

In yet another aspect, one or more exemplary embodiments provides a method for operating a medical imaging apparatus. The method includes: acquiring an image obtained by photographing an object; and displaying, over the image, a top indicator that relates to setting a top limit for an area to be X-rayed and at least one guideline that indicates a bottom limit for the area to be X-rayed based on the top indicator and a number of partial photographing operations.

The method may further include: receiving a user input that relates to adjusting a position of the top indicator on the image; and displaying at least one guideline that is changed based on the adjusted position of the top indicator.

The method may further include receiving a user input that relates to setting a bottom limit for the area to be X-rayed.

The method may further include: determining the number of partial photographing operations based on the bottom limit; partitioning an area between the top indicator and the bottom limit in the image into regions for the partial photographing operations based on the determined number of partial photographing operations; and displaying the regions of the partial photographing operations on the image.

The method may further include highlighting overlapping portions between the regions for the partial photographing operations.

The method may further include displaying a bottom indicator that relates to setting the bottom limit for the area to be X-rayed. The received user input that relates to setting the bottom limit for the area to be X-rayed may be used for adjusting a position of the bottom indicator.

The method may further include: determining the number of partial photographing operations to be performed on an area between the top and bottom indicators; and partitioning the area between the top and bottom indicators in the image into equally sized regions based on the determined number of partial photographing operations. The at least one guideline may indicate a respective bottom limit for each of the regions.

The method may further include: redetermining, when a user input that relates to adjusting a position of at least one of the top and bottom indicators is received, the number of partial photographing operations based on the adjusted position of the at least one of the top and bottom indicators; repartitioning an area between the top and bottom indicators into equally sized regions based on the redetermined number of partial photographing operations; and redisplaying the changed at least one guideline that indicates the bottom limit for each of the regions.

The method may further include displaying a plurality of automatic exposure control (AEC) markers in each of the regions for the partial photographing operations displayed on the image, such that each respective one of the AEC markers indicates a corresponding one of a plurality of AEC chambers included in an X-ray detector during a partial photographing operation with respect to each of the regions for the partial photographing operations.

The method may further include: setting an on/off state of each of the AEC markers; and turning on or off each respective AEC chamber in the X-ray detector based on the set on/off state of each corresponding one of the AEC markers during a partial photographing operation.

The method may further include receiving a user input that relates to setting an on/off state of an AEC marker selected from among the AEC markers displayed on the image.

The method may further include: detecting, from among the AEC markers displayed on the image, an AEC chamber which is located outside the object; and turning off the detected AEC chamber.

The method may further include photographing the object in order to acquire the image.

The method may further include: determining the number of partial photographing operations based on the bottom limit; partitioning an area between the top indicator and the bottom limit in the image into regions for the partial photographing operations based on the determined number of partial photographing operations; and controlling an X-ray radiator to perform the partial photographing operations on the regions.

The method may further include: acquiring a plurality of partial X-ray images via the partial photographing operations; and acquiring an X-ray image of the area between the top indicator and the bottom limit by combining the partial X-ray images.

The X-ray radiator may include a collimator configured to adjust a region to be irradiated with X-rays. The method may further include controlling the collimator such that the region to be irradiated with X-rays corresponds to each of the regions for the partial photographing operations.

The method may further include receiving the image obtained by photographing the object from an X-ray apparatus.

The method may further include: determining the number of partial photographing operations based on the bottom limit; and controlling the X-ray apparatus to perform a partial photographing operation on a portion of the object that corresponds to an area between the top indicator and the bottom limit in the image based on the determined number of partial photographing operations.

The method may further include: acquiring a plurality of partial X-ray images via the partial photographing operations; and acquiring an X-ray image of the area between the top indicator and the bottom limit by combining the partial X-ray images.

The method may further include: receiving a user input that relates to selecting a partial imaging mode; and displaying the top indicator and the at least one guideline on the image when the partial imaging mode is selected.

In still another aspect, one or more exemplary embodiments provides a method for operating a medical imaging apparatus. The method includes: acquiring an image obtained by photographing an object; and displaying, on the image, a plurality of Automatic Exposure Control (AEC) markers that respectively indicate positions of a plurality of AEC chambers included in an X-ray detector.

The method may further include: setting an on/off state of each of the AEC markers; and turning on or off each respective AEC chamber in the X-ray detector based on the set on/off state of each corresponding one of the AEC markers.

The method may further include receiving a user input that relates to setting an on/off state of an AEC marker selected from among the AEC markers.

The method may further include: detecting, from among the AEC markers, an AEC chamber which is located outside the object; and turning off the detected AEC chamber.

The method may further include displaying, on the image, a collimation area that corresponds to a region to be irradiated with X-rays radiated by an X-ray radiator.

The method may further include receiving a user input that relates to adjusting the collimation area on the image.

The method may further include adjusting a collimator included in the X-ray radiator based on the adjusted collimation area.

The method may further include: receiving a user input that relates to an instruction for turning on of a lamp of a collimator; and displaying the AEC markers on the image that is obtained by photographing the object when the lamp of the collimator is turned on.

The method may further include photographing the object in order to acquire the image.

The method may further include receiving the image from an X-ray apparatus.

In yet another aspect, one or more exemplary embodiments provides a non-transitory computer-readable recording medium having recorded thereon a program for performing any one of the methods described above.

BRIEF DESCRIPTION OF THE DRAWINGS

These and/or other aspects will become apparent and more readily appreciated from the following description of the exemplary embodiments, taken in conjunction with the accompanying drawings in which:

FIGS. 10A and 10B illustrate an example in which the medical imaging apparatus of FIG. 9 receives a user input for adjusting a position of a top indicator;

FIGS. 11A and 11B illustrate an example in which the medical imaging apparatus of FIG. 9 adjusts a position of a top indicator as shown in FIGS. 10A and 10B and then receives a user input for readjusting the position of the top indicator;

FIGS. 27A and 27B illustrate another example in which an X-ray apparatus receives a user input for setting a bottom limit for an area to be X-rayed and displays regions for partial photographing operations over an image;

DETAILED DESCRIPTION

Figure 1:
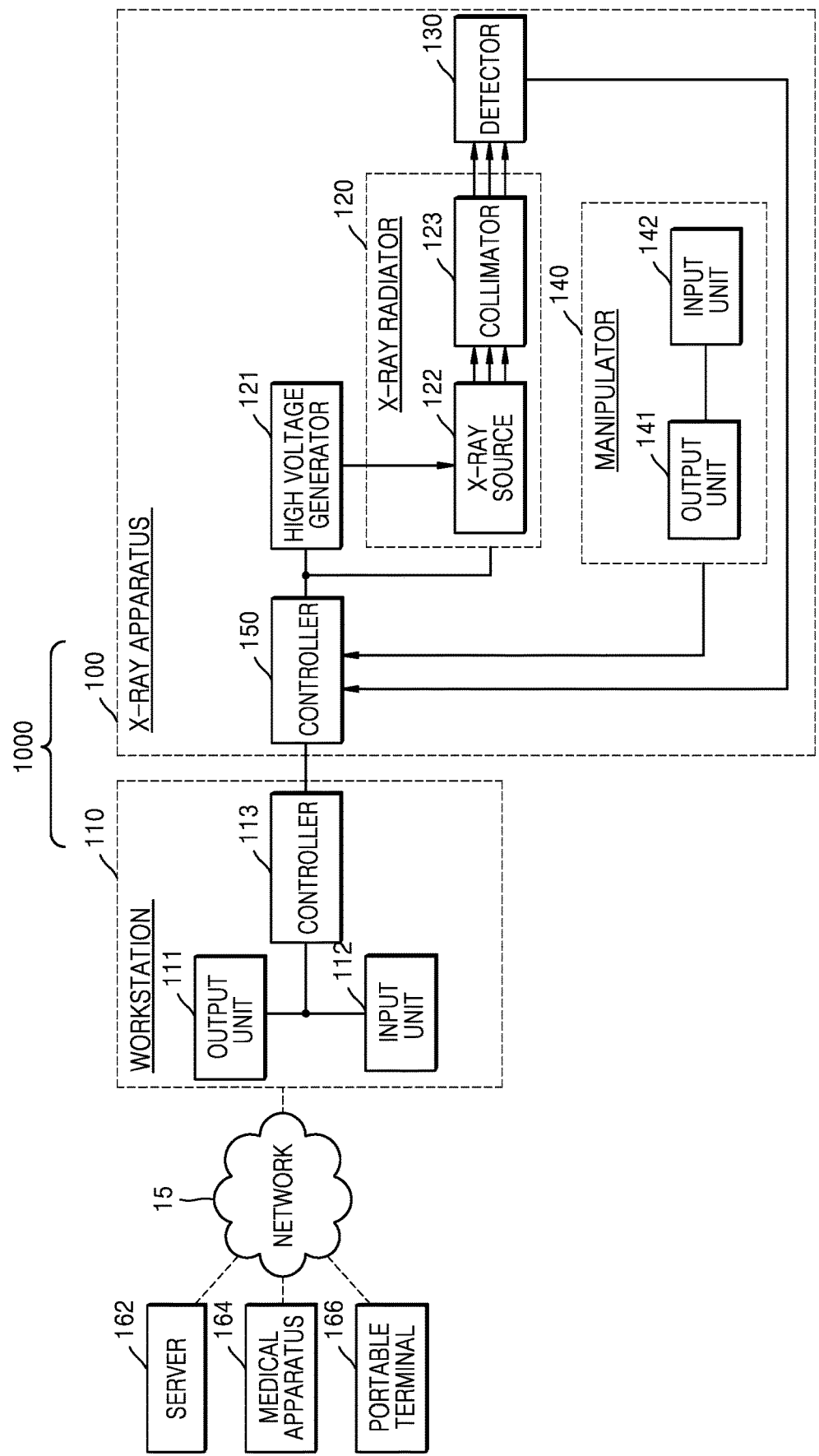
FIG. 1 is a block diagram of a configuration of an X-ray system.

The attached drawings for illustrating exemplary embodiments are referred to in order to gain a sufficient understanding of the present disclosure, the merits thereof, and the objectives accomplished by the implementation of the present disclosure. In this regard, the exemplary embodiments may have different forms and should not be construed as being limited to the descriptions set forth herein. Rather, these exemplary embodiments are provided so that this disclosure will be thorough and complete and will fully convey the concept of the exemplary embodiments to one of ordinary skill in the art, and the present disclosure will only be defined by the appended claims.

Hereinafter, the terms used in the specification will be briefly described, and then the exemplary embodiments will be described in detail.

The terms used in this specification are those general terms currently widely used in the art in consideration of functions regarding the exemplary embodiments, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the exemplary embodiments. Expressions such as "at least one of," when preceding a list of elements, modify the entire list of elements and do not modify the individual elements of the list.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be any of a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122, which receives the high voltage from the high voltage generator 121 in order to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode that includes a cathode and an anode. An inside of the X-ray tube is set as a high vacuum state of about 10 mm Hg, and a filament of the anode is heated to a high temperature in order to generate thermal electrons. The filament may be a tungsten filament, and a voltage of about 10 V and a current of about 3 to 5 A may be applied to an electric wire connected to the filament in order to heat the filament.

In addition, when a high voltage of about 10 kVp to about 300 kVp is applied between the cathode and the anode, the thermal electrons are accelerated so as to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material, such as, for example, any of chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, an energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has propagated through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit (also referred to herein as an "output device") 141 and an input unit (also referred to herein as an "input device") 142. The input unit 142 may receive, from a user, a command for manipulating the X-ray apparatus 100 and various types of information related to X-ray photographing. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit (also referred to herein as an "output device") 111, an input unit (also referred to herein as an "input device") 112, and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In this aspect, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. In some exemplary embodiments, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, exemplary embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include any one or more of a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In particular, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input via the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulator 140; however, the exemplary embodiments are not limited thereto, and the output unit 141 or a portion of the output unit 141 may be located elsewhere. For example, the output unit 141 may be located on a wall of an examination room in which the X-ray photographing of the object is performed.

The controllers 113 and 150 control locations of the X-ray radiator 120 and the detector 130, photographing timing, and photographing conditions, according to photographing conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the controllers 113 and 150 adjust the location of the detector 130 according to a predetermined photographing condition, and control operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, and/or object information. Examples of the output units 111 and 141 may include any one or more of a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Further, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include any of a local area communication module, a wired communication module, and/or a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include any one or more of a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
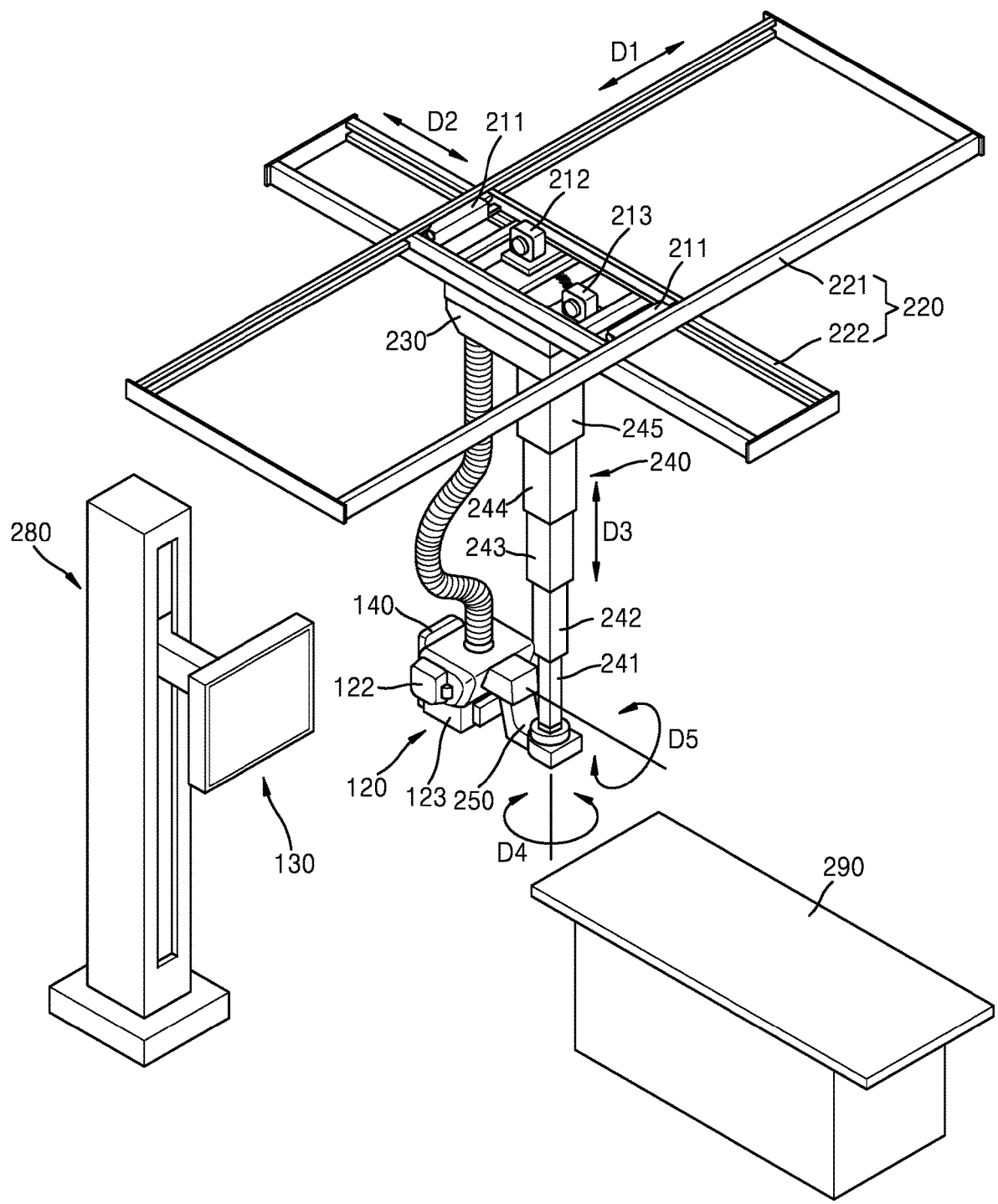
FIG. 2 is a perspective view of a fixed-type X-ray apparatus.

FIG. 2 is a perspective view of a fixed type X-ray apparatus 200. The fixed type X-ray apparatus 200 may be another exemplary embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 configured for radiating an X-ray to an object, a detector 130 configured detecting an X-ray that has passed through the object, first, second, and third motors 211, 212, and 213 configured for providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Further, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a driving power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

Although FIG. 2 shows the fixed type X-ray apparatus 200 connected to the ceiling of the examination room, the fixed type X-ray apparatus 200 is merely an example for convenience of comprehension. In this aspect, X-ray apparatuses according to exemplary embodiments may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
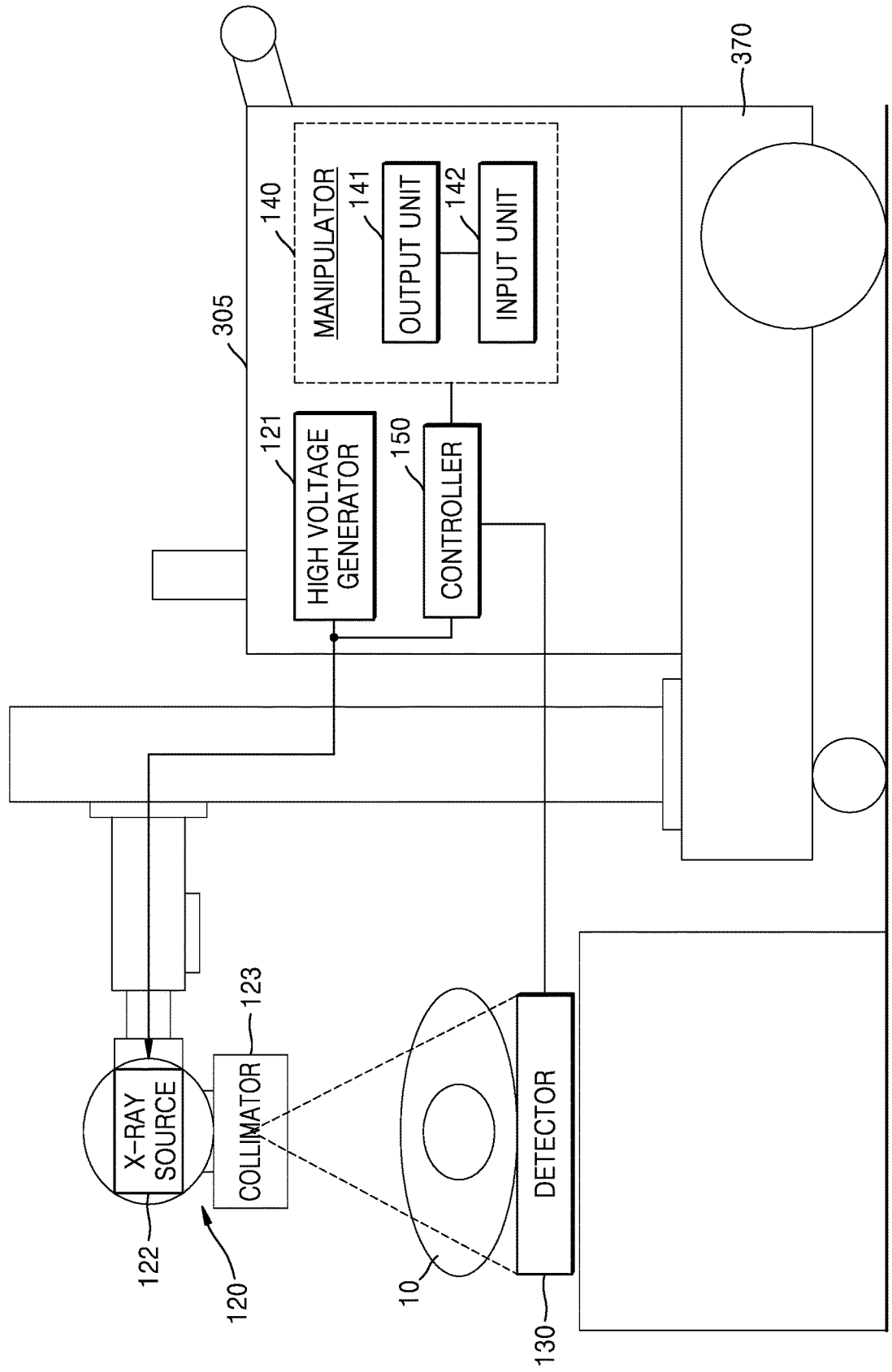
FIG. 3 is a block diagram of a configuration of a mobile X-ray apparatus.

FIG. 3 is a diagram showing a configuration of a mobile X-ray apparatus 300 capable of performing an X-ray photographing operation regardless of a place where the photographing operation is performed. The mobile X-ray apparatus 300 may be another exemplary embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 configured detecting an X-ray that is radiated from the X-ray radiator 120 toward an object and that propagates through the object. The main unit 305 includes a manipulator 140 configured for providing a user with an interface for manipulating the mobile X-ray apparatus 300, a high voltage generator 121 configured for generating a high voltage applied to an X-ray source 122, and a controller 150 configured for controlling overall operations of the mobile X-ray apparatus 300. The X-ray radiator 120 includes the X-ray source 122 configured for generating the X-ray, and a collimator 123 configured for guiding a path along which the generated X-ray is emitted from the X-ray source 122 and adjusting an irradiation region radiated by the X-ray.

The detector 130 in FIG. 3 may not be combined with any receptor, and the detector 130 may be a portable detector which can exist anywhere.

In FIG. 3, the manipulator 140 is included in the main unit 305; however, exemplary embodiments are not limited thereto. For example, as illustrated in FIG. 2, the manipulator 140 of the mobile X-ray apparatus 300 may be disposed on a side surface of the X-ray radiator 120.

Figure 4:
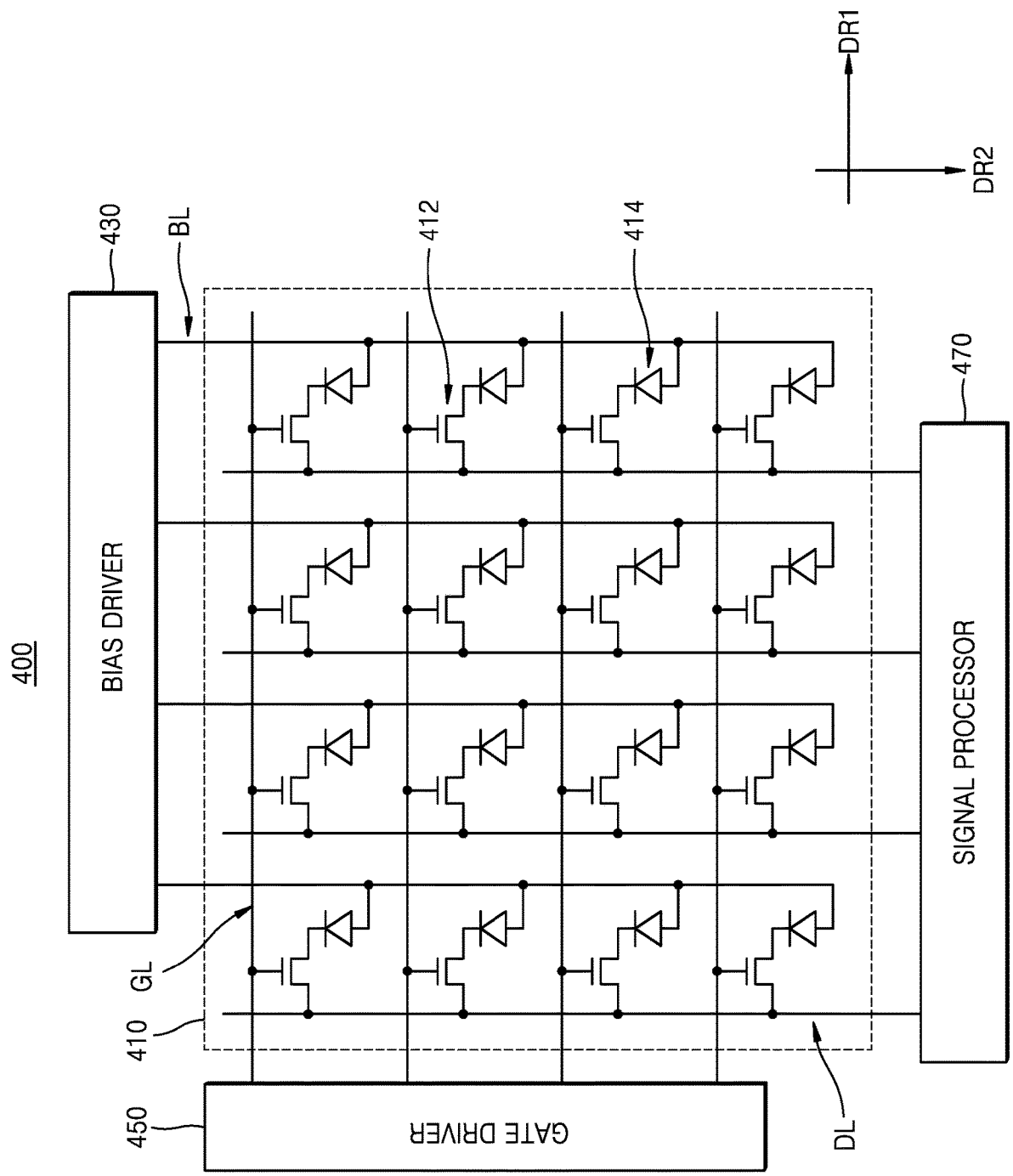
FIG. 4 is a schematic diagram showing a detailed configuration of a detector.

FIG. 4 is a schematic diagram showing a detailed configuration of a detector 400. The detector 400 may be an exemplary embodiment of the detector 130 of FIGS. 1, 2, and 3. The detector 400 may be an indirect type detector.

Referring to FIG. 4, the detector 400 may include a scintillator (not shown), a photodetecting substrate 410, a bias driver 430, a gate driver 450, and a signal processor 470.

The scintillator receives the X-ray radiated from the X-ray source 122 and converts the received X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. Conversely, the bias lines BL may be formed to be substantially parallel with the first direction DR1 so as to be electrically connected to the photodiodes 414. FIG. 4 shows four bias lines BL formed along the second direction DR2 as an example.

The bias driver 430 is electrically connected to the bias lines BL so as to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 so as to apply a reverse bias voltage to the photodiodes 414. Conversely, the bias driver 430 may apply a voltage that is greater than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. Conversely, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data. The signal processor 470 may output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit (also referred to herein as a "battery") and a wireless communication interface unit (also referred to herein as a "wireless communication interface").

Figure 5:
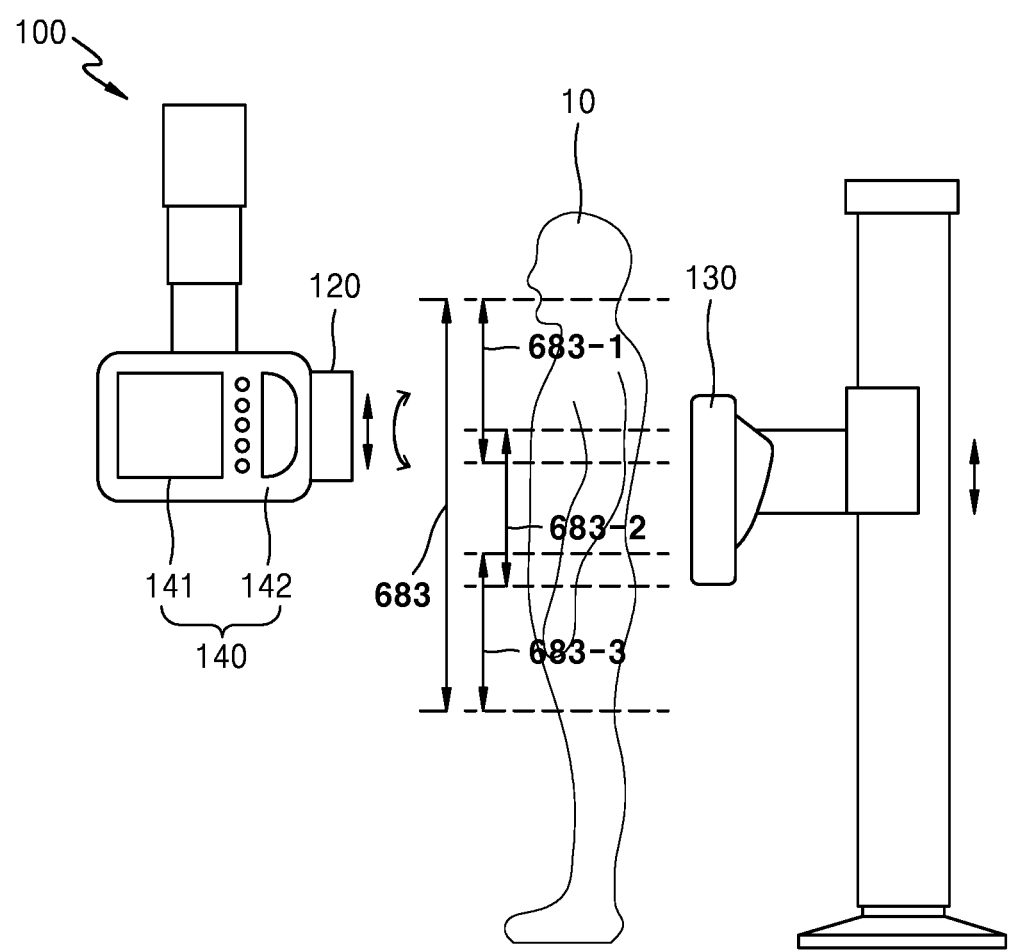
FIG. 5 is an example where an X-ray apparatus performs partial photographing operations with respect to an object.

FIG. 5 is an example where an X-ray apparatus 100 performs partial photographing operations on an object 10.

Referring to FIG. 5, the X-ray apparatus 100 may include an X-ray radiator 120, a detector 130, and a manipulator 140. The manipulator 140 may include an output unit 141 and an input unit 142. Since the X-ray apparatus 100 of FIG. 5 is an example of the X-ray apparatus 100 shown in FIG. 1, the X-ray apparatus 100 of FIG. 5 may further include other components included in the X-ray apparatus 100 shown in FIG. 1.

A size of a region of interest (ROI) 683 of the object 10 for which a user desires to acquire an X-ray image may be greater than that of the detector 130. The X-ray apparatus 100 may not acquire an X-ray image of the ROI 683 via a single X-ray photographing operation.

The X-ray apparatus 100 may partition the ROI 683 of the object 10 into first, second, and third portions 683-1, 683-2, and 683-3 and perform X-ray photographing operations respectively on the first, second, and third portions 683-1, 683-2, and 683-3. In this way, an X-ray photographing operation performed by the X-ray apparatus 100 on each of the first, second, and third portions 683-1, 683-2, and 683-3 is referred to as a "partial photographing operation".

To perform partial photographing operations on the first, second, and third portions 683-1, 683-2, and 683-3, the X-ray apparatus 100 may rotate or move vertically the X-ray radiator 120. Furthermore, the X-ray apparatus 100 may move the detector 130 to positions respectively corresponding to the first, second, and third portions 683-1, 683-2, and 683-3. The collimator 123 included in the X-ray radiator 120 may adjust a region being irradiated with X-rays (hereinafter, referred to as an "X-ray irradiation region") to correspond to each of the portions 683-1, 683-2, and 683-3.

Referring to FIG. 5, the X-ray apparatus 100 may take X-rays of the entire ROI 683 that is the sum of the first, second, and third portions 683-1, 683-2, and 683-3 by performing three partial photographing operations respectively on the first, second, and third portions 683-1, 683-2, and 683-3. However, FIG. 5 is merely an example of partial photographing, and the number of times a partial photographing operation is performed is not limited to three (3).

The X-ray apparatus 100 may acquire a plurality of X-ray images via partial photographing and stitch the plurality of X-ray images together (i.e., combine the plurality of X-ray images), thereby obtaining a single X-ray image. Hereinafter, in the present specification, a plurality of X-ray images acquired via partial photographing are referred to as "a plurality of partial X-ray images". A single X-ray image obtained by stitching the "plurality of partial X-ray images" together is also referred to as a "stitched image" and/or as a "combined image".

Figure 6:
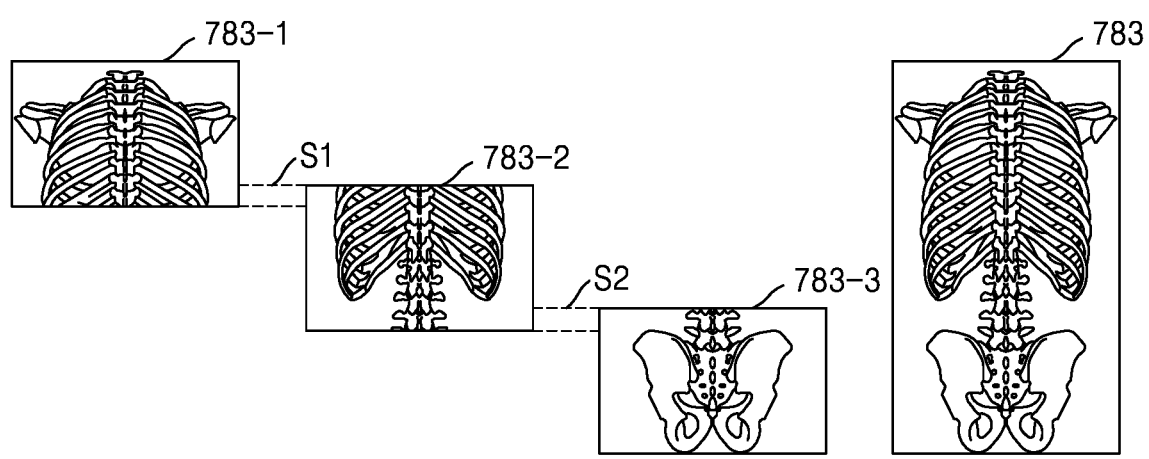
FIG. 6 is an example of partial X-ray images acquired through three partial X-ray photographing operations by the X-ray apparatus of FIG. 5 and a stitched image.

FIG. 6 is an example of partial X-ray images acquired through three partial X-ray photographing operations by the X-ray apparatus 100 of FIG. 5 and a stitched image.

Referring to FIG. 6, by performing partial photographing operations on the first, second, and third portions (683-1, 683-2, and 683-3 of FIG. 5) as shown in FIG. 5, the X-ray apparatus 100 may acquire partial X-ray images 783-1, 783-2, and 783-3 respectively corresponding to the first, second, and third portions 683-1, 683-2, and 683-3. The X-ray apparatus 100 may obtain a single X-ray image 783, i.e., a stitched image by stitching the partial X-ray images 783-1, 783-2, and 783-3 together. Stitching is an image processing technique for combining the partial X-ray images 783-1, 783-2, and 783-3 into the single X-ray image 783. Stitching may be also an image processing technique for detecting overlapping portions S1 and S2 between each of the partial X-ray images 783-1, 783-2, and 783-3 and combining the overlapping portions S1 and S2 together.

In this way, an X-ray image of the ROI (683 of FIG. 5) of the object (10 of FIG. 5) that is larger than a size of the detector 130 may be acquired by performing partial photographing and stitching operations.

Stitching may be performed by the controller 150 included in the X-ray apparatus 100 of FIG. 1 or the controller 113 included in the workstation 110 connected to the X-ray apparatus 100. An operation of the X-ray apparatus 100 for performing partial photographing may be controlled by the controller 150 of the X-ray apparatus 100 or the controller 113 of the workstation 110.

Figure 7:
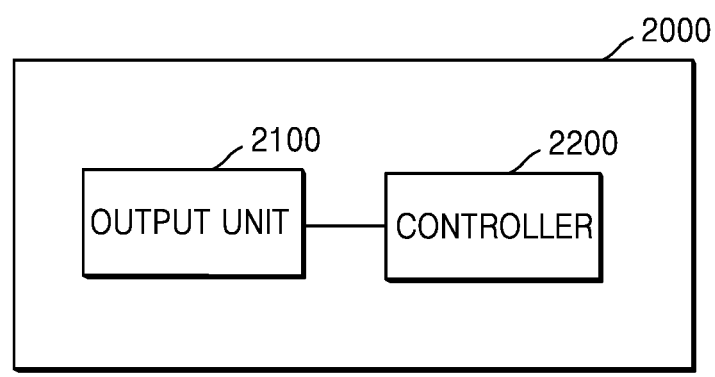
FIG. 7 is a block diagram of a configuration of a medical imaging apparatus, according to an exemplary embodiment.

FIG. 7 is a block diagram of a configuration of a medical imaging apparatus 2000, according to an exemplary embodiment.

Referring to FIG. 7, the medical imaging apparatus 2000 according to the present exemplary embodiment includes an output unit 2100 and a controller 2200.

The medical imaging apparatus 2000 may be included in an X-ray apparatus or a workstation configured for controlling the X-ray apparatus.

When the medical imaging apparatus 2000 is included in an X-ray apparatus, the descriptions with respect to the X-ray apparatuses 100, 200, and 300 may be applied to the medical imaging apparatus 2000 even if not expressly specified here. The output unit 2100 and the controller 2200 correspond to the output unit 141 and the controller 150 of the X-ray apparatus (100 of FIG. 1), respectively. The medical imaging apparatus 2000 may also be controlled by the workstation (110 of FIG. 1).

When the medical imaging apparatus 2000 is included in a workstation, the description with respect to the workstation 110 may be applied to the medical imaging apparatus 2000 even if not expressly specified here. The output unit 2100 and the controller 2200 correspond to the output unit 111 and the controller 150 of the X-ray apparatus (100 of FIG. 1), respectively. In this case, the medical imaging apparatus 2000 may control the X-ray apparatus.

The controller 2200 may control overall operations of the medical imaging apparatus 2000. The controller 2200 may process data, images, etc. necessary for operations of the medical imaging apparatus 2000. The controller 2200 may include any one or more of a central processing unit (CPU), a microprocessor, a graphics processing unit (GPU), etc., but is not limited thereto.

The controller 2200 may control the output unit 2100. The output unit 2100 may be controlled by the controller 2200 to output images, data, etc. The controller 2200 may acquire images, data, etc. that are output by the output unit 2100 by performing image processing, data processing, etc.

According to an exemplary embodiment, the output unit 2100 may display an image obtained by photographing an object. An image (11 of FIG. 8) displayed on the output unit 2100 is obtained by photographing an object via an image acquisition device, such as a camera, and is distinguished from an X-ray image acquired by performing X-ray photographing of the object. The image 11 may be a still image of the object or an image obtained by imaging the object in real-time.

The output unit 2100 may display a top indicator for setting a top limit for an area to be X-rayed and at least one guideline over an image obtained by photographing an object. The at least one guideline indicates a bottom limit for the area to be X-rayed according to the top indicator and the number of times a partial photographing operation is to be performed (hereinafter, referred to as 'the number of partial photographing operations'). In particular, the output unit 2100 may display the top indicator and the at least one guideline so that they are superimposed on the image obtained by photographing the object.

As the number of partial photographing operations increases, the amount of X-rays being irradiated on the object increases. To prevent excessive irradiation, an X-ray image of an ROI may be acquired by performing a minimum number of partial photographing operations of the ROI. By viewing the output unit 2100, the user may intuitively recognize the number of partial photographing operations necessary for acquiring an X-ray image of an area between the top indicator and the at least one guideline. In this aspect, the medical imaging apparatus 2000 is configured to allow the user to intuitively and conveniently recognize the optimal number of partial photographing operations, thereby preventing excessive X-ray irradiation.

Figure 8:
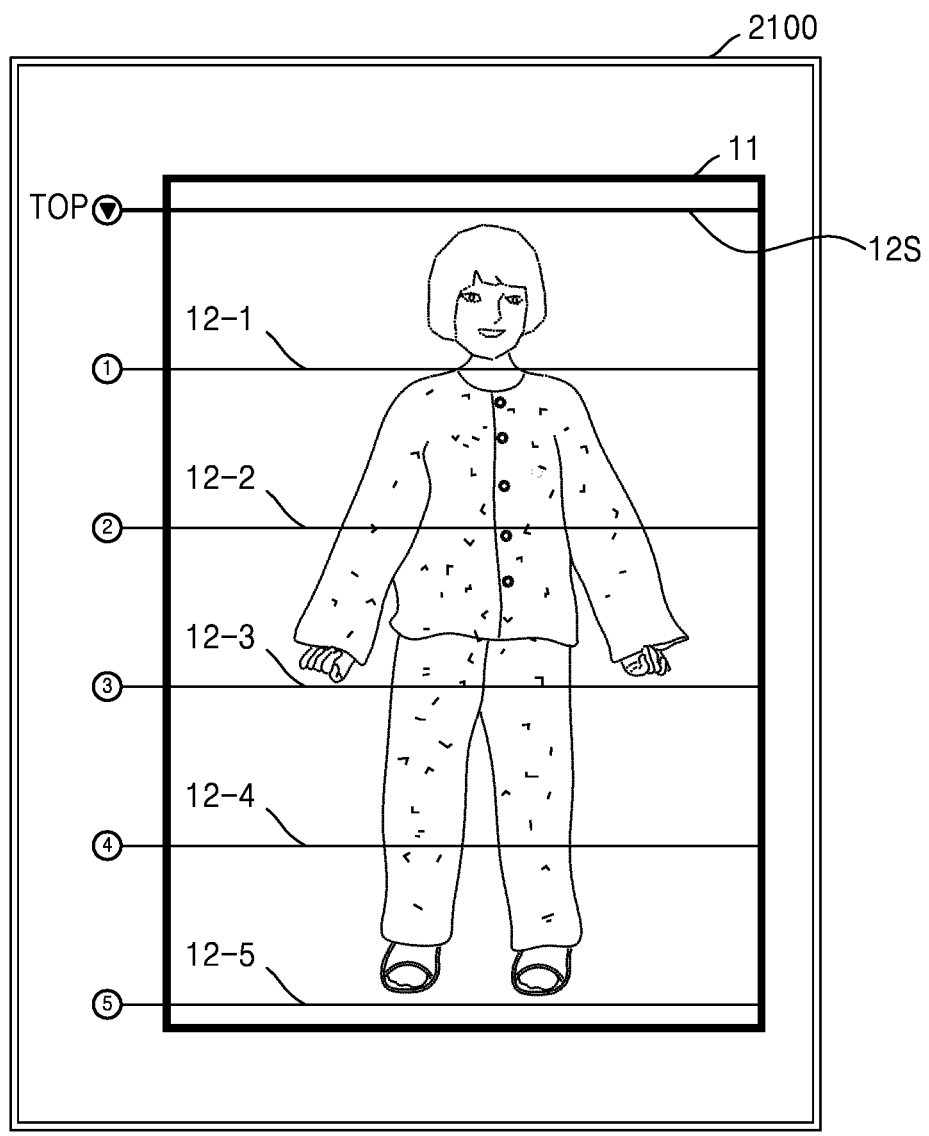
FIG. 8 is an example in which an output unit of the medical imaging apparatus of FIG. 7 displays a top indicator and a plurality of guidelines over an image obtained by photographing an object.

FIG. 8 is an example in which the output unit 2100 of the medical imaging apparatus 2000 of FIG. 7 displays a top indicator 12S and a plurality of guidelines 12-1 through 12-5 over an image obtained by photographing an object.

Referring to FIG. 8, the output unit 2100 may display the top indicator 12S for setting a top limit for an area to be X-rayed and the plurality of first, second, third, fourth, and fifth guidelines 12-1, 12-2, 12-3, 12-4, and 12-5. The first through fifth guidelines 12-1 through 12-5 indicate a bottom limit for the area to be X-rayed according to the top indicator 12S and the number of partial photographing operations.

Each of the first through fifth guidelines 12-1 through 12-5 corresponds to the number of partial photographing operations. The first guideline 12-1 corresponds to a single partial photographing operation. The second and third guidelines 12-2 and 12-3 respectively correspond to two and three partial photographing operations. The fourth and fifth guidelines 12-4 and 12-5 respectively correspond to four and five partial photographing operations.

Each of the first through fifth guidelines 12-1 through 12-5 indicates a bottom limit for an area to be X-rayed according to the top indicator 12S and its corresponding number of partial photographing operations. An X-ray image of an area in the image 11 between the top indicator 12S and the first guideline 12-1 may be acquired by performing a single partial photographing operation.

An X-ray image of an area in the image 11 between the top indicator 12S and the second guideline 12-2 may be acquired by performing a partial photographing operation twice. In particular, the area between the top indicator 12S and the second guideline 12-2 is divided into two regions, and two partial X-ray images may be acquired by performing partial photographing operations on the two regions. The two partial X-ray images are stitched together to acquire a single X-ray image of the area between the top indicator 12S and the second guideline 12-2.

An X-ray image of an area in the image 11 between the top indicator 12S and the third guideline 12-3 may be acquired by performing a partial photographing operation three times. Similarly, an X-ray image of an area in the image 11 between the top indicator 12S and the fourth guideline 12-4 may be acquired by performing a partial photographing operation four times. An X-ray image of an area in the image 11 between the top indicator 12S and the fifth guideline 12-5 may be acquired by performing a partial photographing operation five times.

The output unit 2100 may further display a symbol identifying the displayed top indicator 12S around the top indicator 12S. While FIG. 8 shows that a character "TOP" and a downward-pointing arrow are further displayed as a symbol identifying the top indicator 12S, exemplary embodiments are not limited thereto.

The output unit 2100 may further display symbols indicating the number of partial photographing operations near the plurality of guidelines 12-1 through 12-5. Although FIG. 8 shows that numbers 1, 2, 3, 4, and 5 are further displayed as the symbols, exemplary embodiments are not limited thereto.

While FIG. 8 shows that the five (5) guidelines (the first through fifth guidelines 12-1 through 12-5) are displayed over the image 11, the number of guidelines displayed over the image 11 is not limited to 5. For example, if an X-ray image of an area in the image 11 is acquired by performing a single photographing operation, the output unit 2100 may display only a single guideline over the image 11. Even if the following figures show that the output unit 2100 displays a plurality of guidelines, it is to be noted that this does not preclude a case where the output unit 2100 displays only a single guideline.

If the medical imaging apparatus 2000 of FIG. 7 is included in an X-ray apparatus, the medical imaging apparatus 2000 may further include an image acquisition unit (also referred to herein as a "image acquirer") configured for acquiring the image 11 by photographing an object. The image acquisition unit may be realized as a camera that is a general image acquisition device. If the medical imaging apparatus 2000 is included in a workstation, the medical imaging apparatus 2000 may receive the image 11 obtained by photographing the object from the X-ray apparatus. In this case, the medical imaging apparatus 2000 may further include a communication unit (also referred to herein as a "communicator") configured to receive the image 11.

The controller 2200 may perform geometric registration of the image 11 by matching each point in the image 11 with a position in the real world.

The controller 2200 may acquire a position of an actual area to be X-rayed according to the number of partial photographing operations, and coordinating the actual area to be X-rayed with the image 11 that has been registered geometrically. Thus, the controller 2200 may perform image processing whereby the top indicator 12S and the first through fifth guidelines 12-1 through 12-5 are superimposed onto the image 11.

The controller 2200 may control the output unit 2100 to display the image 11 on which the top indicator 12S and the first through fifth guidelines 12-1 through 12-5 are superimposed.

As the number of partial photographing operations increases, the amount of X-rays being irradiated on the object increases. To prevent excessive irradiation, an X-ray image of an ROI may be acquired by performing a minimum number of partial photographing operations of the ROI. The user may intuitively recognize via the output unit 2100 the number of partial photographing operations necessary for acquiring an X-ray image of an area between the top indicator 12S and each of the first through fifth guidelines 12-1 through 12-5. In this aspect, the medical imaging apparatus 2000 is configured to allow the user to intuitively and conveniently recognize the optimal number of partial photographing operations, thereby preventing excessive X-ray irradiation.

According to an exemplary embodiment, each of the first through fifth guidelines 12-1 through 12-5 may indicate a bottom limit for a maximum region for which an X-ray image is to be acquired according to the top indicator 12S and its corresponding number of partial photographing operations. The maximum region may be obtained by adjusting a size of an X-ray irradiation region to the maximum via the collimator 123 of the X-ray apparatus (100 of FIG. 1). In particular, by adjusting an X-ray irradiation region to the maximum via the collimator 123, each of the first through fifth guidelines 12-1 through 12-5 may indicate a bottom limit for a region for which an X-ray image is to be acquired and which is determined according to its corresponding number of partial photographing operations.

The first guideline 12-1 may be a bottom limit for a maximum region for which an X-ray image is to be acquired by performing a single X-ray photographing operation. The second guideline 12-2 may be a bottom limit for a maximum region for which an X-ray image is to be acquired by performing an X-ray photographing operation twice. The third guideline 12-3 may be a bottom limit for a maximum region for which an X-ray image is to be acquired by performing an X-ray photographing operation three times. The fourth guideline 12-4 may be a bottom limit for a maximum region for which an X-ray image is to be acquired by performing an X-ray photographing operation four times. The fifth guideline 12-5 may be a bottom limit for a maximum region for which an X-ray image is to be acquired by performing an X-ray photographing operation five times.

Figure 9:
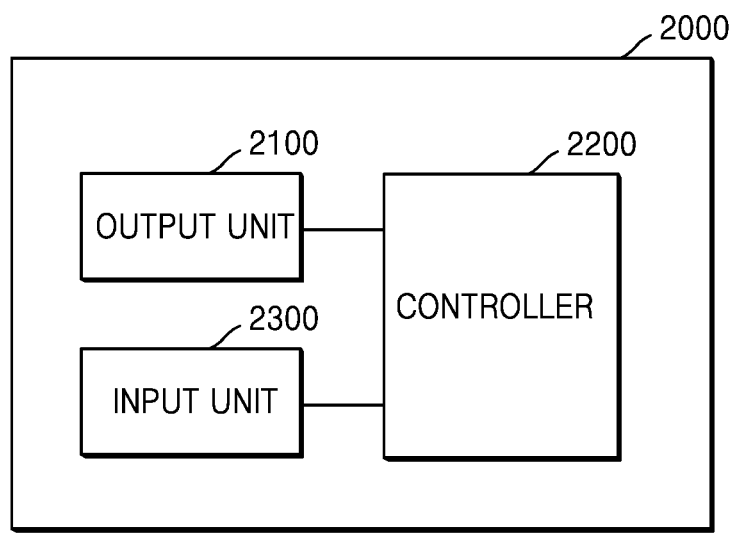
FIG. 9 is another block diagram of a configuration of the medical imaging apparatus of FIG. 7.

FIG. 9 is another block diagram of a configuration of the medical imaging apparatus of FIG. 7.

Referring to FIG. 9, the medical imaging apparatus 2000 may further include an input unit 2300 in addition to the output unit 2100 and the controller 2200.

The input unit 2300 may receive user inputs such as commands for manipulating the medical imaging apparatus 2000 and various kinds of information. The controller 2200 may control or manipulate the medical imaging apparatus 2000 based on a user input received by the input unit 2300. The input unit 2300 shown in FIG. 9 may correspond to the input units (112 and 142 of FIG. 1), and thus the same descriptions as already provided above with respect to FIG. 1 will be omitted below.

As described above, the output unit 2100 may display a top indicator for setting a top limit for an area to be X-rayed and at least one guideline so that the top indicator and the at least one guideline are superimposed on an image obtained by photographing an object.

The input unit 2300 may receive a user input for adjusting a position of the top indicator on the image. The controller 2200 may change a position of the at least one guideline on the image according to the position of the top indicator adjusted via the user input.

The output unit 2100 may display over the image the at least one guideline whose position has been changed according to the adjusted top indicator.

FIGS. 10A and 10B illustrate an example in which the medical imaging apparatus 2000 of FIG. 9 receives a user input for adjusting a position of a top indicator 12S. It is assumed here that the output unit 2100 includes the input unit 2300 formed as a touch screen, but only the output unit 2100 is shown in FIGS. 10A and 10B for convenience. Even when the following figures other than FIGS. 10A and 10B show only the output unit 2100, it may be assumed hereinafter that the output unit 2100 includes the input unit 2300 formed as a touch screen.

Referring to FIG. 10A, the user may adjust a position of the top indicator 12S. In this aspect, the input unit 2300 may receive a user input for adjusting a position of the top indicator 12S. Although FIG. 10A shows that the user is able to adjust the position of the top indicator 12S by dragging the top indicator 12S with his or her finger, FIG. 10A is merely an example. The user input for adjusting the position of the top indicator 12S may be performed in various ways according to an implemented configuration of the input unit 2300. As another example, if the input unit 2300 includes a mouse, the user may adjust the position of the top indicator 12S by using the mouse.

When the position of the top indicator 12S is adjusted according to a user input as shown in FIG. 10A, the output unit 2100 may display, over an image 11, a plurality of guidelines 12-1 through 12-4 that are changed according to the top indicator 12S, and more particularly, based on the adjusted position of the top indicator 12S, as shown in FIG. 10B. The output unit 2100 may display the changed plurality of guidelines 12-1 through 12-4 over the image 11 in real-time as the position of the top indicator 12S is adjusted.

FIGS. 10A and 10B show that positions and number of a plurality of guidelines 12-1 through 12-5 are changed due to adjustment of the position of the top indicator 12S. In particular, the output unit 2100 displays the five (5) guidelines 12-1 through 12-5 before the adjustment of the position of the top indicator 12S but the four (4) guidelines 12-1 through 12-4 after the adjustment thereof. However, this is merely an example, and the original or changed number of guidelines is not limited thereto. For example, a plurality of guidelines may be displayed before the position of the top indicator 12S is changed, but only a single guideline may be displayed due to adjustment of the position of the top indicator 12S.

Even after the output unit 2100 displays the changed guidelines 12-1 through 12-4 due to adjustment of the position of the top indicator 12S as shown in FIG. 10B, the input unit 2300 may receive again a user input for readjusting the adjusted position of the top indicator 12S on the image 11. The output unit 2100 may display, over the image 11, the guidelines 12-1 through 12-4 that are changed again according to the readjusted top indicator 12S.

As described above, the position of the top indicator 12S may be adjusted via a user input, and the guidelines 12-1 through 12-4 that are changed according to the adjusted top indicator 12S may be displayed again over the image 11, thereby enabling the user to intuitively recognize the number of partial photographing operations necessary for acquiring an X-ray image of an ROI. In this aspect, the medical imaging apparatus 2000 is configured to allow the user to intuitively and conveniently recognize the optimal number of partial photographing operations, thereby preventing excessive X-ray irradiation.

FIGS. 11A and 11B illustrate an example in which the medical imaging apparatus 2000 of FIG. 9 adjusts a position of a top indicator 12S as shown in FIGS. 10A and 10B, and then receives a user input for readjusting the position of the top indicator 12S.

Referring to FIG. 11A, an ROI for which a user desires to acquire an X-ray image may be positioned between the top indicator 12S and a third guideline 12-3. Thus, the X-ray image of the ROI may be acquired by performing a partial photographing operation three times. However, if the user determines that a partial photographing operation is performed more than necessary compared to a size of the ROI, the user may readjust the position of the top indicator 12S. In particular, the input unit 2300 may receive again a user input for readjusting the position of the top indicator 12S over an image 11 obtained by photographing an object.

When the position of the top indicator 12S is readjusted according to the user input as shown in FIG. 11A, the output unit 2100 may display, over the image 11, first through fourth guidelines 12-1 through 12-4 that are changed again according to the readjusted top indicator 12S, as shown in FIG. 11B. As the position of the top indicator 12S is readjusted, and accordingly, the first through fourth guidelines 12-1 through 12-4 are changed again, the ROI may be positioned between the top indicator 12S and the second guideline 12-2. Thus, an X-ray image of the ROI may be acquired by performing a partial photographing operation twice.

While FIG. 11A shows that an X-ray image of an ROI may be acquired by performing a partial photographing operation three times, the number of partial photographing operations necessary for acquiring the X-ray image of the ROI may be reduced by adjusting the position of the top indicator 12S as shown in FIG. 11B.

According to an exemplary embodiment, the output unit 2100 may display the image 11 obtained by photographing the object and display, over the image 11, the top indicator 12S whose position may be adjusted by the user and at least one of the first through fourth guidelines 12-1 through 12-4 corresponding to the top indicator 12S and the number of partial photographing operations. This configuration allows the user to conveniently recognize the optimal number of partial photographing operations based on a size of an ROI, thereby preventing an unnecessary increase in the number of partial photographing operations, compared to a size of the ROI. Thus, the medical imaging apparatus 2000 may prevent excessive X-ray irradiation of the object.

After adjusting the position of the top indicator 12S on the image 11, the user may set a bottom limit for an area to be X-rayed. In particular, the input unit 2300 may receive a user input for setting the bottom limit for the area to be X-rayed.

Figure 12:
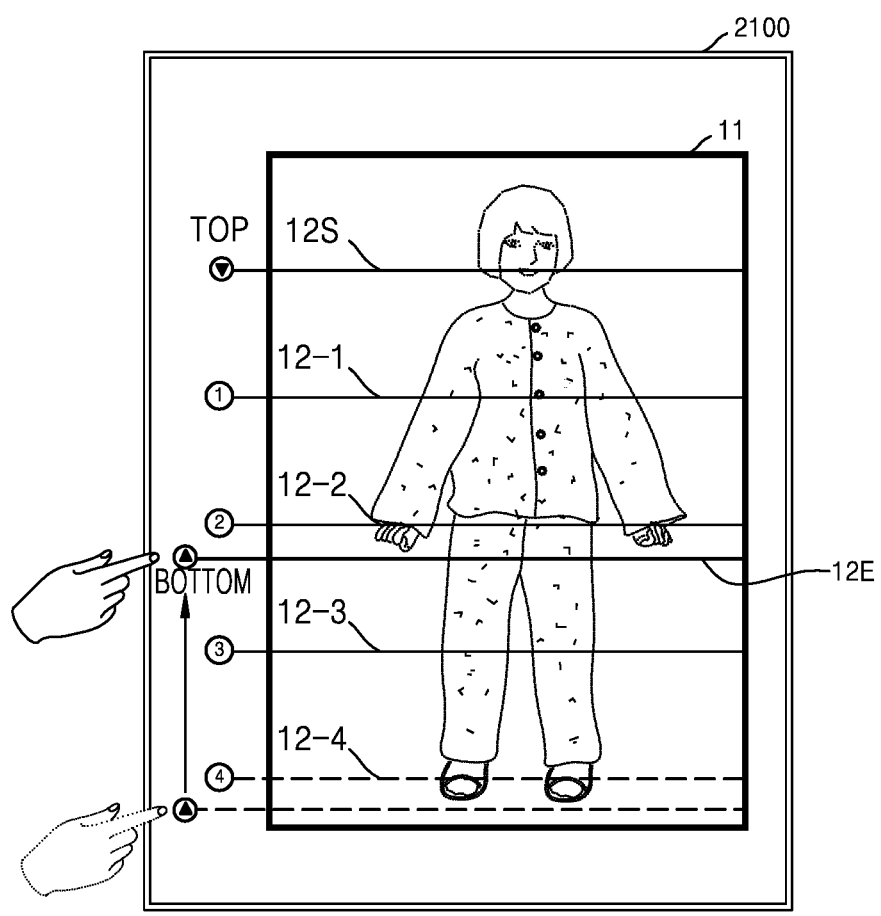
FIG. 12 is an example in which the medical imaging apparatus of FIG. 9 receives a user input for setting a bottom limit for an area to be X-rayed.

FIG. 12 is an example in which the medical imaging apparatus 2000 of FIG. 9 receives a user input for setting a bottom limit for an area to be X-rayed.

Referring to FIG. 12, the output unit 2100 may further display, over an image 11, a bottom indicator 12E for setting a bottom limit for an area to be X-rayed, in addition to the top indicator 12S and a plurality of first through fourth guidelines 12-1 through 12-4. In particular, the output unit 2100 may display the top indicator 12S, the guidelines 12-1 through 12-4, and the bottom indicator 12E over the image 11.

The input unit 2300 may receive a user input for adjusting a position of the bottom indicator 12E. The controller 2200 may set the position of the bottom indicator 12E at a bottom limit for an area to be X-rayed.

Although FIG. 12 shows that the user is able to adjust the position of the bottom indicator 12E by dragging the bottom indicator 12E with his or her finger, this is merely an example. The user input for adjusting the position of the bottom indicator 12E may be performed in various ways according to an implemented configuration of the input unit 2300. As another example, if the input unit 2300 includes a mouse, the user may adjust the position of the bottom indicator 12E by using the mouse.

The output unit 2100 may further display a symbol identifying the displayed bottom indicator 12E around the bottom indicator 12E. While FIG. 12 shows that a character "BOTTOM" and an upward-pointing arrow are further displayed as a symbol identifying the bottom indicator 12E, exemplary embodiments are not limited thereto.

Referring to FIG. 12, the bottom indicator 12E may be positioned between the second and third guidelines 12-2 and 12-3 via a user input. In this case, an X-ray image of an area between the top and bottom indicators 12S and 12E may be acquired by performing an X-ray photographing operation three times. To emphasize that the number of partial photographing operations is three (3), the output unit 2100 may display guidelines corresponding to more than three partial photographing operations, i.e., the fourth guideline 12-4, so as to be distinguished from the remaining first through third guidelines 12-1 through 12-3. As shown in FIG. 12, the fourth guideline 12-4 may be displayed as a dashed line. However, exemplary embodiments are not limited thereto, and the fourth guideline 12-4 may be displayed in different ways to be distinguished from the remaining first through third guidelines 12-1 through 12-3. For example, the fourth guideline 12-4 may be blurred or displayed in a different color.

FIG. 12 is merely an example of a user input for setting a bottom limit for an area to be X-rayed, and exemplary embodiments are not limited thereto. A bottom limit for an area to be X-rayed may be set by the user in various ways. As another example, the user may set a bottom limit for an area to be X-rayed by touching or clicking a location in the image 11 displayed on the output unit 2100. In this case, unlike in FIG. 12, the bottom indicator 12E may not be displayed over the image 11.

As described above, the input unit 2300 of the medical imaging apparatus 2000 may receive a user input for adjusting a position of the top indicator 12S or a user input for setting a bottom limit for an area to be X-rayed, for example, via adjustment of the position of the bottom indicator 12E.

The controller 2200 may determine the number of partial photographing operations based on a bottom limit for an area to be X-rayed. If the bottom indicator 12E is positioned between the second and third guide lines 12-2 and 12-3 as shown in FIG. 12, the controller 2200 may determine that the number of partial photographing operations is 3. Referring to FIG. 12, the controller 2200 may partition an area between the top and bottom indicators 12S and 12E into three (3) regions for partial photographing operations according to the number of partial photographing operations. The controller 2200 may partition the area between the top and bottom indicators 12S and 12E into regions of equal or unequal sizes.

The output unit 2100 may display the regions for partial photographing operations over the image 11.

Figure 13B:
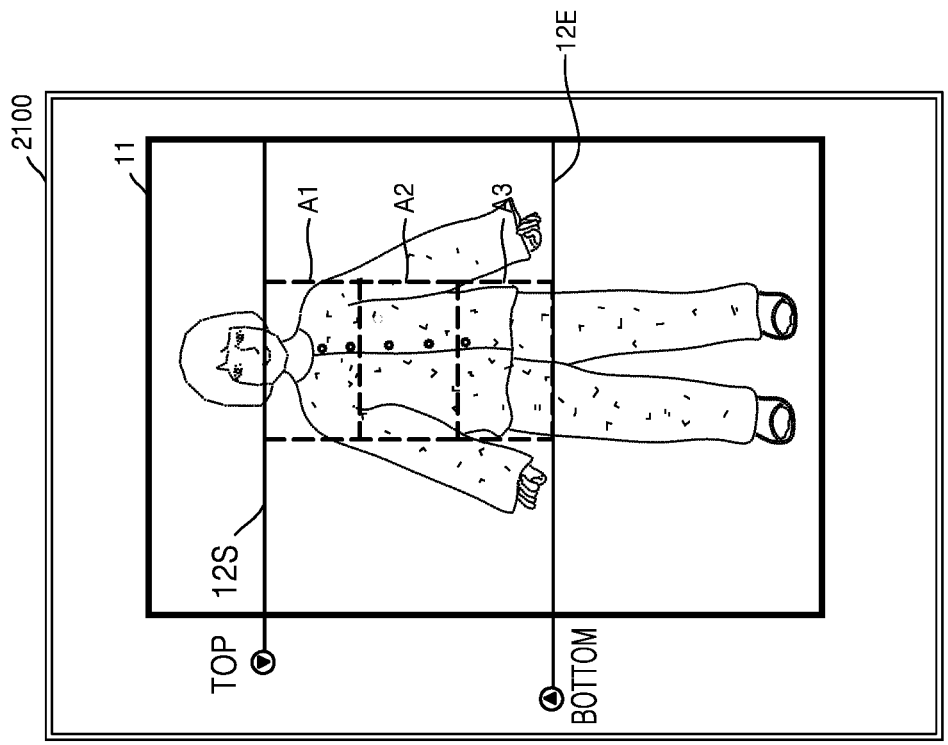
FIGS. 13A and 13B illustrate an example in which the medical imaging apparatus of FIG. 9 displays regions for partial photographing operations over an image.
Figure 13A:
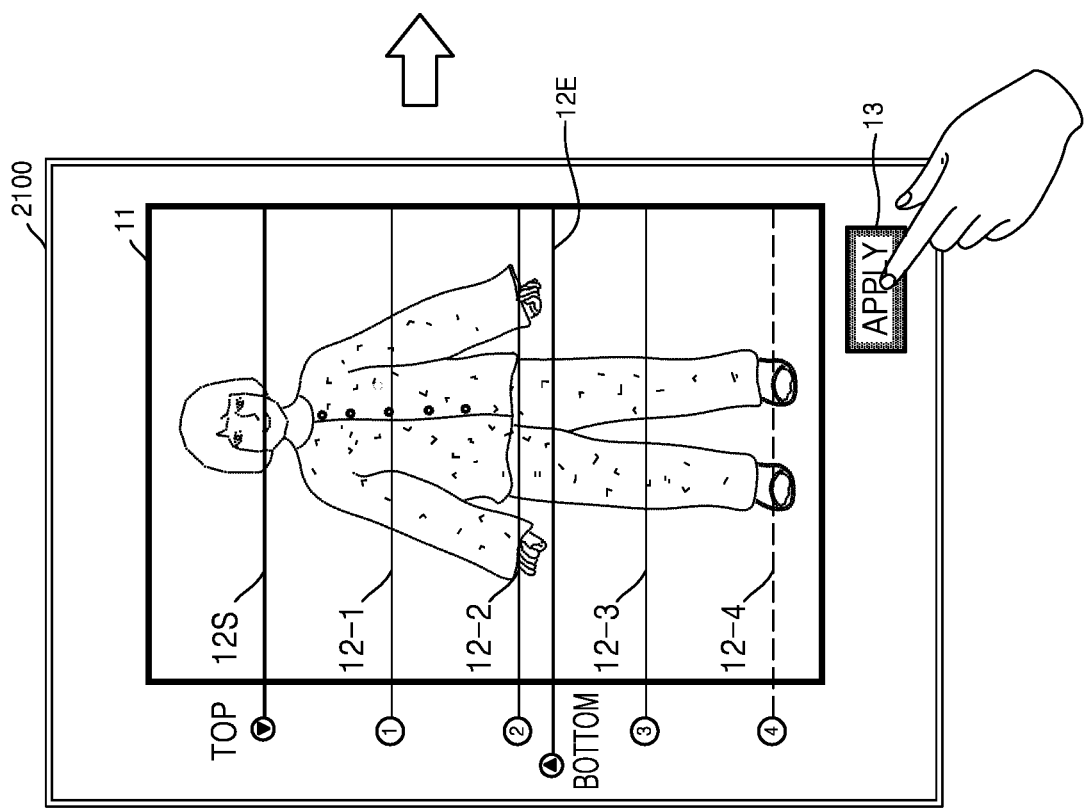

FIGS. 13A and 13B illustrate an example in which the medical imaging apparatus 2000 of FIG. 9 displays regions for partial photographing operations over an image 11.

Referring to FIG. 13A, a user may set positions of top and bottom indicators 12S and 12E in the image 11 displayed on the output unit 2100.

The output unit 2100 may further display a user interface (UI) 13 for applying settings of the top and bottom indicators 12S and 12E. The input unit 2300 may receive a user input for applying the settings of the top and bottom indicators 12S and 12E via the UI 13.

When settings of the top and bottom indicators 12S and 12E are applied according to a user input as shown in FIG. 13A, the output unit 2100 may display, over the image 11, first, second, and third regions A1, A2, and A3 into which an area to be X-rayed between the top and bottom indicators 12S and 12E is partitioned, as shown in FIG. 13B.

The user may intuitively and conveniently identify the first through third regions A1 through A3 via the output unit 2100. If the first through third regions A1 through A3 are determined to be appropriate, the user may input an irradiation command regarding radiation of X-rays.

The input unit 2300 may receive the irradiation command from the user. Upon receipt of the irradiation command, the controller 2200 may control an X-ray apparatus in order to perform partial photographing of the first through third regions A1 through A3.

Since the image 11 is registered geometrically, the controller 2200 may acquire positions in the real world that respectively correspond to the first, second, and third regions A1, A2, and A3 in the image 11 and control the X-ray apparatus to perform partial photographing operations on the first through third regions A1 through A3, respectively, according to the acquired positions in the real world.

The controller 2200 may adjust a collimator of the X-ray apparatus so that a region being irradiated with the X-rays corresponds to each of the first through third regions A1 through A3.

For example, the first through third regions A1 through A3 shown in FIG. 13B may respectively correspond to the first through third portions 683-1 through 683-3 of the object 10 described with reference to FIG. 5. The ROI 683 that is the sum of the first through third portions 683-1 through 683-3 as shown in FIG. 5 may correspond to the area to be X-rayed, which is between the top and bottom indicators 12S and 12E, as shown in FIG. 13B.

The controller 2200 may acquire three (3) partial X-ray images by performing partial photographing operations on the first through third regions A1 through A3, respectively. The controller 2200 may acquire a single X-ray image by stitching the three partial X-ray images together. In this aspect, a final X-ray image of the area between the top and bottom indicators 12S and 12E may be acquired. An example of stitching a plurality of partial X-ray images has been described above with reference to FIG. 6.

If the user determines that the first through third regions A1 through A3 are not appropriate via the output unit 2100 shown in FIG. 13B, the user may change a position of the top or bottom indicator 12S or 12E. In particular, the input unit 2300 may receive a user input for changing a position of the top or bottom indicator 12S or 12E. In this case, a screen of the output unit 2100 shown in FIG. 13B may be changed back to the screen shown in FIG. 13A, which causes a plurality of first through fourth guidelines 12-1 through 12-4 to be displayed again instead of the first through third regions A1 through A3 for partial photographing operations. Thus, the user may reset a top limit and a bottom limit for an area to be X-rayed by changing the position of the top or bottom indicator 12S or 12E.

FIG. 13B is an example in which the area between the top and bottom indicators 12S and 12E are equally partitioned into the first through third regions A1 through A3 (i.e., equally sized regions). As another example, the controller 2200 may partition the area between the top and bottom indicators 12S and 12E unequally into regions (i.e., regions that have different sizes). When the top and bottom indicators 12S and 12E are set as shown in FIG. 13A, the controller 2200 may divide the area between the top and bottom indicators 12S and 12E into three regions, i.e., a first region between the top indicator 12S and the first guideline 12-1, a second region between the first and second guidelines 12-1 and 12-2, and a third region between the second guideline 12-2 and the bottom indicator 12E. The controller 2200 may adjust the collimator so that an X-ray irradiation region may correspond to the first region during partial photographing of the first region. Similarly, the controller 2200 may adjust the collimator so that an X-ray irradiation region may correspond to the second region during partial photographing of the second region. The controller 2200 may adjust the collimator so that an X-ray irradiation region may correspond to the third region during partial photographing of the third region.

Figure 14:
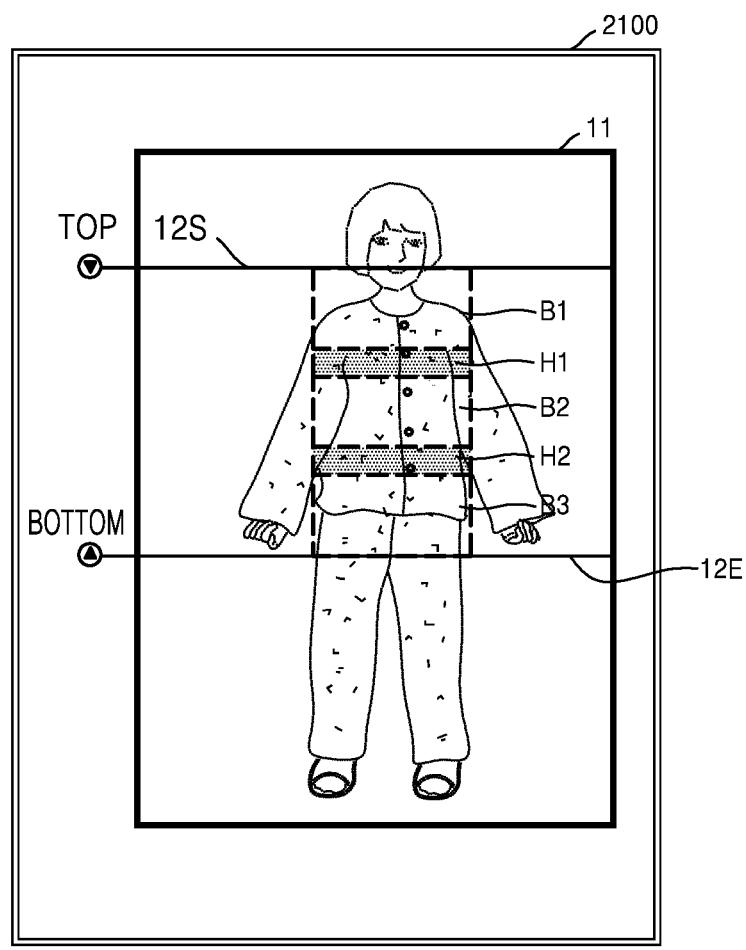
FIG. 14 illustrates another example in which the medical imaging apparatus of FIG. 9 displays regions for partial photographing operations over an image.

FIG. 14 illustrates another example in which the medical imaging apparatus 2000 of FIG. 9 displays regions for partial photographing operations over an image 11 obtained by photographing an object.

Referring to FIG. 14, the output unit 2100 may display the image 11 and then superimpose, over the image 11, first, second, and third regions B1. B2, and B3 for partial photographing operations, into which an area between the top and bottom indicators 12S and 12E is partitioned. The first and second regions B1 and B2 partially overlap each other, and the second and third regions B2 and B3 partially overlap each other.

As described above with reference to FIG. 5, adjacent ones of the first through third portions 683-1 through 683-3 of the object 10 to be partially photographed by the X-ray apparatus may overlap each other. This is because the X-ray image 783 that is a stitched image shown in FIG. 6 is acquired by combining together the overlapping portions S1 and S2 of the plurality of partial X-ray images 783-1 through 783-3.

According to an exemplary embodiment, the output unit 2100 may display, over the image 11, the first through third regions B1 through B3 for partial photographing operations, adjacent ones of which partially overlap each other, in the same manner as for the first through third portions 683-1 through 683-3 of the object 10 that partially overlap each other during partial photographing operations.

The output unit 2100 may highlight in the image 11 overlapping portions H1 and H2 between the first and second regions B1 and B2 and between the second and third regions B2 and B3. The output unit 2100 may highlight the overlapping portions H1 and H2 in various ways, such as, for example, by using different colors.

The overlapping portions H1 and H2 may be irradiated with X-rays twice during partial photographing operations and thus suffer excessive irradiation. Furthermore, the overlapping portions H1 and H2 respectively correspond to the overlapping portions (S1 and S2 of FIG. 6) between each of the partial X-ray images (783-1 through 783-3 of FIG. 6). The overlapping portions S1 and S2 may be distorted in the stitched X-ray image 783. Thus, image quality of the overlapping portions S1 and S2 in the X-ray image 783 may be degraded. In this aspect, image quality of a portion of the X-ray image 783 corresponding to the overlapping portions H1 and H2 highlighted in the image 11 may be degraded.

The user may intuitively conveniently identify the overlapping portions H1 and H2 during a partial photographing operation via the output unit 2100. The user may view the output unit 2100 to determine whether the overlapping portions H1 and H2 are important portions in an X-ray image that need to be protected from degradation of image quality and whether the overlapping portions H1 and H2 are portions that include sensitive organs, such as breasts, genital organs, etc. If the overlapping portions H1 and H2 are determined to be important portions in the X-ray image or include sensitive organs, the user may change a position of the top or bottom indicator 12S or 12E so as to change the overlapping portions H1 and H2. In this aspect, the input unit 2300 may receive a user input for changing the position of the top or bottom indicator 12S or 12E.

The controller 2200 may determine whether the overlapping portions H1 and H2 are portions including sensitive organs by analyzing the image 11. For example, the controller 2200 may estimate portions that include sensitive organs such as breasts, genital organs, etc. from the image 11. If the overlapping portions H1 and H2 are determined to be portions that include a sensitive organ, the controller 2200 may control the output unit 2100 to output a notification signal. The output unit 2100 may output a notification signal in any of various ways, e.g., by outputting a warning message to a screen thereof or warning sound to a speaker thereof.

When the output unit 2100 displays the first through third regions B1 through B3 on the image 11 as shown in FIG. 14, the input unit 2300 may receive an irradiation command from the user. When the irradiation command is received, the controller 2200 may control the X-ray apparatus to perform partial photographing operations on the first through third regions B1 through B3, respectively.

Referring back to FIGS. 13A and 13B, bottom limits for the first and second regions A1 and A2 among the first through third regions A1 through A3 for partial photographing operations does not coincide with the first and second guidelines 12-1 and 12-2, respectively. This is because each of the first through fourth guidelines 12-1 through 12-4 indicates a bottom limit for a maximum region for which an X-ray image is to be acquired according to the number of partial photographing operations. According to another exemplary embodiment, each of the first through fourth guidelines 12-1 through 12-4 may indicate a bottom limit for a region, which is obtained by equally partitioning an area between the top and bottom indicators 12S and 12E, rather than for a maximum area. In particular, according to an exemplary embodiment, the first through third guidelines 12-1 through 12-3 may be made coincident with bottom limits for the first through third regions A1 through A3, respectively, as described below with reference to FIGS. 15A, 15B, 16A, 16B, 17A, and 17B.

Figure 15A:
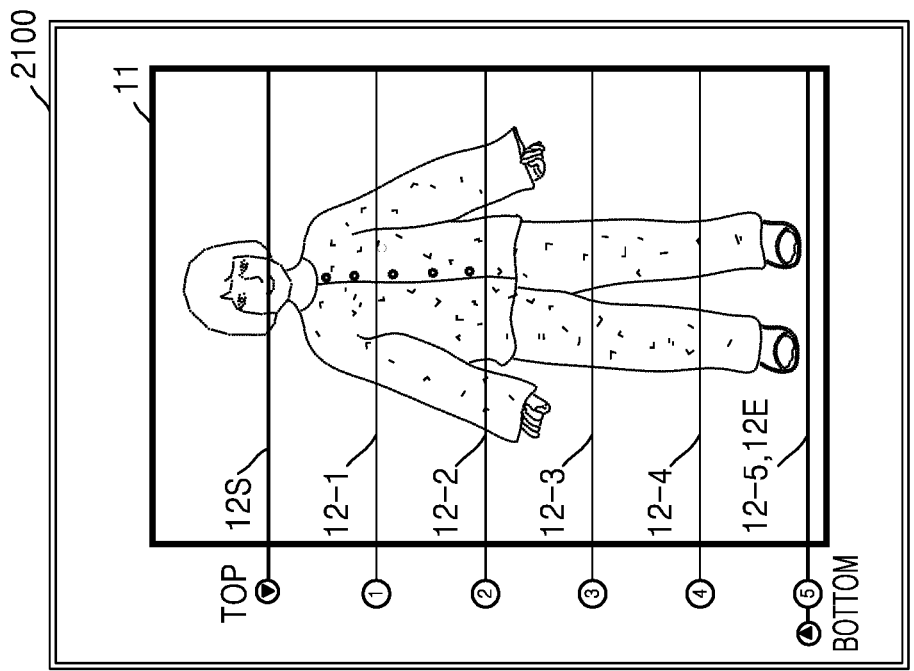
FIGS. 15A and 15B illustrate another example in which the medical imaging apparatus of FIG. 9 displays a top indicator and a plurality of guidelines over an image obtained by photographing an object.
Figure 15B:
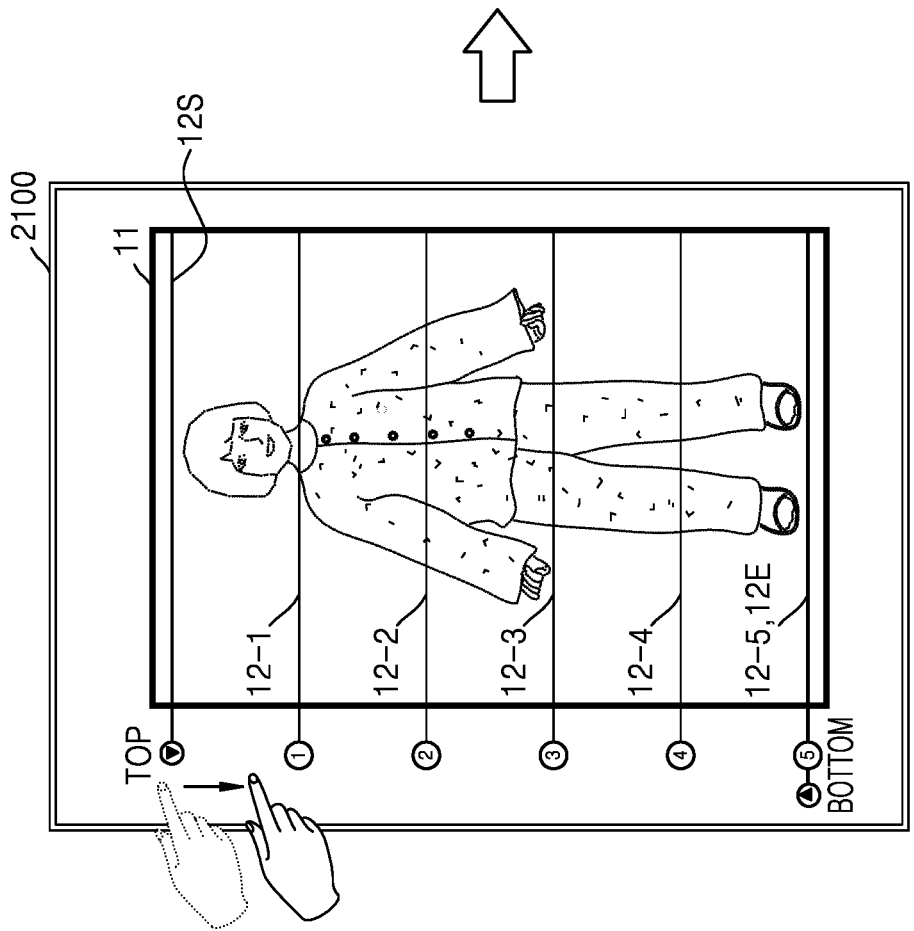

FIGS. 15A and 15B illustrate another example in which the medical imaging apparatus 2000 of FIG. 9 displays a top indicator 12S and a plurality of guidelines 12-1 through 12-5 over an image 11 obtained by photographing an object.

Referring to FIG. 15A, the output unit 2100 may display the top indicator 12S and the plurality of first through fifth guidelines 12-1 through 12-5. The output unit 2100 may further display a bottom indicator 12E on the image 11. The bottom indicator 12E may be the same as the fifth guideline 12-5 that is a last one of the first through fifth guidelines 12-1 through 12-5.

Each of the first through fifth guidelines 12-1 through 12-5 indicates a bottom limit for an area to be X-rayed according to the top indicator 12S and the number of partial photographing operations. Each of the first through fifth guidelines 12-1 through 12-5 may indicate a bottom limit for each of regions into which the area to be X-rayed between the top and bottom indicators 12S and 12E are equally partitioned according to the number of partial photographing operations.

Referring to FIG. 15A, an X-ray image of an area between the top and bottom indicators 12S and 12E may be acquired by performing a partial photographing operation five (5) times. The area between the top and bottom indicators 12S and 12E may be equally partitioned into five (5) regions, and each of the first through fifth guidelines 12-1 through 12-5 may indicate a bottom limit for each of the five regions.

The input unit 2300 may receive a user input for adjusting a position of the top indicator 12S. When the position of the top indicator 12S is adjusted according to a user input as shown in FIG. 15A, the output unit 2100 may display the first through fifth guidelines 12-1 through 12-5 that are changed according to the adjusted position of the top indicator 12S over the image 11, as shown in FIG. 15B. The output unit 2100 may display the changed first through fifth guidelines 12-1 through 12-5 over the image 11 in real-time as the position of the top indicator 12S is adjusted.

Referring to FIG. 15B, an X-ray image of the area between the top indicator 12S whose position has been changed and the bottom indicator 12E may still be acquired by performing a partial photographing operation five times. The area between the top indicator 12S whose position has been changed and the bottom indicator 12E may be equally partitioned into five (5) regions, and each of the first through fifth guidelines 12-1 through 12-5 may indicate a bottom limit for each of the five regions.

To control operation of the output unit 2100 as shown in FIGS. 15A and 15B, the controller 2200 may determine the number of partial photographing operations to be performed on the area between the top and bottom indicators 12S and 12E. The controller 2200 may determine a minimum number of partial photographing operations as the number of partial photographing operations. The controller 2200 may equally partition the area between the top and bottom indicators 12S and 12E in the image 11 into regions according to the determined number of partial photographing operations. The controller 2200 may control the first through fifth guidelines 12-1 through 12-5 to respectively indicate bottom limits for the regions in the image 11.

When the user adjusts the position of the top or bottom indicators 12S or 12E, the controller 2200 may change the number of partial photographing operations in real-time according to the adjusted position of the top or bottom indicators 12S or 12E, and accordingly change the first through fifth guidelines 12-1 through 12-5.

Figure 16B:
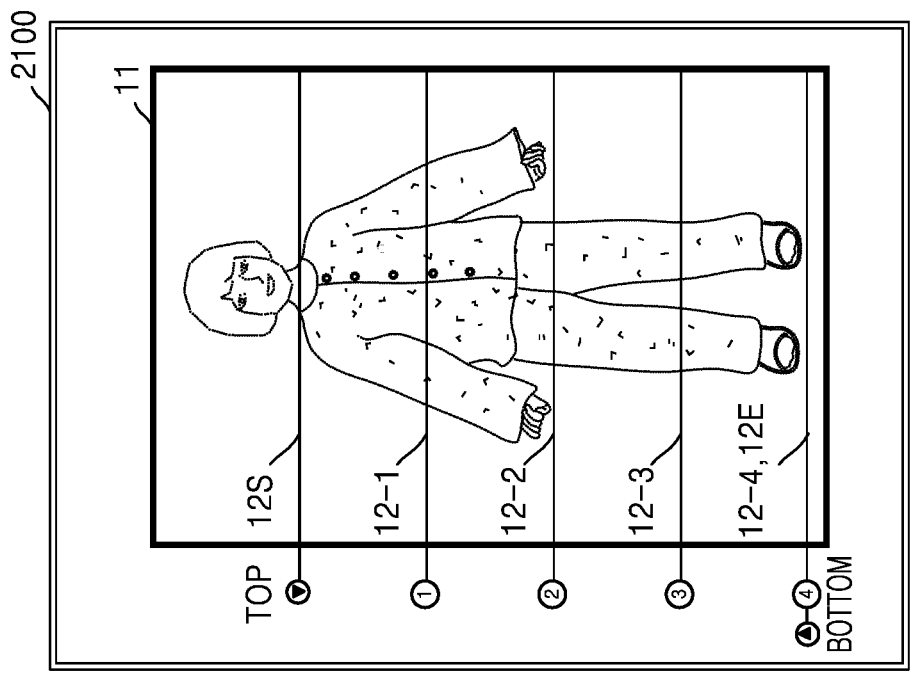
FIGS. 16A and 16B illustrate another example in which the medical imaging apparatus of FIG. 9 displays a top indicator and a plurality of guidelines over an image obtained by photographing an object.
Figure 16A:
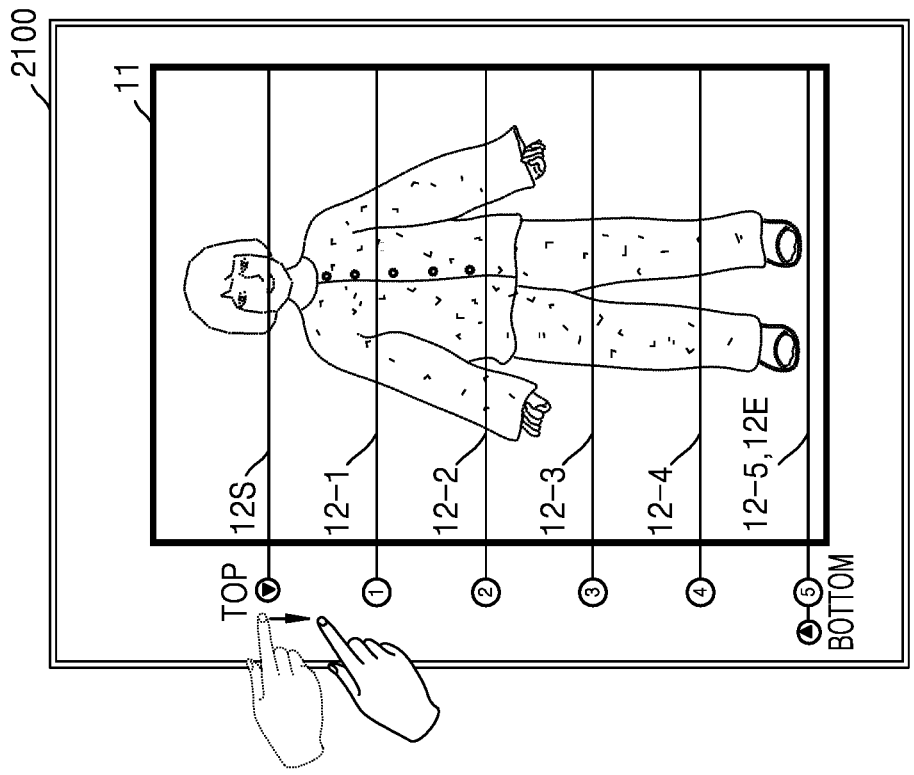

FIGS. 16A and 16B illustrate another example in which the medical imaging apparatus 2000 of FIG. 9 displays a top indicator 12S and a plurality of guidelines over an image 11 obtained by photographing an object;

When a position of the top indicator 12S according to a user input as shown in FIG. 16A, the output unit 2100 may display a plurality of guidelines 12-1 through 12-4 that are changed according to the adjusted position of the top indicator 12S on the image 11 as shown in FIG. 16B. The output unit 2100 may display the changed guidelines 12-1 through 12-4 over the image 11 in real-time as the position of the top indicator 12S is adjusted.

Referring to FIG. 16A, an X-ray image of an area between the top and bottom indicators 12S and 12E may be acquired by performing a partial photographing operation five (5) times. Conversely, referring to FIG. 16B, due to a change in position of the top indicator 12S, an X-ray image of an area between the top and bottom indicators 12S and 12E may be acquired by performing a partial photographing operation four (4) times. The area between the top indicator 12S whose position has been changed and the bottom indicator 12E may be equally partitioned into four (4) regions, and each of the first through fourth guidelines 12-1 through 12-4 may indicate a bottom limit for each of the four regions.

Figure 17B:
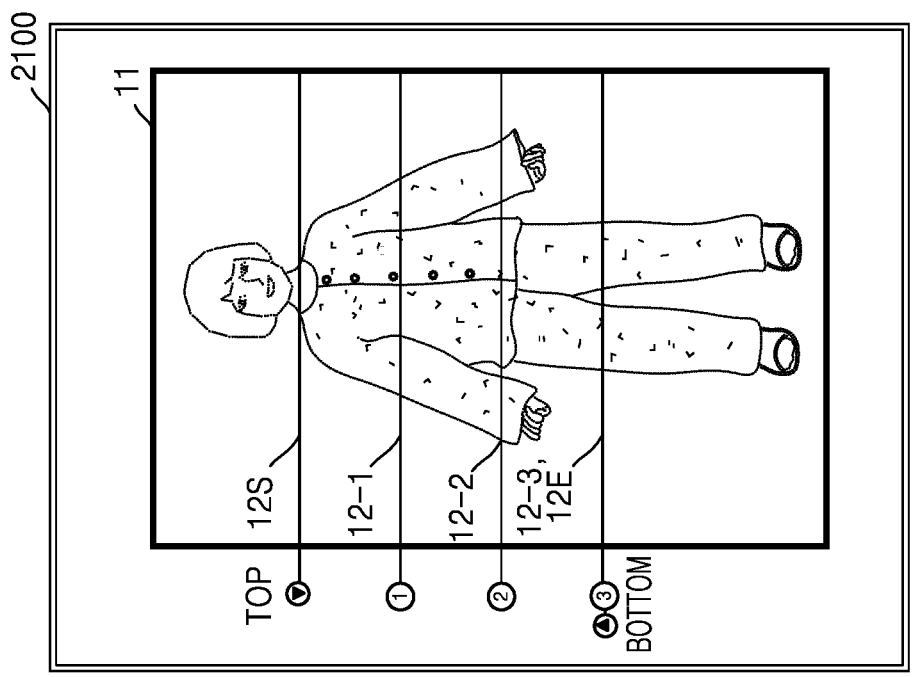
FIGS. 17A and 17B illustrate another example in which the medical imaging apparatus of FIG. 9 receives a user input for setting a bottom limit for an area to be X-rayed.
Figure 17A:
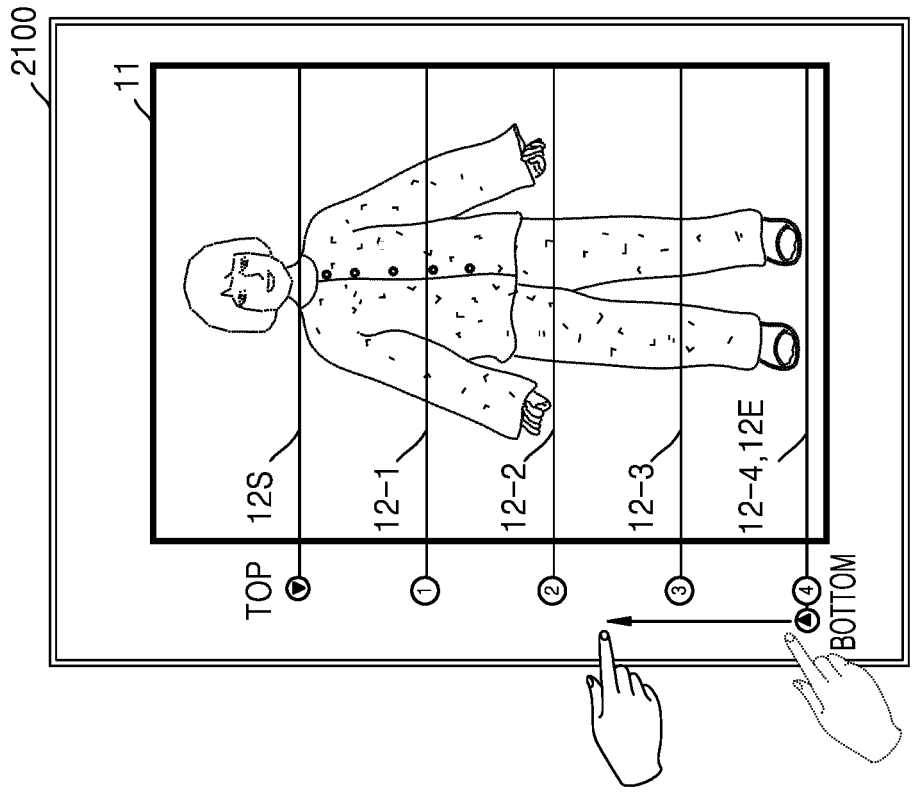

FIGS. 17A and 17B illustrate another example in which the medical imaging apparatus 2000 of FIG. 9 receives a user input for setting a bottom limit for an area to be X-rayed.

Referring to FIG. 17A, the input unit 2300 may receive a user input for adjusting a position of a bottom indicator 12E.

When the position of the bottom indicator 12E according to a user input as shown in FIG. 17A, the output unit 2100 may display a plurality of guidelines 12-1 through 12-3 that are changed according to the adjusted position of the bottom indicator 12E over the image 11 as shown in FIG. 17B. The output unit 2100 may display the changed guidelines 12-1 through 12-3 over the image 11 in real-time as the position of the bottom indicator 12E is adjusted.

Referring to FIG. 17B, an X-ray image of an area between a top indicator 12S and the bottom indicator 12E whose position has been changed may be acquired by performing a partial photographing operation three (3) times. The area between the top and bottom indicators 12S and 12E may be equally partitioned into three (3) regions, and each of the guidelines 12-1 through 12-3 may indicate a bottom limit for each of the three regions.

The medical imaging apparatus 2000 described above may be included in an X-ray apparatus or workstation. First, an example where the medical imaging apparatus 2000 is included in an X-ray apparatus is described.

Figure 18:
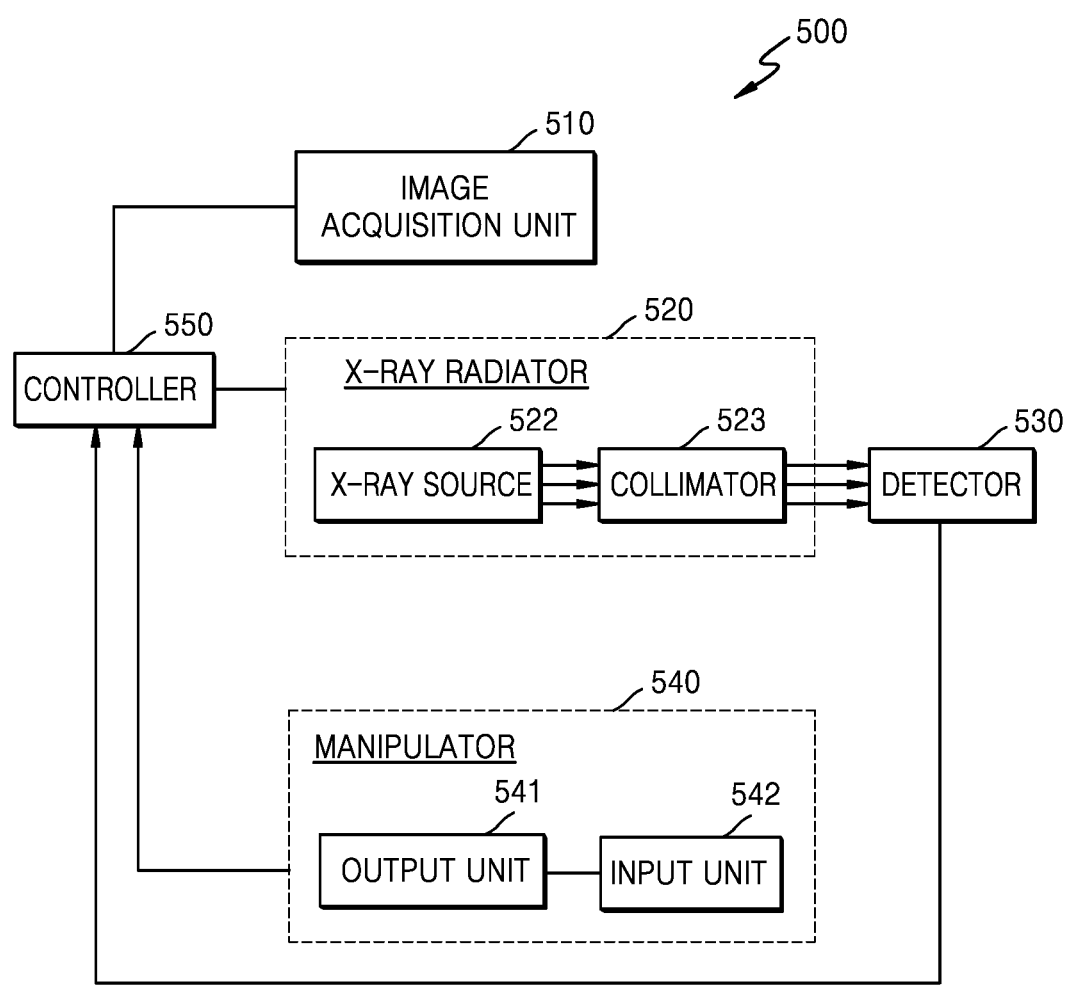
FIG. 18 is a block diagram of a configuration of an X-ray apparatus, according to an exemplary embodiment.

FIG. 18 is a block diagram of a configuration of an X-ray apparatus 500, according to an exemplary embodiment.

Referring to FIG. 18, the X-ray apparatus 500 according to the present exemplary embodiment may include an image acquisition unit (also referred to herein as an "image acquirer") 510, an X-ray radiator 520, a manipulator 540, and a controller 550. The X-ray apparatus 500 may further include a detector 530. Alternatively, the detector 530 may be an X-ray detector that is a separate device connectable to or disconnectable from the X-ray apparatus 500.

The X-ray radiator 520 may include an X-ray source 522 and a collimator 523. The manipulator 540 may include an output unit 541 and an input unit 542.

The image acquisition unit 510 may acquire an image of an object by photographing the object. The image acquisition unit 510 may be realized as a camera that is a general image acquisition device.

The image acquired by the image acquisition unit 510 may be a still image of the object or an image obtained by imaging the object in real-time.

The acquired image may be an image obtained by photographing the whole or a portion of the object. The portion of the object being photographed may correspond to an ROI for which an X-ray image is to be acquired or be slightly wider than the ROI.

Even if not expressly specified herein, the descriptions with respect to the X-ray apparatuses 100, 200, and 300 may be applied to the remaining components of the X-ray apparatus 500 other than the image acquisition unit 510. Furthermore, the X-ray apparatus 500 may be controlled by the workstation (110 of FIG. 1). In addition, the output unit 541, the controller 550, and the input unit 542 of the X-ray apparatus 500 may respectively correspond to the output unit 2100, the controller 2200, and the input unit 2300 of the medical imaging apparatus 2000. Thus, although omitted herein, the above descriptions with respect to the medical imaging apparatus 2000 may be applied to the X-ray apparatus 500 of FIG. 18.

The controller 550 may control the output unit 541 to display a top indicator for setting a top limit for an area to be X-rayed and at least one guideline over an image obtained by photographing an object. The at least one guideline indicates a bottom limit for the area to be X-rayed according to the top indicator and the number of partial photographing operations.

The above descriptions with respect to the output unit 2100 of the medical imaging apparatus 2000 may all be applied to the output unit 541, and thus, are not repeated.

Figure 19:
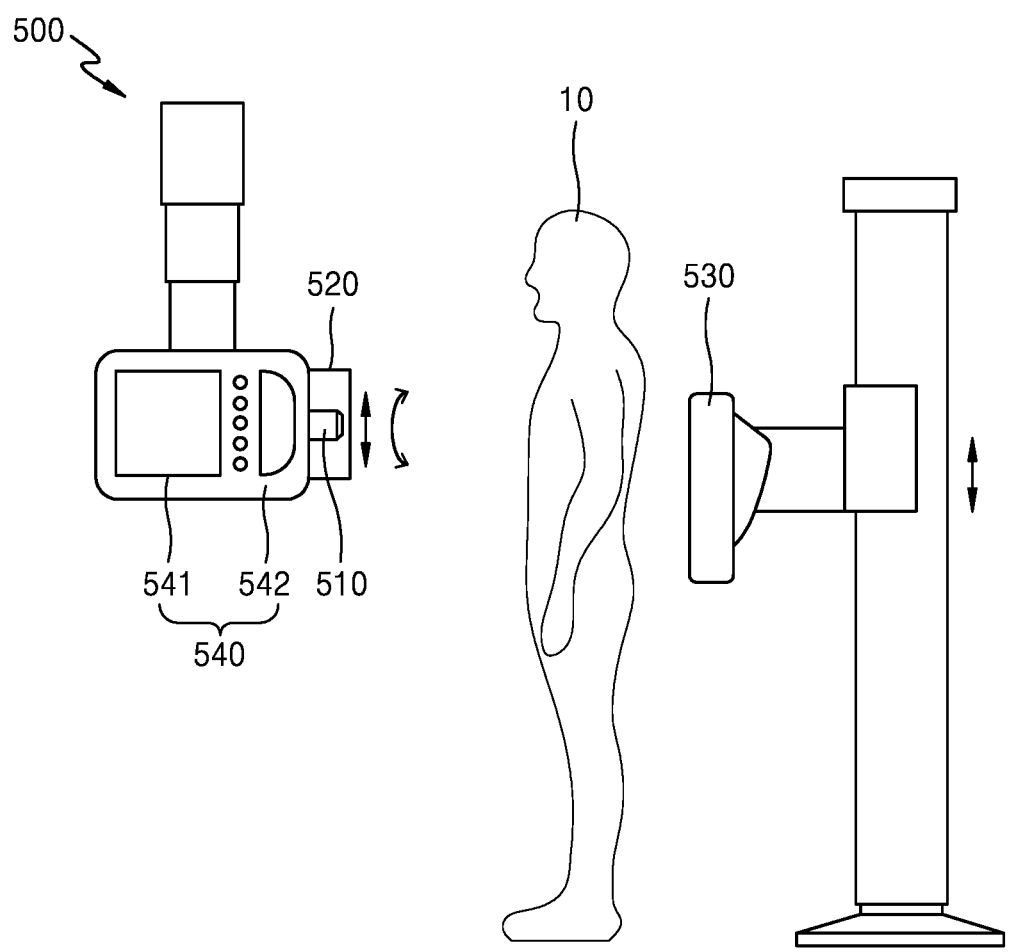
FIG. 19 illustrates an implementation of the X-ray apparatus of FIG. 18, according to an exemplary embodiment.

FIG. 19 illustrates an implementation of the X-ray apparatus 500 of FIG. 18, according to an exemplary embodiment.

Referring to FIG. 19, the image acquisition unit 510 acquires an image of an object 10 by photographing the object 10. Although FIG. 19 shows that the image acquisition unit 510 is disposed on a part of the X-ray radiator 520, exemplary embodiments are not limited thereto. The image acquisition unit 510 may be installed at any location where the object 10 may be photographed.

While FIG. 19 shows that the output unit 541 and the input unit 542 included in the manipulator 540 are separated from each other, exemplary embodiments are not limited thereto, and the input unit 542 or a portion of the input unit 542 may be disposed in the output unit 541. For example, if the input unit 542 includes a touch screen, the touch screen may be built into the output unit 541.

Figure 20A:
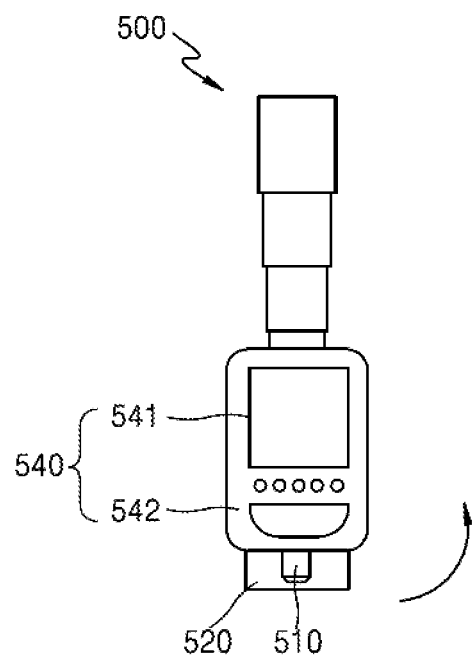
FIGS. 20A and 20B illustrate an example in which an X-ray radiator and a manipulator of the X-ray apparatus of FIG. 19 rotate.
Figure 20B:
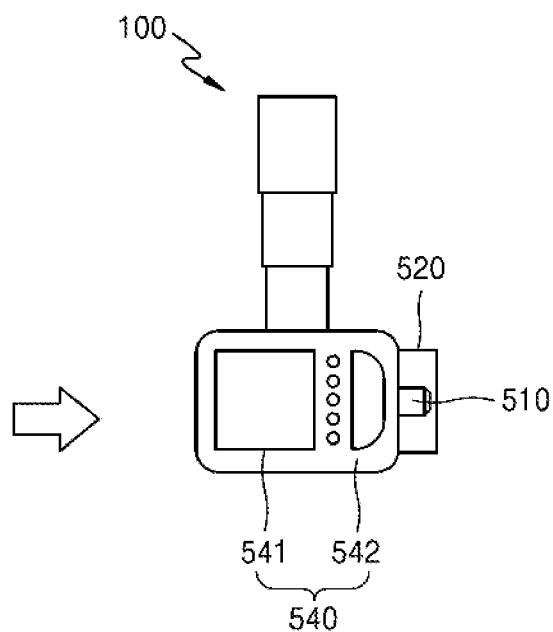

FIGS. 20A and 20B illustrate an example where the X-ray radiator 520 and the manipulator 540 of the X-ray apparatus 500 of FIG. 19 rotate.

Referring to FIG. 20A, the X-ray radiator 520 is rotatable. The X-ray radiator 520 may be rotated according to a position of an object. When the object lies on a table, the X-ray radiator 520 may face downwards, as shown in FIG. 20A. When the object stands up, the X-ray radiator 520 is directed sideways, as shown in FIG. 20B.

When the X-ray radiator 520 facing downwards as shown in FIG. 20A rotates 90 degrees in the counter-clockwise direction, the manipulator 540 may also rotate together with the X-ray radiator 520 as shown in FIG. 20B. Since the manipulator 540 of the X-ray apparatus 500 is attached to the X-ray radiator 520, the manipulator 540 may rotate together with the X-ray radiator 520.

Figure 21B:
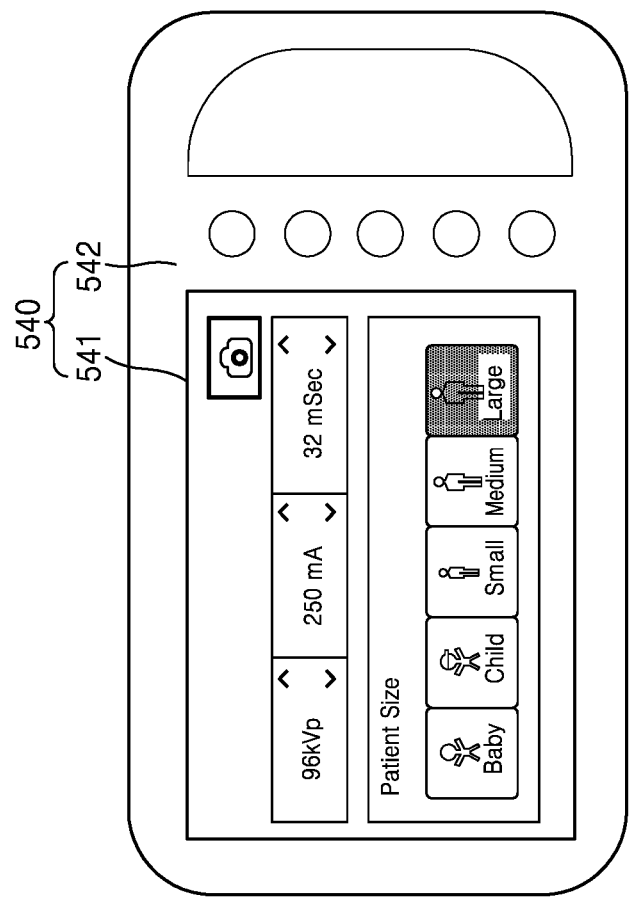
FIGS. 21A and 21B illustrate an example of a screen of an output unit when an X-ray radiator and a manipulator rotate as shown in FIGS. 20A and 20B.
Figure 21A:
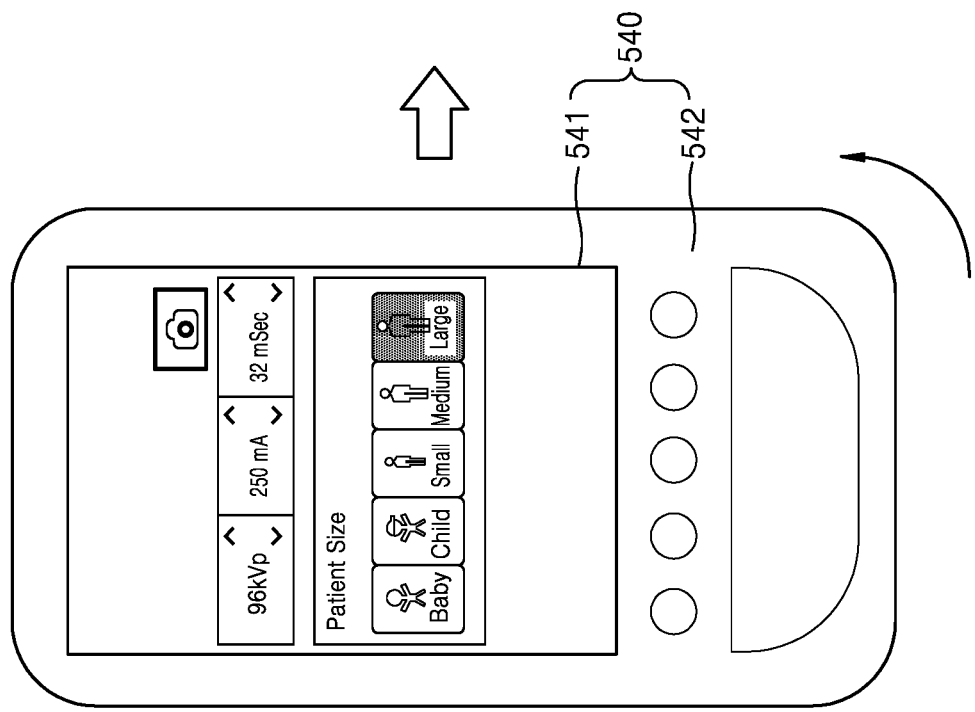

FIGS. 21A and 21B illustrate an example of a screen of the output unit 540 when the X-ray radiator 520 and the manipulator 540 rotate as shown in FIGS. 20A and 20B.

Referring to FIG. 21A, the screen of the output unit 541 is in a portrait mode. However, when the manipulator 540 rotates sideways, the screen of the output unit 541 may change to a landscape mode, as shown in FIG. 21B.

As shown in FIGS. 21A and 21B, the screen of the output unit 541 may change automatically to a portrait or landscape mode according to an orientation of the manipulator 540. This may eliminate user inconvenience in viewing the screen of the output unit 541.

Figure 22A:
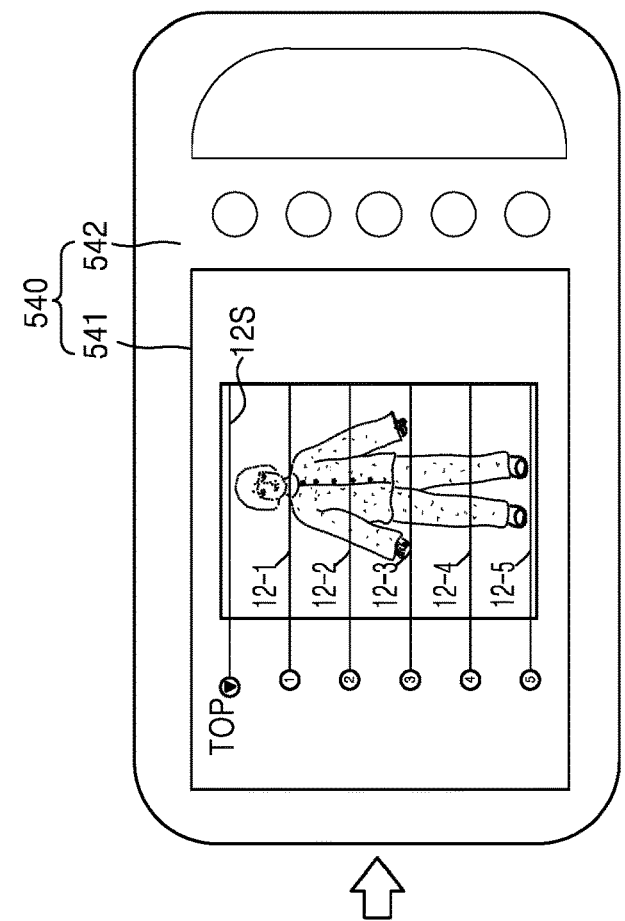
FIGS. 22A and 22B illustrate an example in which an output unit of an X-ray apparatus displays an image obtained by photographing an object.
Figure 22B:
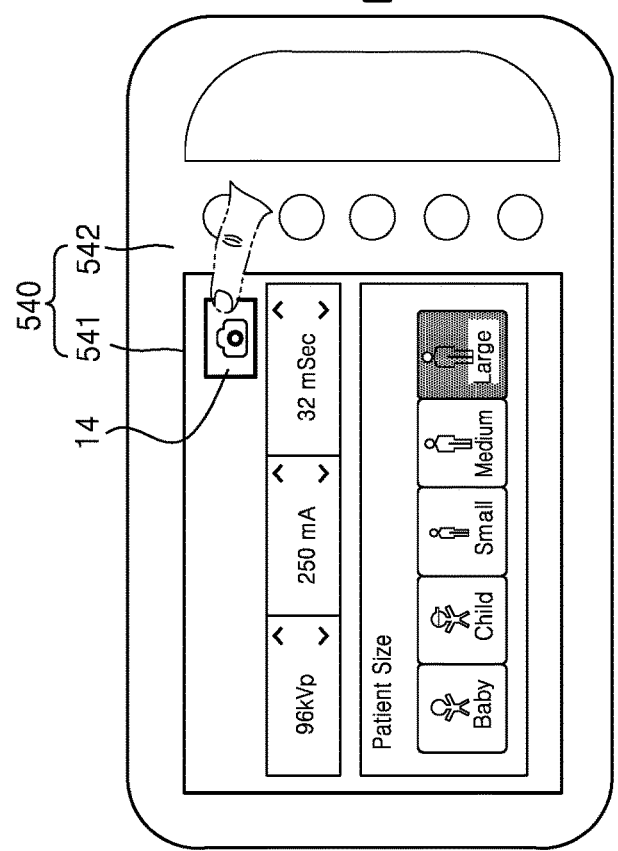

FIGS. 22A and 22B illustrate an example in which the output unit 541 of the X-ray apparatus 500 displays an image 11 obtained by photographing an object.

Referring to FIG. 22A, the output unit 541 may display a UI 14 for photographing the object. The input unit 542 may receive a user input that relates to an instruction for photographing of the object via the UI 14.

When the user input that relates to an instruction for photographing of the object is received as shown in FIG. 22A, the output unit 541 may display the image 11 obtained by photographing the object and then display a top indicator 12S and a plurality of guidelines 12-1 through 12-5 over the image 11, as shown in FIG. 22B.

The input unit 542 may receive a user input for adjusting a position of the top indicator 12S or a user input for setting a bottom limit for an area to be X-rayed. The user may set the area to be X-rayed by taking into account the optimal number of partial photographing operations that may prevent irradiation based on the top indicator 12S and the plurality of guidelines 12-1 through 12-5. When a top limit and a bottom limit for the area to be X-rayed have been set, the X-ray apparatus 500 may acquire an X-ray image by performing partial photographing operations on the object. The above descriptions with respect to the medical imaging apparatus 2000 may be applied to the X-ray apparatus 500, and thus, are not repeated. Furthermore, descriptions with respect to the output unit 541 of the X-ray apparatus 500 may also be applied to the output unit 2100 of the medical imaging apparatus 2000 of FIG. 7.

Examples in which the output unit 541 of the X-ray apparatus 500 of FIG. 18 displays a top indicator and a plurality of guidelines over an image obtained by photographing an object will now be described with reference to FIGS. 23, 24A, 24B, 25A, 25B, 26A, 26B, 27A, and 27B. Descriptions with respect to FIGS. 23, 24A, 24B, 25A, 25B, 26A, 26B, 27A, and 27B may also be applied to the medical imaging apparatus 2000 of FIG. 7.

Figure 23:
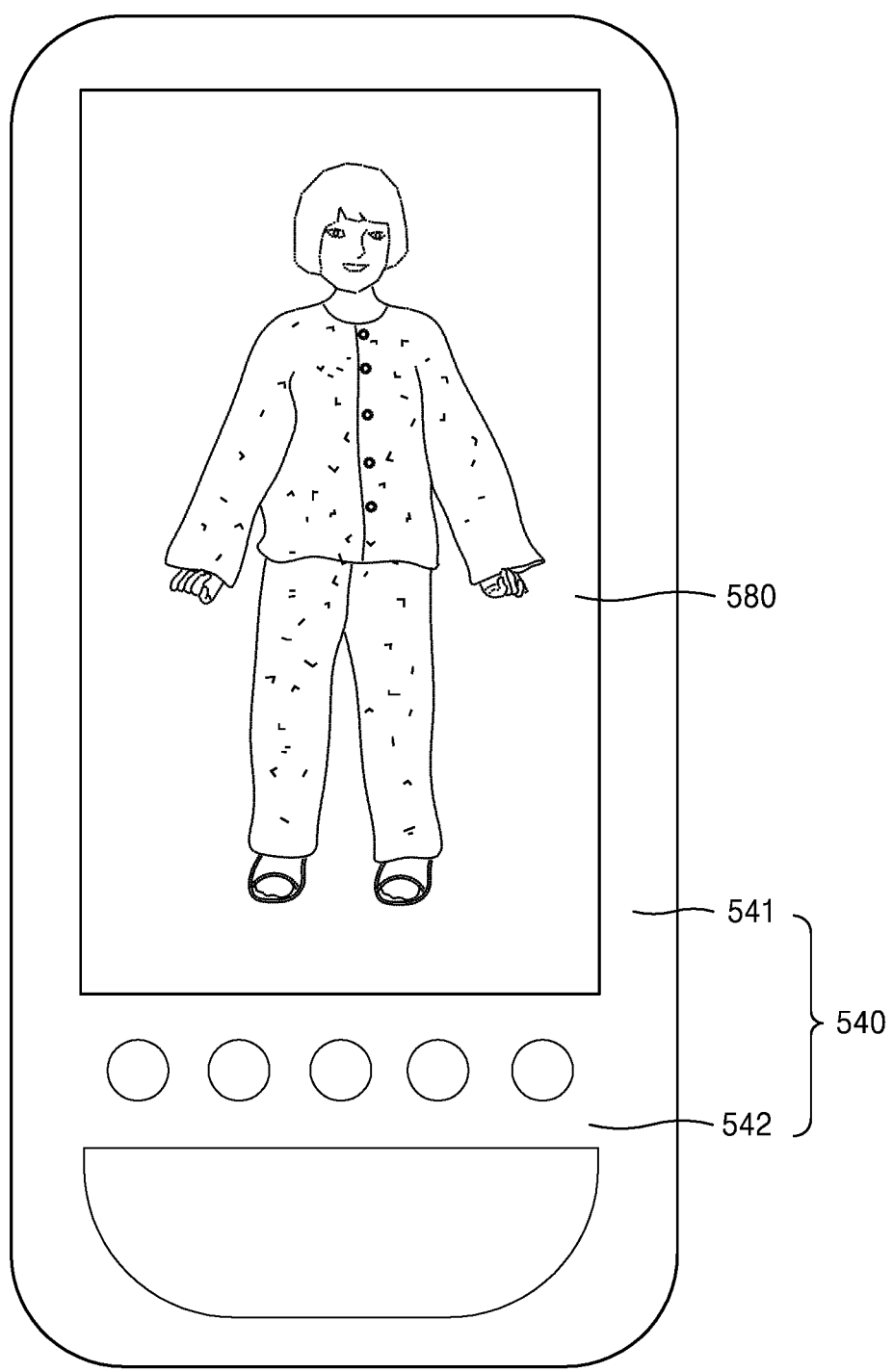
FIG. 23 is an example in which an X-ray apparatus displays an image obtained by photographing an object, according to an exemplary embodiment.

FIG. 23 is an example in which the X-ray apparatus 500 displays an image 580 obtained by photographing an object, according to an exemplary embodiment.

Referring to FIG. 23, the output unit 541 may display the image 580 obtained by photographing the object and acquired by the image acquisition unit 510.

Figure 24A:
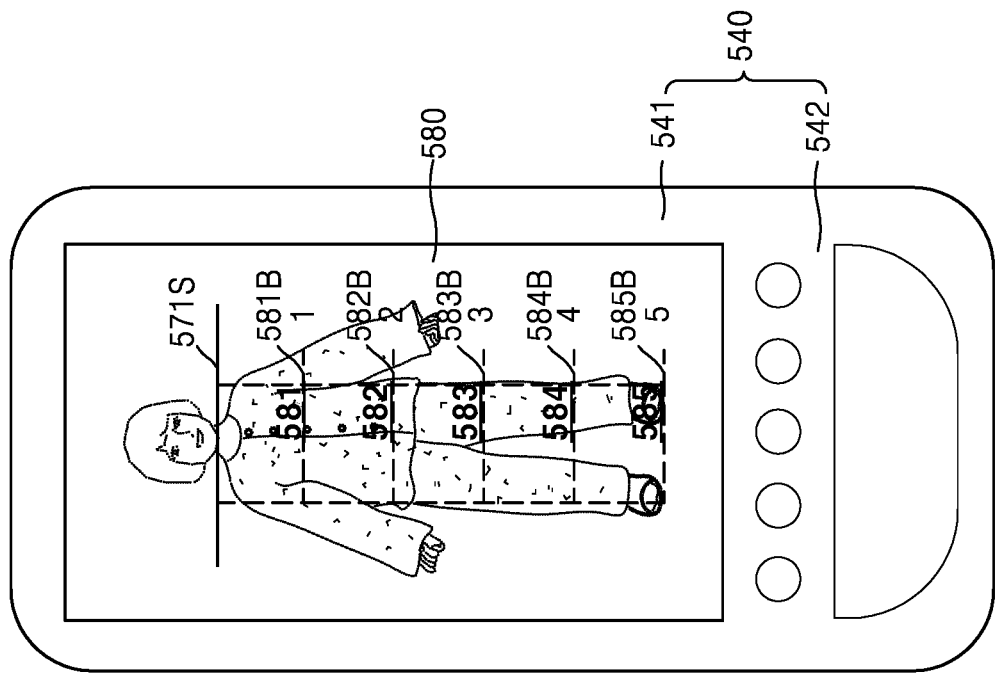
FIGS. 24A and 24B illustrates an example in which the X-ray apparatus receives a user input for setting a top limit for an area to be X-rayed and displays a top indicator and a plurality of guidelines over an image, according to an exemplary embodiment.
Figure 24B:
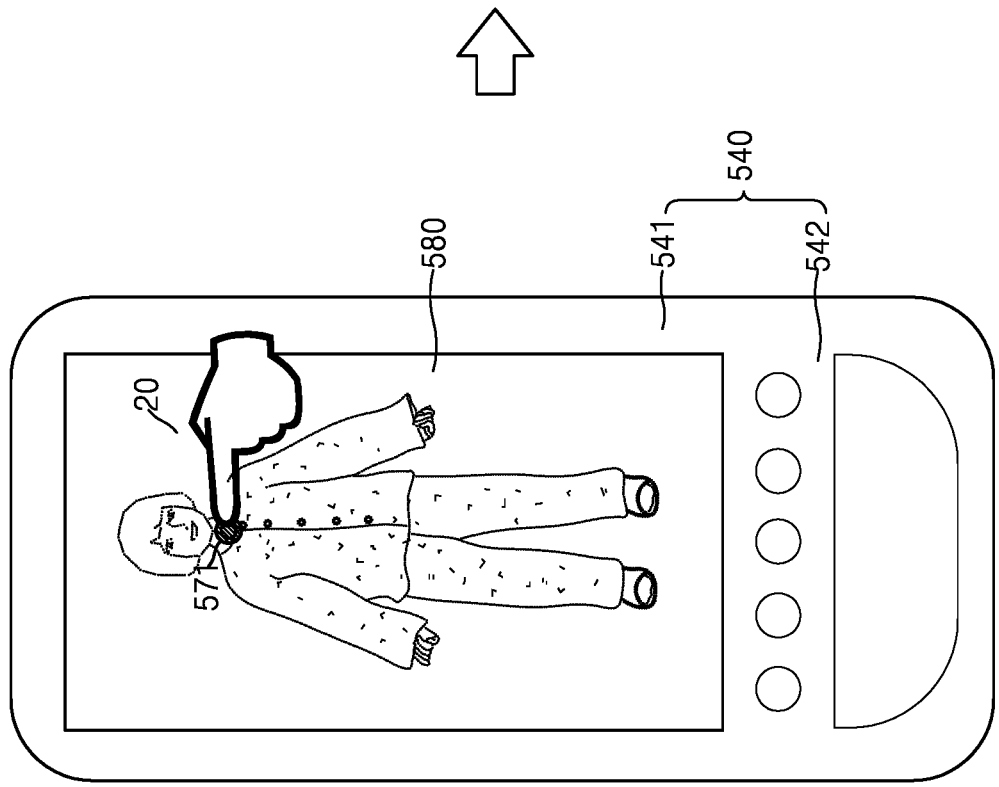

FIGS. 24A and 24B illustrate an example in which the X-ray apparatus 500 receives a user input for setting a top limit for an area to be X-rayed and displays a top indicator and a plurality of guidelines over an image, according to an exemplary embodiment.

Referring to FIG. 24A, the input unit 542 may receive a user input for setting a top limit 571 for an area to be X-rayed in an image 580 displayed on the output unit 541. The input unit 542 includes a touch screen, and a user 20 may set the top limit 571 for the area to be X-rayed by touching a location in the displayed image 580. FIG. 24A is merely an example, and the top limit 571 may be set in any of a variety of other ways.

When the user input for setting the top limit 571 for the area to be X-rayed is received as shown in FIG. 24A, the screen of the output unit 541 shown in FIG. 24 may change to a screen shown in FIG. 24B.

Referring to FIG. 24B, the output unit 541 may display, over the image 580, a top indicator 571S for setting a top limit for an area to be X-rayed and a plurality of first, second, third, fourth, and fifth guidelines 581B, 582B, 583B, 584B, and 585B. The top indicator 571S corresponds to a top limit 571 that is set by the user 20 for an area to be X-rayed. Each of the first, second, third, fourth, and fifth guidelines 581B, 582B, 583B, 584B, and 585B indicates a bottom limit for each of regions 581, 582, 583, 584, and 585 to be X-rayed according to the top indicator 571S and its corresponding number of partial photographing operations.

The output unit 541 may further display symbols identifying the number of partial photographing operations near the displayed plurality of guidelines 581B through 585B.

While FIG. 24B shows that numbers '1', '2', '3', '4', '5' are further displayed as the symbols, exemplary embodiments are not limited thereto.

Each of the regions 581 through 585 to be X-rayed is determined based on the top indicator 571S and its corresponding number of partial photographing operations. Each of the regions 581 through 585 to be X-rayed is located between the top indicator 571S and a corresponding one of the first through fifth guidelines 581B through 585B.

The region 581 to be X-rayed between the top indicator 571S and the first guideline 581B corresponds to an X-ray image that may be acquired by performing a single X-ray photographing operation. The region 582 to be X-rayed between the top indicator 571S and the second guideline 582B corresponds to an X-ray image that may be acquired by performing an X-ray photographing operation twice. The region 583 to be X-rayed between the top indicator 571S and the third guideline 583B corresponds to an X-ray image that may be acquired by performing an X-ray photographing operation three times. The region 584 to be X-rayed between the top indicator 571S and the fourth guideline 584B corresponds to an X-ray image that may be acquired by performing an X-ray photographing operation four times. The region 585 to be X-rayed between the top indicator 571S and the fourth guideline 585B corresponds to an X-ray image that may be acquired by performing an X-ray photographing operation five times.

Although FIG. 24B shows that the first though fifth guidelines 581B through 585B are displayed over the image 11, if an X-ray image of a region extending down from the top indicator 571S is acquired by performing a single partial photographing operation, the output unit 541 may display only a single guideline over the image 580. Hereinafter, even if the following figures show that the output unit 541 displays a plurality of guidelines, it is to be noted that this does not preclude a case where the output unit 541 displays only a single guideline.

While FIG. 24B shows that the five (the first through fifth) guidelines 581B through 585B are displayed over the image 580, the number of guidelines displayed over the image 580 is not limited to five (5). FIG. 24 is merely an example, and the number of guidelines being displayed may vary according to exemplary embodiments. For example, the number of guidelines being displayed may vary based on a relationship of correspondence between an object depicted in the image 580 and a real-world object, a position of the top indicator 571S, etc. Alternatively, a maximum number of guidelines being displayed may be set by default, or may be set or reset by the user 20.

Referring to FIGS. 24A and 24B, when the input unit 542 receives a user input for setting the top limit 571 for an area to be X-rayed, the output unit 541 may display, over the image 580, the top indicator 571S corresponding to the top limit 571 and the first through fifth guidelines 581B through 585B. Referring back to FIG. 8 for comparison, the output unit 2100 may display the top indicator 12S over the image 11 immediately without receiving a user input for setting a top limit for an area to be X-rayed. The output unit 2100 may automatically display the top indicator 12S on an uppermost portion of the image 11.

Figure 25A:
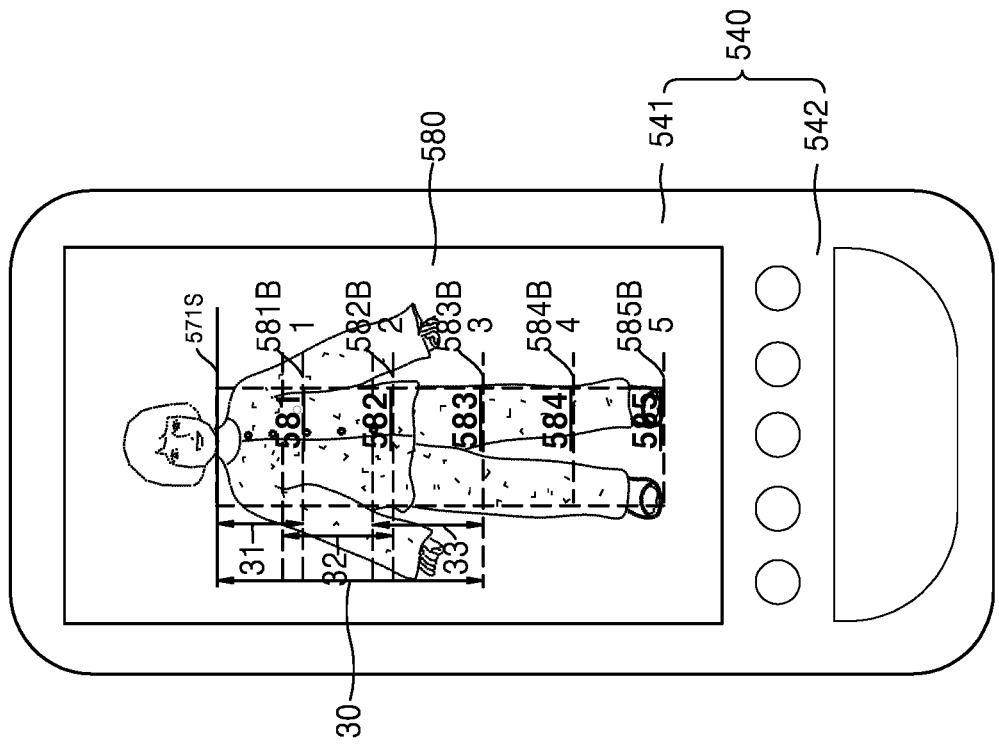
FIGS. 25A and 25B illustrate an example in which an X-ray apparatus receives a user input for setting a bottom limit for an area to be X-rayed and displays regions for partial photographing operations over an image, according to an exemplary embodiment.
Figure 25B:
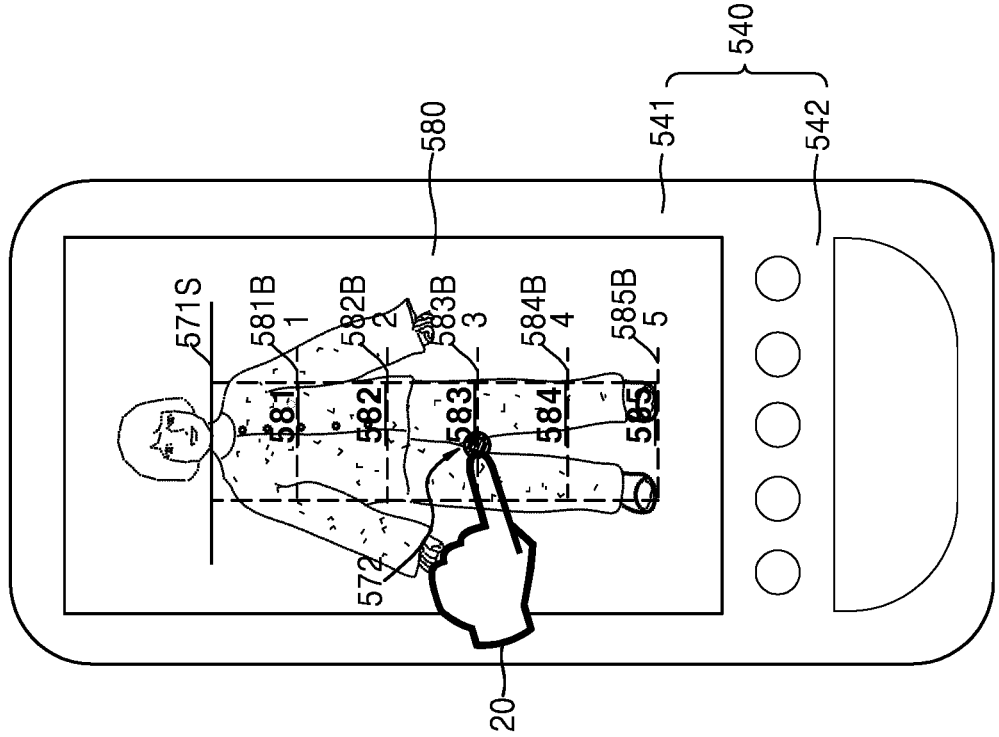

FIGS. 25A and 25B illustrate an example in which the X-ray apparatus 500 receives a user input for setting a bottom limit for an area to be X-rayed and displays regions for partial photographing operations over an image, according to an exemplary embodiment.

Referring to FIG. 25A, the input unit 542 may receive a user input for setting a bottom limit 572 for an area to be X-rayed. The input unit 542 includes a touch screen, and a user 20 may set the bottom limit 572 for the area to be X-rayed by touching a location in an image 580 displayed on the output unit 541. The bottom limit 572 shown in FIG. 25A may be a point in a third guideline 583B. An X-ray image of an area between the top indicator 571S and the bottom limit 572 in the image 580 may be acquired by performing a partial photographing operation three times.

FIG. 25A is merely an example of setting the bottom limit 572, and the bottom limit 572 may be set in any of a variety of other ways. As another example, the bottom limit 572 may be set by selecting one of first through fifth guidelines 581B through 585B. Alternatively, the bottom limit 572 may be set by selecting the number of partial photographing operations. For example, if the user inputs information for selecting the number of partial photographing operations as being two (2), the bottom limit 572 may be determined as being a second guideline 582B.

When the bottom limit 572 for the area to be X-rayed is set as shown in FIG. 25A, the X-ray apparatus 500 may perform a partial photographing operation of the area between the top indicator 571S and the bottom limit 572 three times, thereby acquiring an X-ray image of the area therebetween.

The X-ray apparatus 500 may change a screen of the output unit 541 shown in FIG. 25A to a screen shown in FIG. 25B before performing partial photographing operations so that the user 20 may identify regions for the partial photographing operations.

Referring to FIG. 25B, the output unit 541 may display, over the image 580, first, second, and third regions 31, 32, and 33 for each partial photographing operation and which are obtained by partitioning an area 30 between the top indicator 571S and the bottom limit 572.

The first, second, and third regions 31, 32, and 33 for partial photographing operations respectively correspond to regions to be photographed during each partial photographing operation. The first and second regions 31 and 32 may overlap each other, and the second and third regions 32 and 33 may overlap each other. The output unit 541 may display the first, second, and third regions 31, 32, and 33, adjacent ones of which partially overlap each other, over the image 580.

However, after viewing the image 580 displayed on the output unit 541 as shown in FIG. 24B, the user 20 may adjust a position of the top indicator 571S instead of setting the bottom limit 572 for an area to be X-rayed as shown in FIG. 25A.

Figure 26A:
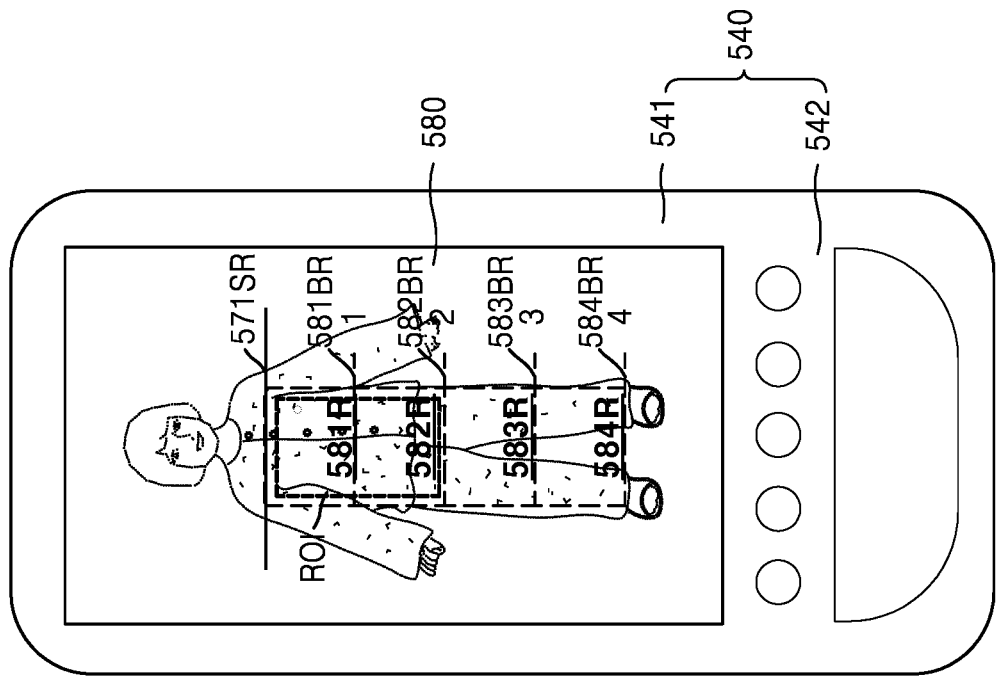
FIGS. 26A and 26B illustrate an example in which an X-ray apparatus receives a user input for adjusting a top indicator and displays the adjusted top indicator and a changed plurality of guidelines over an image.
Figure 26B:
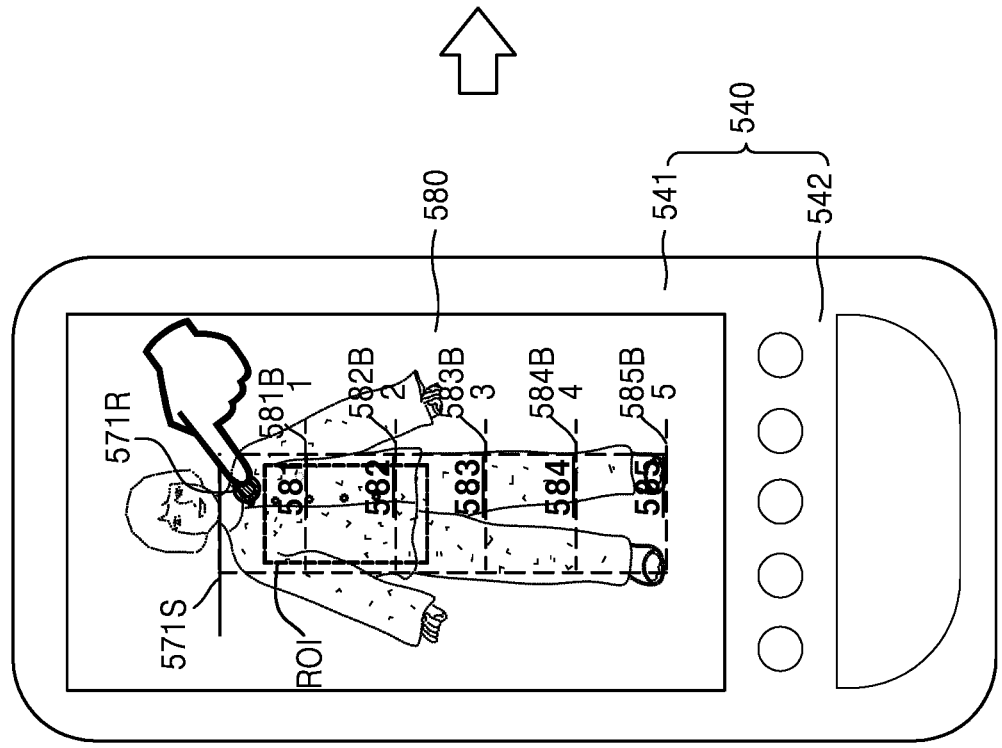

FIGS. 26A and 26B illustrate an example in which the X-ray apparatus 500 receives a user input for adjusting a top indicator and displays the adjusted top indicator and a changed plurality of guidelines over an image.

Referring to FIG. 26A, an ROI for which a user desires to acquire an X-ray image may be positioned between a top indicator 571S and a third guideline 583B. Thus, the X-ray image of the ROI may be acquired by performing a partial photographing operation three times. However, if the user determines that a partial photographing operation is performed more than necessary compared to a size of the ROI, the user may adjust a position of the top indicator 571S. In this aspect, the input unit 542 may receive a user input for adjusting the position of the top indicator 571S.

The input unit 542 may receive a user input for adjusting the position of the top indicator 571S by using any of various methods. For example, the input unit 542 may receive a user input for moving the top indicator 571S via a drag. As another example, the input unit 542 may receive a user input for adjusting the position of the top indicator 571S by receiving a user's touch on a point 571R. Alternatively, the input unit 542 may receive a user input for removing the top indicator 571S and first through fifth guidelines 581B through 585B displayed over the image 580 and then a user input for resetting a top limit for an area to be X-rayed (see, for example, FIGS. 24A and 24B).

When the input unit 542 receives a user input for adjusting the position of the top indicator 571S as shown in FIG. 26A, the X-ray apparatus 500 may change a screen of the output unit 541 shown in FIG. 26A to a screen shown in FIG. 26B.

Referring to FIG. 26B, the output unit 541 may display, over the image 580, a plurality of guidelines 581BR, 582BR, 583BR, and 584BR that are changed according to an adjusted top indicator 571SR. An ROI may be positioned between the adjusted top indicator 571SR and the changed second guideline 582BR. An X-ray image of the ROI may be acquired by performing partial photographing operations twice. The number of partial photographing operations necessary for acquiring the X-ray image of the ROI may be reduced compared to the number of partial photographing operations in FIG. 26A.

As described above, according to an exemplary embodiment, the X-ray apparatus 500 is configured to receive a user input for setting or resetting the position of the top indicator 571S for setting a top limit for an area to be X-rayed and display at least one of the first through fifth guidelines 581B through 585B according to the top indicator 571S. This configuration allows the user to select the optimal number of partial photographing operations according to a size of the ROI, thereby preventing excessive X-ray irradiation on an object.

FIGS. 27A and 27B illustrate another example in which the X-ray apparatus 500 receives a user input for setting a bottom limit for an area to be X-rayed and displays regions for partial photographing operations over an image.

Referring to FIG. 27A, the input unit 542 may receive a user input for setting a bottom limit 572 for an area to be X-rayed. The bottom limit 572 shown in FIG. 27A may be a point between second and third guidelines 582B and 583B.

An X-ray image of an area between the top indicator 571S and the bottom limit 572 in the image 580 may be acquired by performing a partial photographing operation three times. As shown in FIG. 27A, a user 20 may set the bottom limit 572 for an area to be X-rayed by touching the bottom limit 572. However, this is merely an example, and the bottom limit 572 may be set in any of a variety of other ways.

When the bottom limit 572 for the area to be X-rayed is set as shown in FIG. 27A, the X-ray apparatus 500 may acquire an X-ray image of the area between the top indicator 571S and the bottom limit 572 by performing a partial photographing operation three times. The X-ray image of the area between the top indicator 571S and the bottom limit 572 may be obtained. The X-ray apparatus 500 may change a screen of the output unit 541 shown in FIG. 27A to a screen shown in FIG. 27B before performing partial photographing operations so that the user 20 may identify regions for the partial photographing operations.

Referring to FIG. 27B, the output unit 541 may display, over the image 580, first, second, and third regions 41, 42, and 43 for partial photographing operations and which are obtained by partitioning an area 40 between the top indicator 571S and the bottom limit 572.

The first, second, and third regions 41, 42, and 43 for partial photographing operations respectively correspond to regions to be photographed during each partial photographing operation. The first and second regions 41 and 42 may overlap each other, and the second and third regions 42 and 43 may overlap each other. The output unit 541 may display the first, second, and third regions 41, 42, and 43, adjacent ones of which partially overlap each other, over the image 580.

The X-ray apparatus 500 may adjust the collimator 523 so that an X-ray irradiation region corresponds to each of the first, second, and third regions 41, 42, and 43 for partial photographing operations.

Adjusting the collimator 523 of the X-ray apparatus 500 according to an exemplary embodiment will now be described with reference to FIGS. 28A and 28B.

Figure 28B:
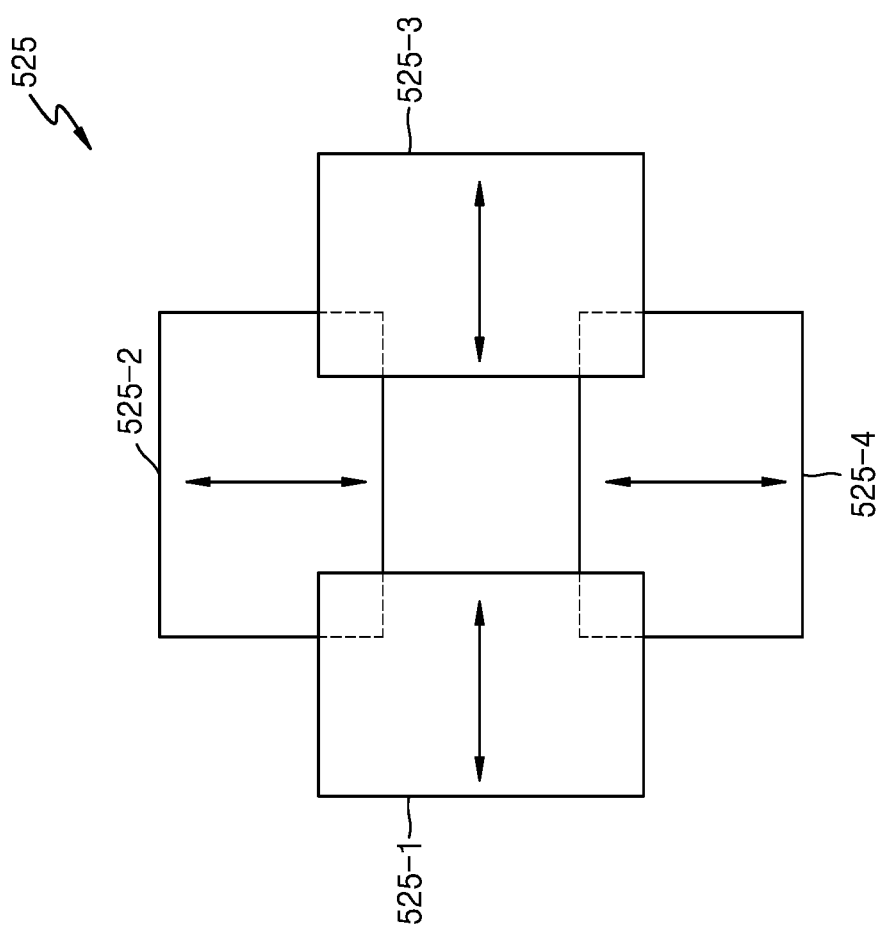
FIGS. 28A and 28B illustrate an example of an X-ray radiator included in the X-ray apparatus of FIG. 18.
Figure 28A:
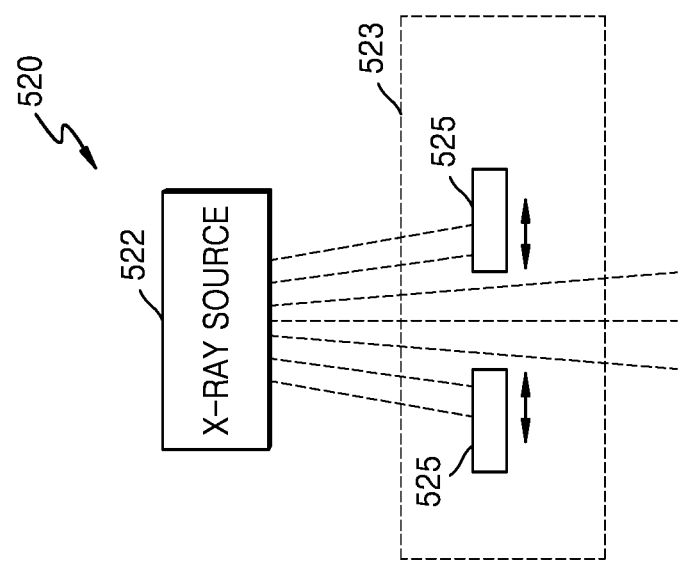

FIGS. 28A and 28B illustrate an example of the X-ray radiator 520 included in the X-ray apparatus 500 of FIG. 18.

Referring to FIG. 28A, the X-ray radiator 520 may include the X-ray source 522 and the collimator 523. The collimator 523 may include at least one blade 525. The collimator 523 may adjust a size and a position of an aperture of the collimator 523 via movement of the at least one blade 525. The collimator 523 may adjust a region being irradiated with X-rays emitted by the X-ray source 522 (i.e., an X-ray irradiation region) via an adjustment of the aperture of the collimator 523.

The collimator 523 may further include a lamp. When the lamp is turned on, light is emitted through the aperture of the collimator 523 so that the user may identify the X-ray irradiation region via the light.

FIG. 28B is an example of a plurality of blades 525, i.e., 525-1, 525-2, 525-3, and 525-4 included in the collimator 523. The blades 525-1, 525-2, 525-3, and 525-4 may move independently with respect to one another.

The output unit 541 of the X-ray apparatus 500 of FIG. 18 may display a top indicator and at least one guideline over an image obtained by photographing an object. The controller 550 may set a top limit and a bottom limit for an area to be X-rayed according to a user input. The controller 550 may then determine the number of partial photographing operations and partition the area to be X-rayed into regions (A1, A2, and A3 of FIG. 13 or B1, B2, and B3 of FIG. 14) for partial photographing operations according to the determined number of partial photographing operations. During partial photographing of each of the regions, the controller 550 may adjust the blades 525-1, 525-2, 525-3, and 525-4 of the collimator 523 so that a region being irradiated with X-rays emitted by the X-ray radiator 520 (i.e., an X-ray irradiation region) may correspond to each of the regions.

While it has been described that the medical imaging apparatus 2000 is included in the X-ray apparatus 500, the medical imaging apparatus 2000 may also be included in the workstation. Next, an example where the medical imaging apparatus 2000 is included in the workstation is described.

Figure 29:
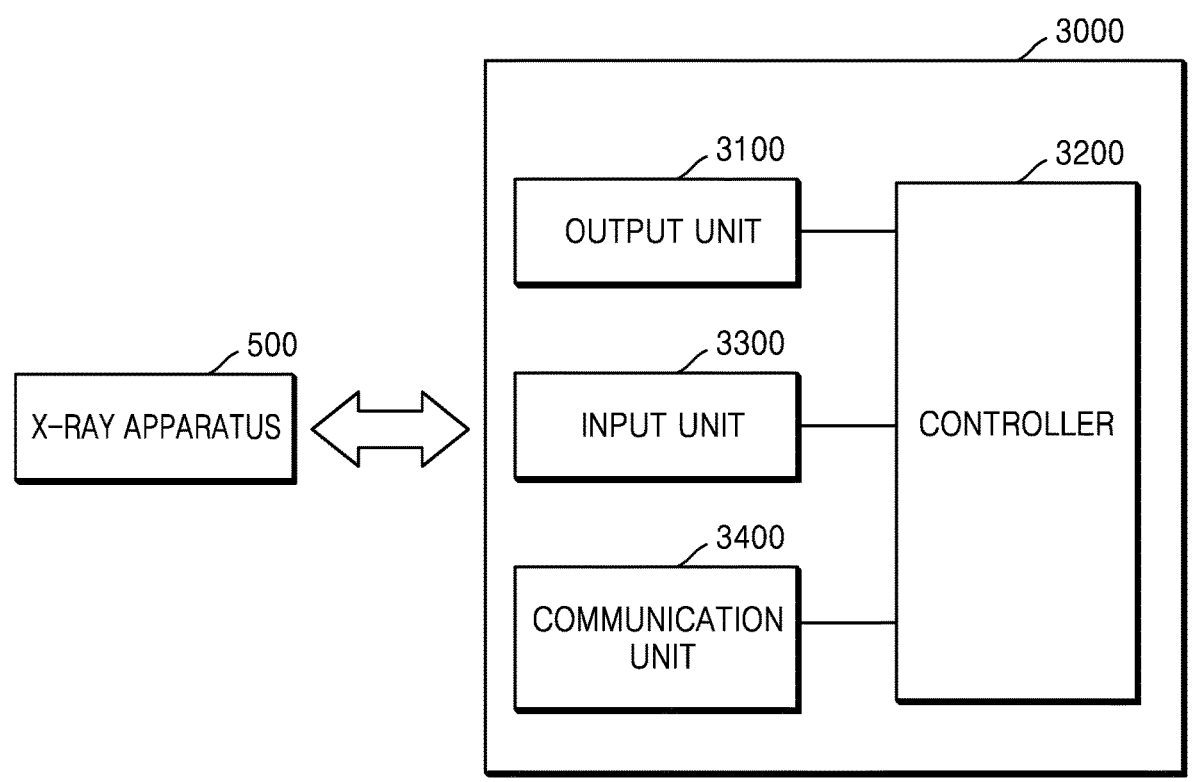
FIG. 29 is a block diagram of a configuration of a workstation, according to an exemplary embodiment.

FIG. 29 is a block diagram of a configuration of a workstation 3000, according to an exemplary embodiment.

Referring to FIG. 29, the workstation 3000 according to the present exemplary embodiment is configured to control an X-ray apparatus 500. The workstation 3000 includes an output unit 3100, a controller 3200, and an input unit 3300. The workstation 3000 may further include a communication unit 3400.

Since the output unit 3100, the controller 3200, and the input unit 3300 of the workstation 3000 respectively correspond to their counterparts of the medical imaging apparatus 2000, the same descriptions as provided above with respect to the medical imaging apparatus 2000 will be omitted below. Furthermore, the output unit 3100, the controller 3200, and the input unit 3300 may respectively correspond to their counterparts of the X-ray apparatus 500, and the above descriptions with respect to the X-ray apparatus 500 may be applied to the output unit 3100, the controller 3200, and the input unit 3300.

The communication unit 3400 may be configured to communicate with the X-ray apparatus 500 and/or with external devices such as servers, etc.

The X-ray apparatus 500 may acquire an image by photographing an object. The X-ray apparatus 500 may also transmit the image obtained by photographing the object to the workstation 3000.

The workstation 3000 may acquire the image via the communication unit 3400.

The output unit 3100 may display the image obtained by photographing the object. The output unit 3100 may also display a top indicator for setting a top limit for an area to be X-rayed and at least one guideline over the image. The above descriptions may be applied to operations of the output unit 3100, the input unit 3300, and the controller 3200, and thus, are not repeated.

Figure 30:
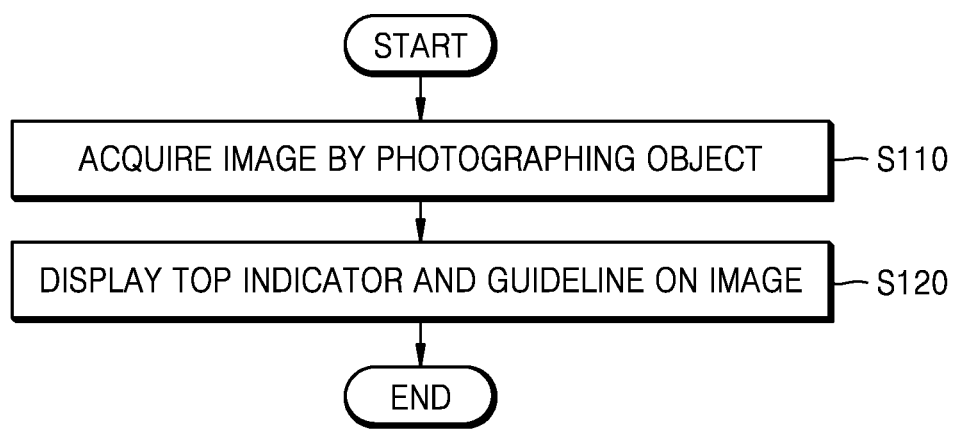
FIG. 30 is a flowchart of a method for operating a medical imaging apparatus, according to an exemplary embodiment.

FIG. 30 is a flowchart of a method for operating a medical imaging apparatus, according to an exemplary embodiment.

Referring to FIG. 30, in operation S110, the medical imaging apparatus acquires an image obtained by photographing an object. When the medical imaging apparatus is included in an X-ray apparatus, the X-ray apparatus may photograph the object. If the medical imaging apparatus is included in a workstation, the workstation may receive the image obtained by photographing the object from the X-ray apparatus.

In operation S120, the medical imaging apparatus may display a top indicator for setting a top limit for an area to be X-rayed and at least one guideline over the image.

Figure 31:
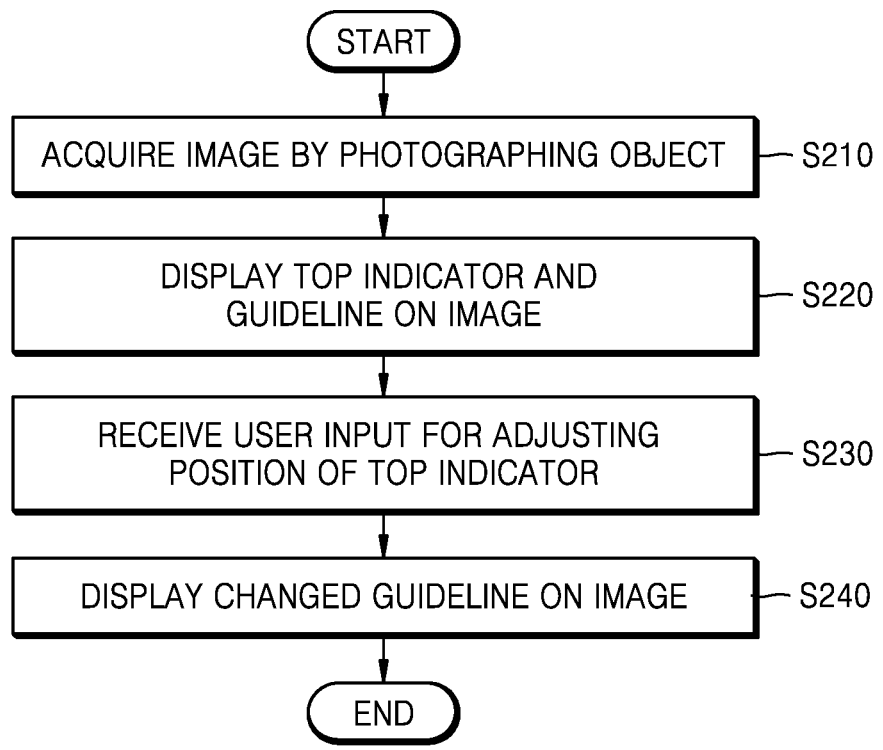
FIG. 31 is a flowchart of a method for operating a medical imaging apparatus, according to an exemplary embodiment.

FIG. 31 is a flowchart of a method for operating a medical imaging apparatus, according to an exemplary embodiment.

Referring to FIG. 31, in operation S210, the medical imaging apparatus acquires an image obtained by photographing an object. In operation S220, the medical imaging apparatus may display a top indicator for setting a top limit for an area to be X-rayed and at least one guideline over the image. In operation S230, the medical imaging apparatus may receive a user input for adjusting a position of the top indicator. In operation S240, the medical imaging apparatus may display at least one guideline that is changed according to the adjusted position of the top indicator over the image.

The medical imaging apparatus may receive a user input for setting a bottom limit for an area to be X-rayed. The medical imaging apparatus may determine the number of partial photographing operations based on the set bottom limit and partition an area in the image between the top indicator and the set bottom limit into regions for partial photographing operations according to the determined number of partial photographing operations.

The medical imaging apparatus may display the regions for partial photographing operations over the image. The medical imaging apparatus may also highlight overlapping portions between the regions.

The medical imaging apparatus may control an X-ray apparatus to respectively perform partial photographing operations on regions for the partial photographing operations. The medical imaging apparatus may then acquire a plurality of partial images via the partial photographing operations and obtain an X-ray image by stitching the plurality of partial images together.

The methods of operating the medical imaging apparatus illustrated in FIGS. 30 and 31 may be performed by the medical imaging apparatus 2000, the X-ray apparatus 500, or the workstation 3000. Each operation of the methods may be performed in the same manner as described above.

While it has been described that the medical imaging apparatus performs partial photographing operations on an area to be X-rayed, the medical imaging apparatus may perform a single X-ray photographing operation thereon. Thus, the medical imaging apparatus may operate in one of a partial imaging mode and a single imaging mode.

Figure 32:
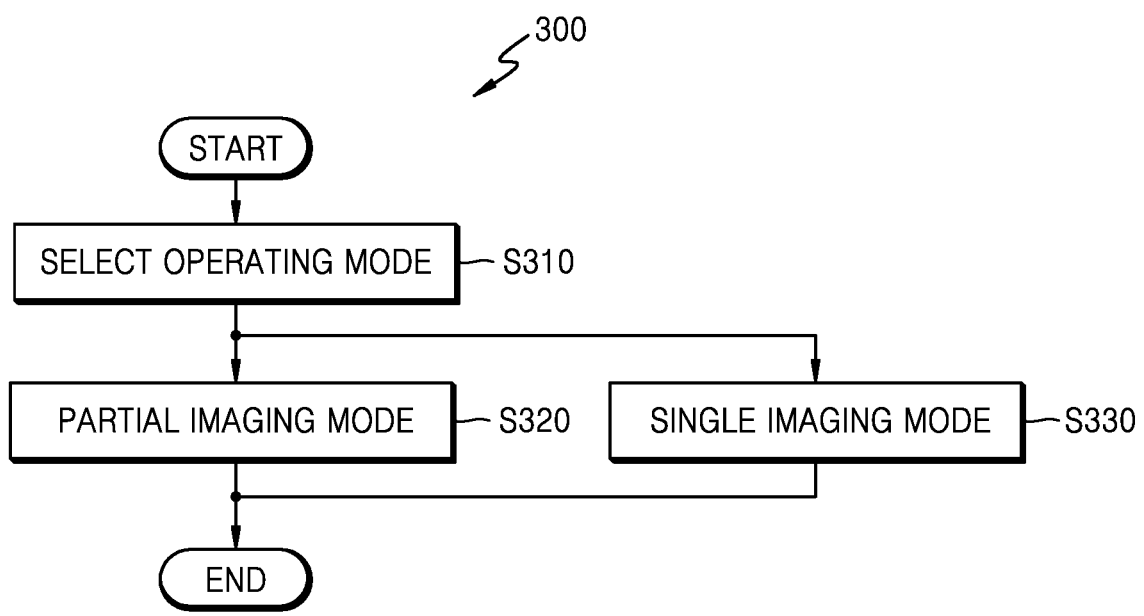
FIG. 32 is a flowchart of a method for operating a medical imaging apparatus, according to an exemplary embodiment.

FIG. 32 is a flowchart of a method 300 for operating a medical imaging apparatus, according to an exemplary embodiment;

Referring to FIG. 32, in operation S310, the medical imaging apparatus may select an operating mode. The operating mode includes a partial imaging mode and a single imaging mode. In detail, the medical imaging apparatus may receive a user input for selecting the operating mode. Alternatively, the operating mode may be preset by default or changed by a user. For example, an operating mode of the medical imaging apparatus preset by default may be a single imaging mode, and the medical imaging apparatus may receive a user input for changing the operating mode to a partial imaging mode.

The medical imaging apparatus may operate in a partial imaging mode (i.e., operation S320) or a single imaging mode (i.e., operation S330) according to the selected operating mode. The above descriptions may be applied when the medical imaging apparatus operates in the partial imaging mode (i.e., operation S320), and thus, are not repeated.

When the medical imaging apparatus operates in a single imaging mode (i.e., operation S330), the medical imaging apparatus may acquire an X-ray image of an object by performing a single X-ray photographing operation on the object.

Figure 33:
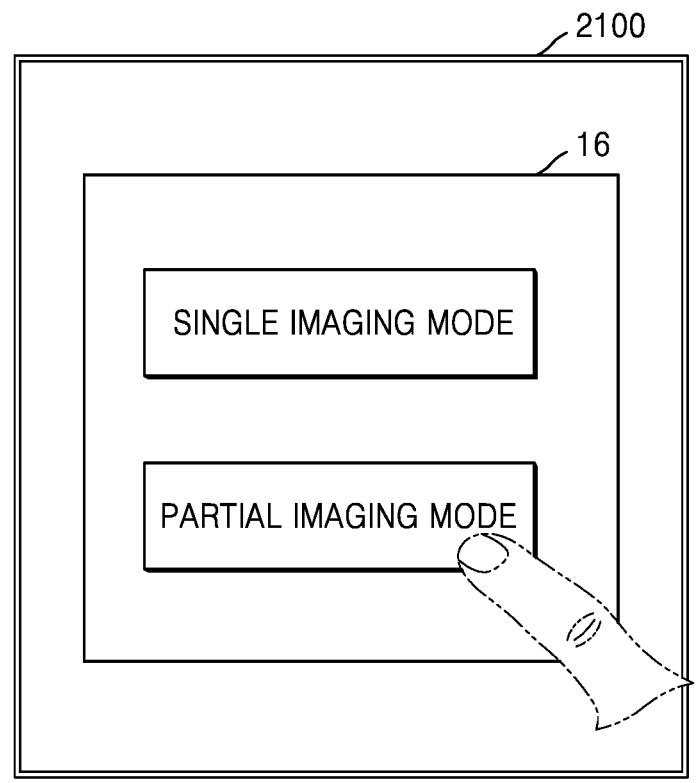
FIG. 33 is an example in which the medical imaging apparatus of FIG. 9 receives a user input for selecting an operating mode.

FIG. 33 is an example in which the medical imaging apparatus 2000 of FIG. 9 receives a user input for selecting an operating mode.

Referring to FIG. 33, the output unit 2100 of the medical imaging apparatus 2000 may output a UI 16 that enables a user to select the operating mode. The input unit 2300 of the medical imaging apparatus 2000 may receive a user input for selecting a single or partial imaging mode via the UI 16.

Although FIG. 33 shows the example in which the medical imaging apparatus 2000 receives a user input for selecting an operating mode, exemplary embodiments are not limited thereto. The medical imaging apparatus may receive a user input for selecting an operating mode in any of various ways.

When the single imaging mode is selected, the medical imaging apparatus may operate in a general operating mode. Alternatively, when the medical imaging apparatus is in a single imaging mode, the medical imaging apparatus may operate as described below with respect to exemplary embodiments.

Figure 34:
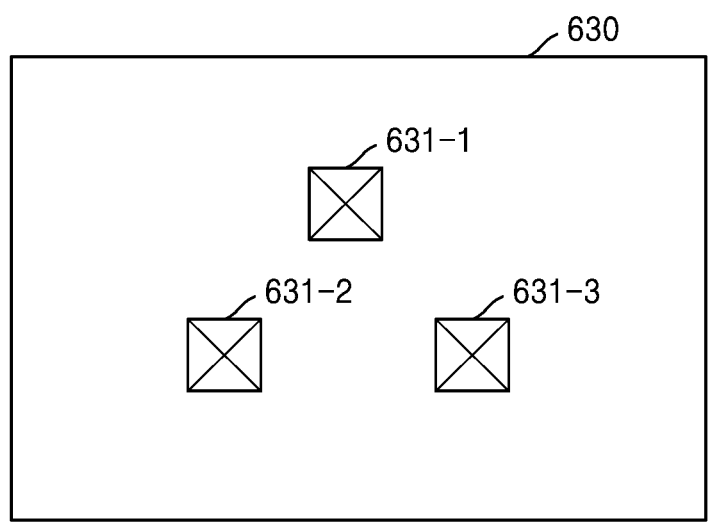
FIG. 34 illustrates a detector, according to an exemplary embodiment.

FIG. 34 illustrates a detector 630, according to an exemplary embodiment.

Referring to FIG. 34, the detector 630 may include at least one of automatic exposure control (AEC) chambers 631-1, 631-2, and 631-3. Although FIG. 34 shows that the detector 630 includes the three (3) AEC chambers 631-1, 631-2, and 631-3, exemplary embodiments are not limited to the number or positions of the AEC chambers 631-1, 631-2, and 631-3 within the detector 630.

The detector 630 of FIG. 34 may be included in each of the X-ray apparatuses 100, 200, 300, and 500 or may be an X-ray detector that is a separate device which is connectable to or disconnectable from each of the X-ray apparatuses 100, 200, 300, and 500.

Figure 35:
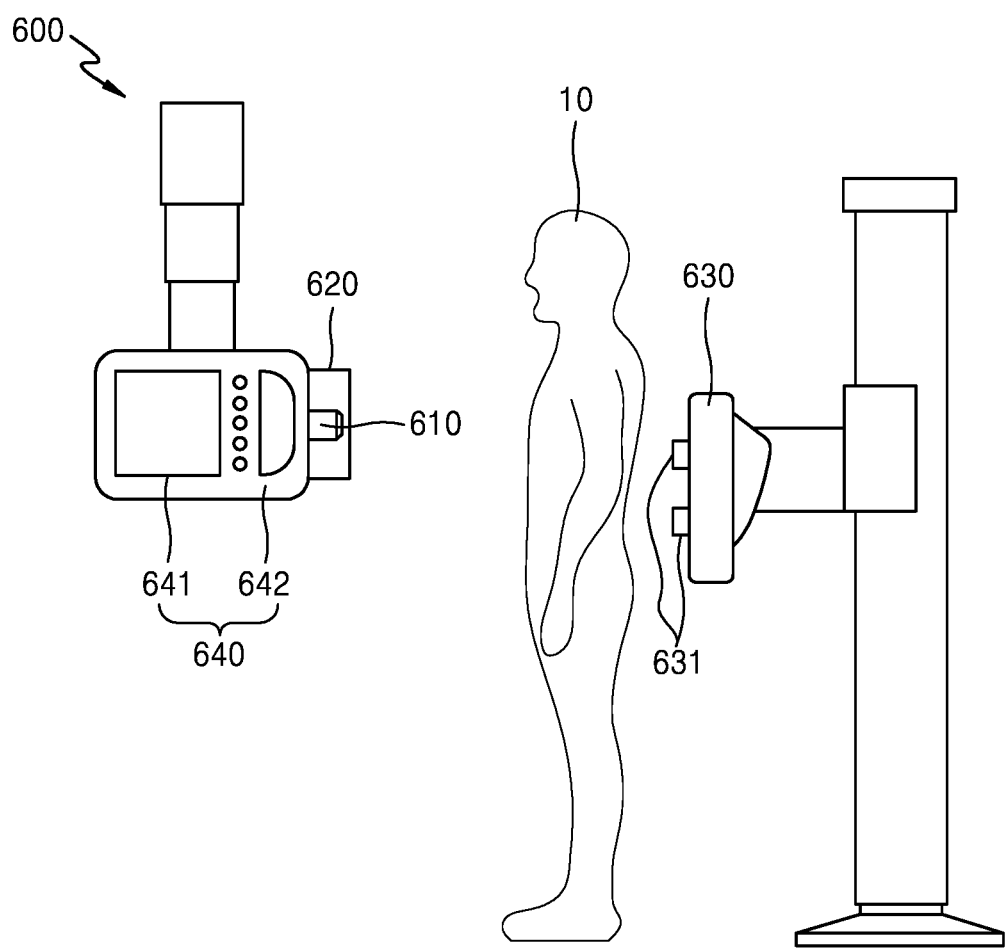
FIG. 35 illustrates an X-ray apparatus, according to an exemplary embodiment.

FIG. 35 illustrates an X-ray apparatus 600, according to an exemplary embodiment.

Referring to FIG. 35, the detector 630 includes at least one AEC chamber 631. While FIG. 35 shows that the at least one AEC chamber 631 appears to protrude out of the detector 630, this is merely for convenience, and the at least one AEC chamber 631 does not actually protrude upward from the detector 630. The detector 630 may be included in the X-ray apparatus 600 or may be an X-ray detector that is a separate device which is connectable to or disconnectable from the X-ray apparatus 600.

The X-ray apparatus 600 includes an image acquisition unit 610, an X-ray radiator 620, and a manipulator 640. The manipulator 640 may include an output unit 641 and an input unit 642. Even if not expressly specified here, the above descriptions with respect to an X-ray apparatus may be applied to the X-ray apparatus 600.

When X-rays are emitted by the X-ray radiator 620, the AEC chamber 631 of the detector 630 may detect the amount of the X-rays received after propagating through an object 10. If the amount of the received X-rays exceeds a predetermined amount, the AEC chamber 631 may transmit a notification signal to a controller (not shown) of the X-ray apparatus 600. When the notification signal is received, the controller may stop X-ray irradiation by the X-ray radiator 620.

Thus, the amount of emitted X-rays may be adjusted via the AEC chamber 631, thereby protecting the object 10 from excessive exposure to X-rays.

However, since the detector 630 is blocked by the object 10, the user of the X-ray apparatus 600 is not able to recognize a position of the AEC chamber 631.

Before taking an X-ray of the object 10, the image acquisition unit 610 may acquire an image of the object 10 by photographing the object 10.

The output unit 641 may display an AEC marker visually associated with the AEC chamber 631 over the image obtained by photographing the object 10. In the image, the AEC marker indicates a position of the AEC chamber 631 included in the detector 630.

The controller may control the output unit 641 to display an AEC marker over the image obtained by photographing the object 10. The controller may also perform various image processing or data processing operations necessary for displaying the AEC marker.

In detail, the controller may perform geometric registration of the image by matching each point in the image with a position in the real world. The controller may also acquire the position of the AEC chamber that corresponds to the position of the detector 630 and coordinate the AEC chamber 631 with the image. The controller may perform image processing whereby the AEC chamber is coordinated with the image and the AEC marker that corresponds to the AEC chamber 631 is superimposed onto the image.

The descriptions with respect to the X-ray apparatus 600 may also be applied to the medical imaging apparatus 2000 of FIG. 9. Hereinafter, a screen of the output unit 2100 of the medical imaging apparatus 2000 according to an exemplary embodiment is described. The following descriptions with respect to the medical imaging apparatus 2000 are also applicable to an X-ray apparatus or workstation.

Figure 36:
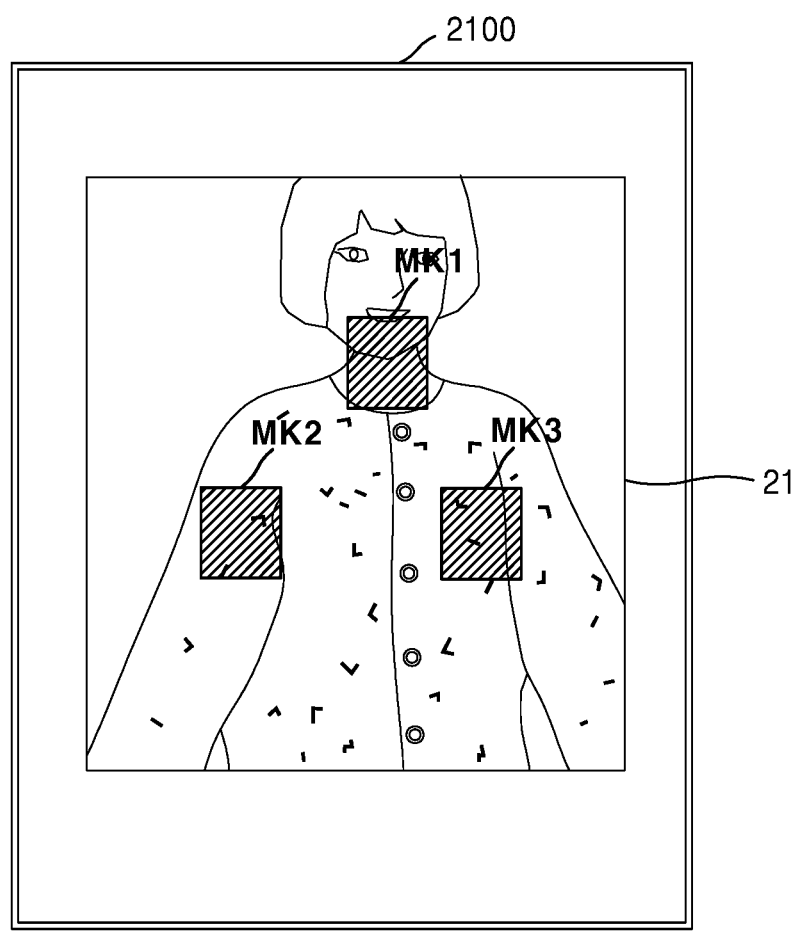
FIG. 36 is an example in which an output unit of the medical imaging apparatus of FIG. 9 displays an automatic exposure control (AEC) marker over an image obtained by photographing an object.

FIG. 36 is an example in which the output unit 2100 of the medical imaging apparatus 2000 of FIG. 9 displays a plurality of AEC markers MK1, MK2, and MK3 over an image 21 obtained by photographing an object.

Referring to FIG. 36, the output unit 2100 may display the image 21 obtained by photographing the object and display the plurality of AEC markers MK1, MK2, and MK3 over the image 21.

The image 21 shown in FIG. 36 may be an image of a portion of the object, i.e., an image of an area to be X-rayed. In this case, X-ray photographing may be a single photographing operation.

The AEC markers MK1, MK2, and MK3 displayed over the image 21 are visually associated with the at least one AEC chamber (i.e., item 631 of FIG. 35). The AEC markers MK1, MK2 and MK3 may correspond to the at least one AEC chambers 631 mapped onto the image 21. In this aspect, the AEC markers MK1, MK2, and MK3 each correspond to the AEC chamber 631 of the detector 630. For example, referring to FIGS. 34 and 36 together, the AEC markers MK1, MK2, and MK3 may respectively correspond to the AEC chambers 631-1, 631-2, and 631-3 of the detector 630.

Portions in the image 21 where the AEC markers MK1, MK2, and MK3 are located may correspond to positions of the AEC chambers 631 of the detector 630, which are determined according to a position of the detector 630 relative to the object during X-ray imaging. On the image 21, the AEC marker MK1 is located near a neck and a jaw in the image 21 of the object. This means that an AEC chamber of the detector 630 that corresponds to the AEC marker MK1 is located at a position corresponding to a jaw and a neck of the object during X-ray imaging of the object.

Since the detector 630 is blocked by the object 10 during X-ray imaging as shown in FIG. 35, the user is not able to directly recognize a position of the AEC chamber 631. According to an exemplary embodiment, the output unit 2100 may display the AEC markers MK1, MK2, and MK3 over the image 21 as shown in FIG. 36, thereby enabling the user to intuitively and conveniently recognize a relationship between positions of an actual object and an AEC chamber.

The controller 2200 of the medical imaging apparatus 2000 may set on/off states of each of the AEC markers MK1, MK2, and MK3. The controller 2200 may turn on or off an AEC chamber of a detector according to the set on/off states of a corresponding one of the AEC markers MK1, MK2, and MK3. If the detector includes a plurality of AEC markers MK1, MK2, and MK3, the controller 2200 may set on/off states of each of the AEC markers MK1, MK2, and MK3. An AEC chamber that is turned off does not perform its operations, including the operation of comparing the amount of received X-rays with a predetermined amount.

The controller 2200 may set on/off states of the AEC markers MK1, MK2, and MK3 according to a user input.

The user may set on/off states of each of the AEC markers MK1, MK2, and MK3 after identifying a relationship between positions of the object and each of the AEC markers MK1, MK2, and MK3 via the output unit 2100. In particular, the input unit 2300 of the medical imaging apparatus 2000 may receive a user input for setting an on/off state of an AEC marker selected from among the AEC markers MK1, MK2, and MK3.

Figure 37:
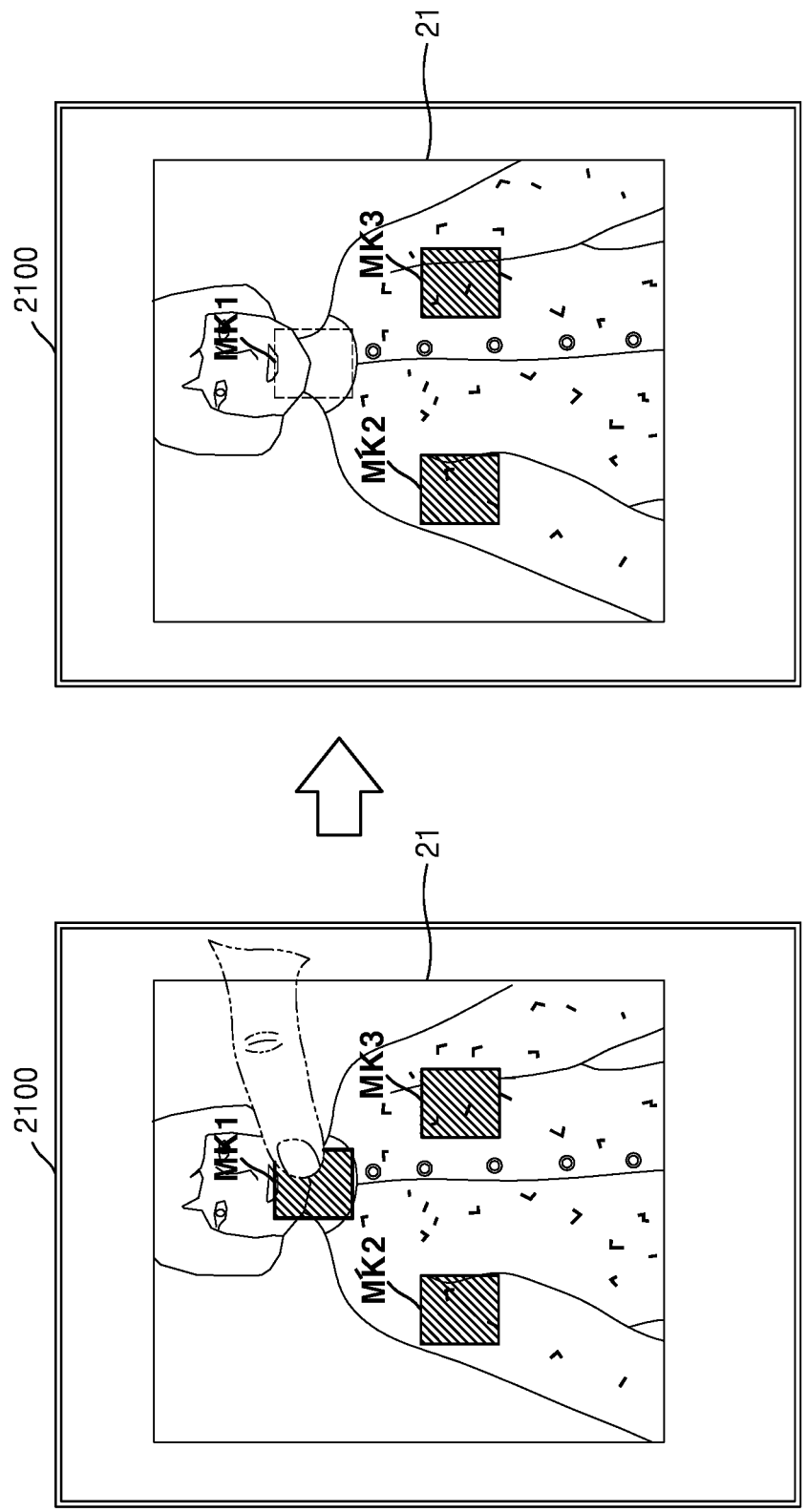
FIGS. 37A and 37B illustrate an example of a medical imaging apparatus receiving a user input for setting an on/off state of an AEC marker.

FIGS. 37A and 37B illustrate an example of the medical imaging apparatus 2000 receiving a user input for setting an on/off state of an AEC marker.

Referring to FIGS. 37A and 37B, the output unit 2100 of the medical imaging apparatus 2000 may display first, second, and third AEC markers MK1, MK2, and MK3 over an image 21 obtained by photographing an object. The output unit 2100 may display the first, second, and third AEC markers MK1, MK2, and MK3 so that on/off states of each of the first, second, and third AEC markers MK1, MK2, and MK3 are distinguished from one another. An on/off state of each of the first, second, and third AEC markers MK1, MK2, and MK3 is associated with an on/off state of its corresponding AEC chamber. In particular, an AEC chamber that corresponds to an AEC marker displayed in an off-state among the first, second, and third AEC markers MK1, MK2, and MK3 is set to an off-state. An AEC chamber that corresponds to an AEC marker displayed in an on-state among the first, second, and third AEC markers MK1, MK2, and MK3 is set to an on-state. In the figures, when each of the AEC markers MK1, MK2, and MK3 is indicated by a dashed line, it means that the AEC marker is in an off-state. Otherwise, if each AEC marker is indicated by a solid line, it means that the AEC marker is in an on-state. However, exemplary embodiments are not limited thereto. As another example, each of the first, second, and third AEC markers MK1, MK2, and MK3 may be indicated in a different color according to its on/off state.

Referring to FIG. 37A, the output unit 2100 displays the first, second, and third AEC markers MK1, MK2, and MK3 that are in an on-state. The user may change the state of the first AEC marker MK1 from an on-state to an off-state by touching the first AEC marker MK1. Furthermore, the controller 2200 may control the detector 630 to turn off an AEC chamber that corresponds to the first AEC marker MK1.

When the first AEC marker MK1 changes from an on-state to an off-state as shown in FIG. 37A, the output unit 2100 may change the displayed state of the first AEC marker MK1 from an on-state to an off-state, as shown in FIG. 37B.

As shown in FIGS. 37A and 37B, the user may set an on/off state of a desired AEC chamber by touching an AEC marker that corresponds to the desired AEC chamber among the first, second, and third AEC markers MK1, MK2, and MK3. When an AEC marker displayed in an on-state is touched, an AEC chamber that corresponds to the touched AEC marker may change from an on-state to an off-state. When an AEC marker displayed in an off-state is touched, an AEC chamber that corresponds to the touched AEC marker may change from an off-state to an on-state. However, FIGS. 37A and 37B are merely examples where the input unit 2300 receives a user input for setting an on/off state of an AEC chamber, and methods of receiving a user input according to exemplary embodiments are not limited thereto.

In the image 21 obtained by photographing the object, the first AEC marker MK1 is located near a jaw and a neck of the object. In this aspect, a real AEC chamber on a detector that corresponds to the first AEC marker MK1 may be located near a jaw and a neck of an actual object. However, if an AEC chamber that corresponds to the first AEC marker MK1 receives X-rays, the amount of the X-rays that are irradiated on the object until the amount of received X-rays exceeds a predetermined amount may be greater than in the other AEC chambers MK2 and MK3 due to a thickness of the jaw. Furthermore, if an ROI is a chest of the object, the jaw and neck that are outside the ROI may be unnecessarily and excessively irradiated with X-rays. In this case, by turning off an AEC chamber that corresponds to the first AEC marker MK1, it is possible to prevent excessive X-ray irradiation.

According to an exemplary embodiment, when the first, second, and third AEC markers MK1, MK2, and MK3 which indicate respective positions of their corresponding AEC chambers on the detector are displayed over the image 21, the user may intuitively identify an AEC chamber that is located outside an ROI based on the displayed first, second, and third AEC markers MK1, MK2, and MK3. In this case, the user may turn off the AEC chamber that is outside the ROI, thereby preventing unnecessary excessive irradiation by X-rays. Furthermore, the user may easily set on/off states of the AEC chambers via the displayed first, second, and third AEC markers MK1, MK2, and MK3.

In this way, the medical imaging apparatus 2000 may turn on or off the first, second, and third AEC markers MK1, MK2, and MK3 according to a user input.

The medical imaging apparatus 2000 may also set an on/off state of each of the first, second, and third AEC markers MK1, MK2, and MK3 by analyzing the image 21.

Figure 38:
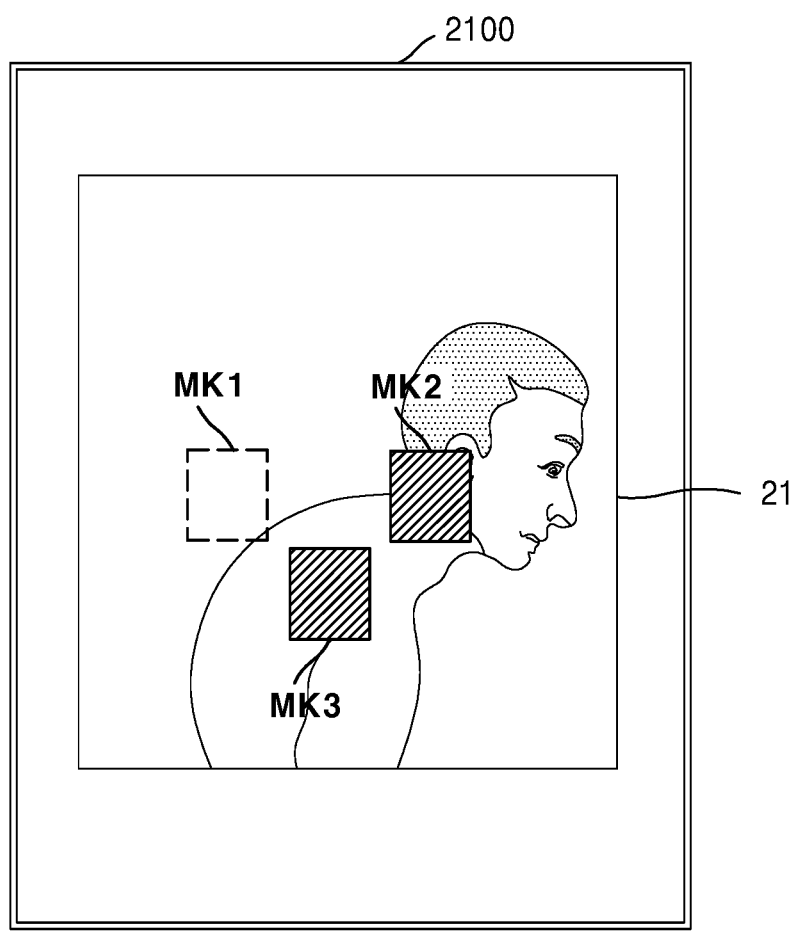
FIG. 38 is an example in which the medical imaging apparatus of FIG. 9 sets an on/off state of an AEC marker via image processing.

FIG. 38 is an example in which the medical imaging apparatus 2000 of FIG. 9 sets an on/off state of an AEC marker via image processing.

Referring to FIG. 38, the output unit 2100 of the medical imaging apparatus 2000 may display first, second, and third AEC markers MK1, MK2, and MK3 over an image obtained by photographing an object. The output unit 2100 may indicate that the first AEC marker MK1 is in an off-state and the other second and third AEC markers MK2 and MK3 are in an on-state by displaying the first AEC marker MK1 as a dashed line and the second and third AEC markers MK2 and MK3 as a solid line.

In the image 21, the first AEC marker MK1 is located outside the object. In this aspect, a real AEC chamber on the detector that corresponds to the first AEC marker MK1 may be located outside a real-world object, i.e., outside an ROI. In this case, the controller 2200 of the medical imaging apparatus 2000 may detect that the first AEC marker MK1 is outside the object or ROI. The controller 2200 may detect a contour of the object in the image 21 via image processing for detecting a contour in the image 21. The controller 2200 may detect whether each of the first, second, and third AEC markers MK1, MK2, and MK3 is located outside the object based on the detected contour of the object.

As shown in FIG. 38, the controller 2200 may detect that the first AEC marker MK1 among the first, second, and third AEC markers MK1, MK2, and MK3 is located outside the object. The controller 2200 controls the output unit 2100 to indicate that the first AEC marker MK1, which is detected as being outside the object, is in an off-state.

If the first AEC marker MK1 is not turned off, an AEC chamber that corresponds to the first AEC marker MK1 may directly receive X-rays that have not passed through the object. This causes the amount of X-rays received by the AEC chamber that corresponds to the first AEC marker MK1 to quickly exceed a predetermined amount. In this case, the quality of an X-ray image may be degraded due to the lack of X-ray dose irradiated on the object.

Thus, the medical imaging apparatus 2000 may prevent degradation in quality of an X-ray image by turning off an AEC marker that is positioned outside the object.

Figure 39:
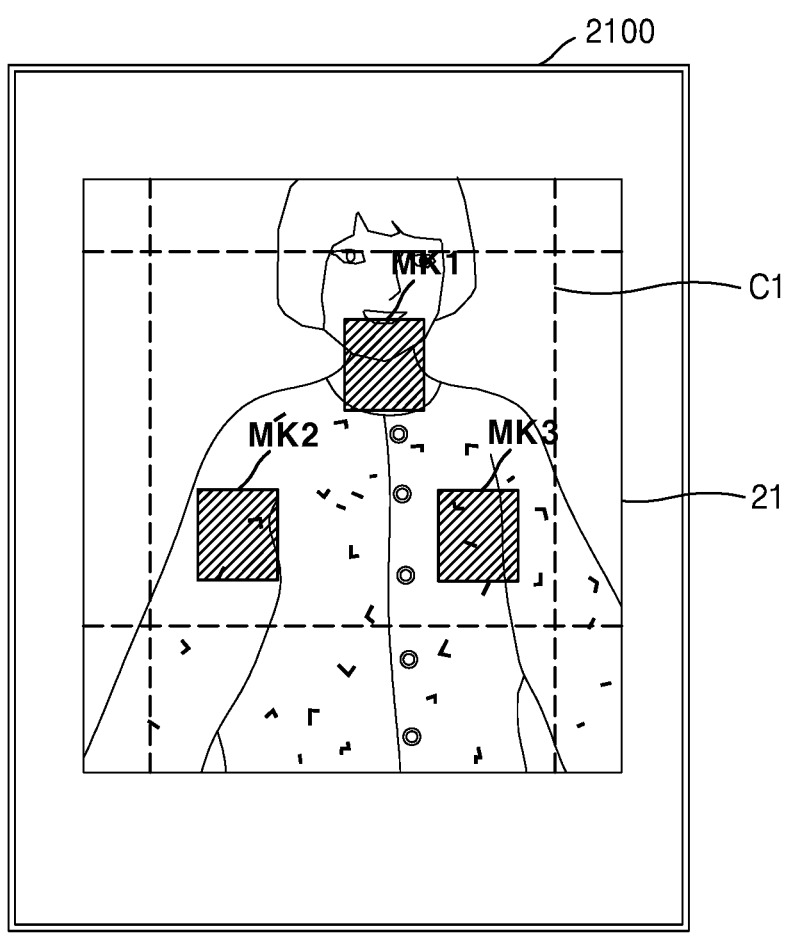
FIG. 39 is an example in which the output unit of the medical imaging apparatus of FIG. 9 displays an AEC marker and a collimation area over an image obtained by photographing an object.

FIG. 39 is an example in which the output unit 2100 of the medical imaging apparatus 2000 of FIG. 9 displays AEC markers and a collimation area over an image obtained by photographing an object.

Referring to FIG. 39, the output unit 2100 of the medical imaging apparatus 2000 may display AEC markers MK1, MK2, and MK3 over an image 21 obtained by photographing an object. The output unit 2100 may further display a collimation area C1 over the image 21. A "collimation area" refers to a range of X-rays to be irradiated onto an object when the X-rays are radiated according to an X-ray irradiation region adjusted by the collimator 523.

The collimation area C1 may vary according to a relationship between positions of the object and the X-ray radiator 520 and an aperture of the collimator 523. The aperture of the collimator 523 may be adjusted via movement of the blades 525 included in the collimator 523 (see, for example, FIG. 28).

The controller 2200 may coordinate the collimation area C1 with the image 21 according to the relationship between positions of the object and the X-ray radiator 520 and the aperture of the collimator 523. The controller 2200 may then perform image processing whereby the collimation area C1 is superimposed onto the image 21.

After identifying the collimation area C1 via the output unit 2100, the user may adjust the collimation area C1. For example, at least one of a position and a size of the collimation area C1 may be adjusted. In particular, the input unit 2300 of the medical imaging apparatus 2000 may receive a user input for adjusting the collimation area C1.

Figure 40B:
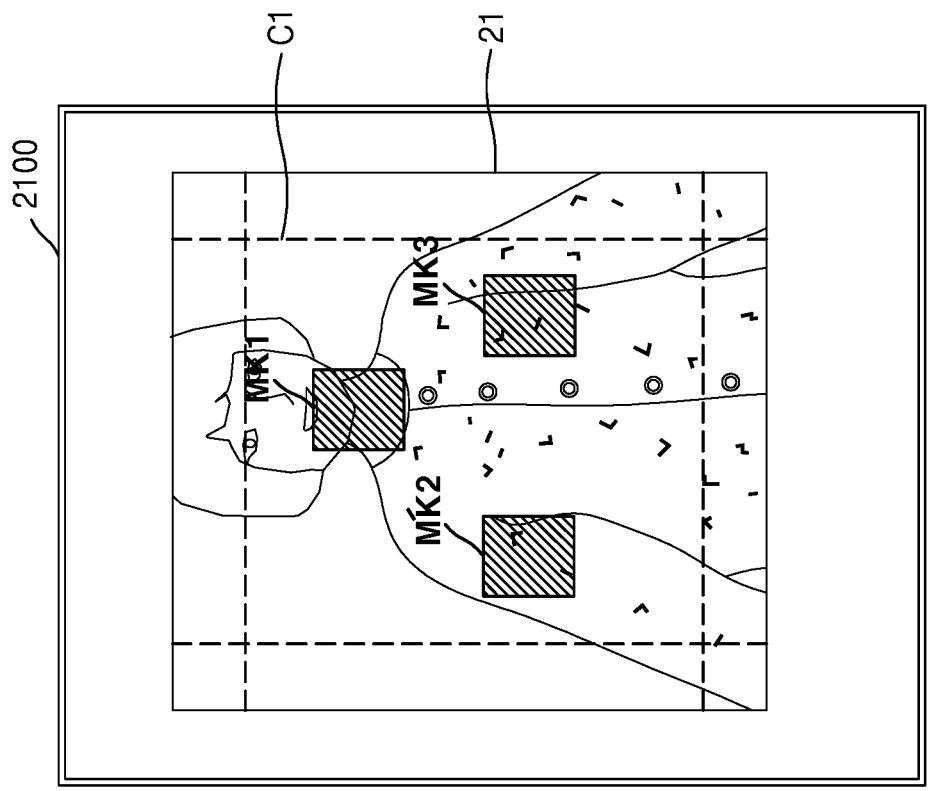
FIGS. 40A and 40B illustrate an example in which the medical imaging apparatus of FIG. 9 receives a user input for adjusting a collimation area.
Figure 40A:
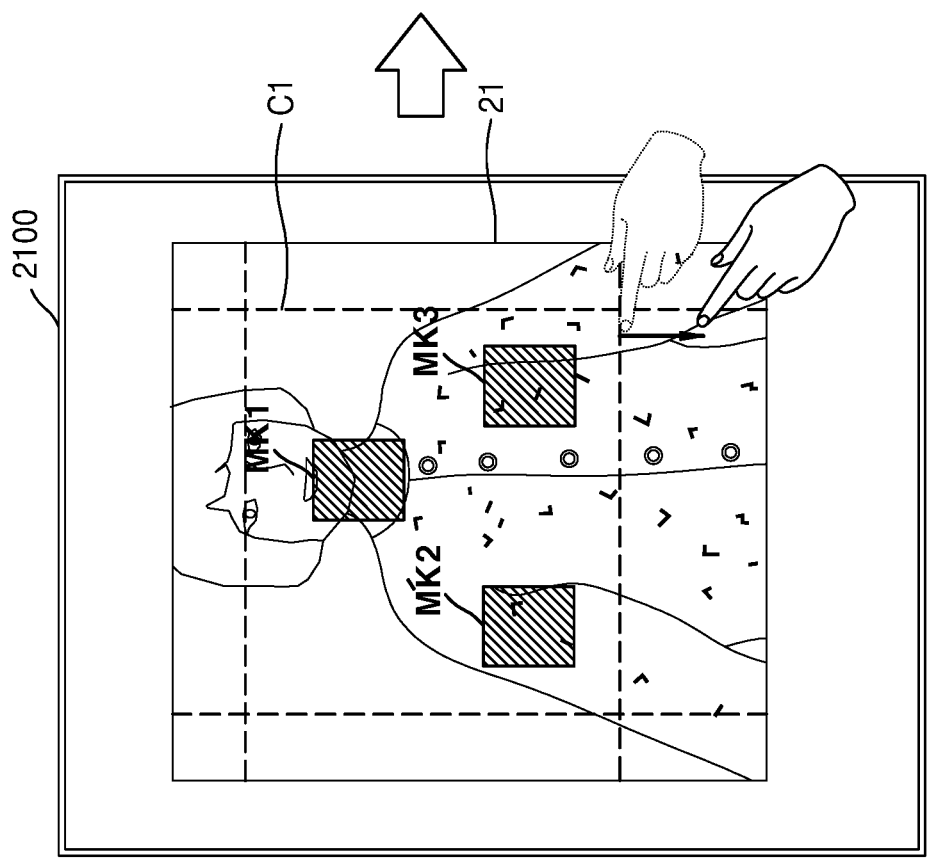

FIGS. 40A and 40B illustrate an example in which the medical imaging apparatus of FIG. 9 receives a user input for adjusting a collimation area.

Referring to FIG. 40A, the output unit 2100 of the medical imaging apparatus 2000 may display AEC markers MK1, MK2, and MK3 and a collimation area C1 over an image 21 obtained by photographing an object. The user may adjust the collimation area C1 by dragging one of a plurality lines representing the collimation area C1 with a finger. FIG. 40A is merely an example, and the user input for adjusting the collimation area C1 may be performed in any of various ways according to an implemented configuration of the input unit 2300.

When the collimation area C1 is adjusted according to a user input as shown in FIG. 40A, the output unit 2100 may display the adjusted collimation area C1 over the image 21 as shown in FIG. 40B.

The controller 2200 may control the collimator 523 of the X-ray apparatus 500 according to the adjusted collimation area C1. The controller 2200 may control an aperture of the collimator 523 so that the adjusted collimation area C1 corresponds to an X-ray irradiation region.

Figure 41A:
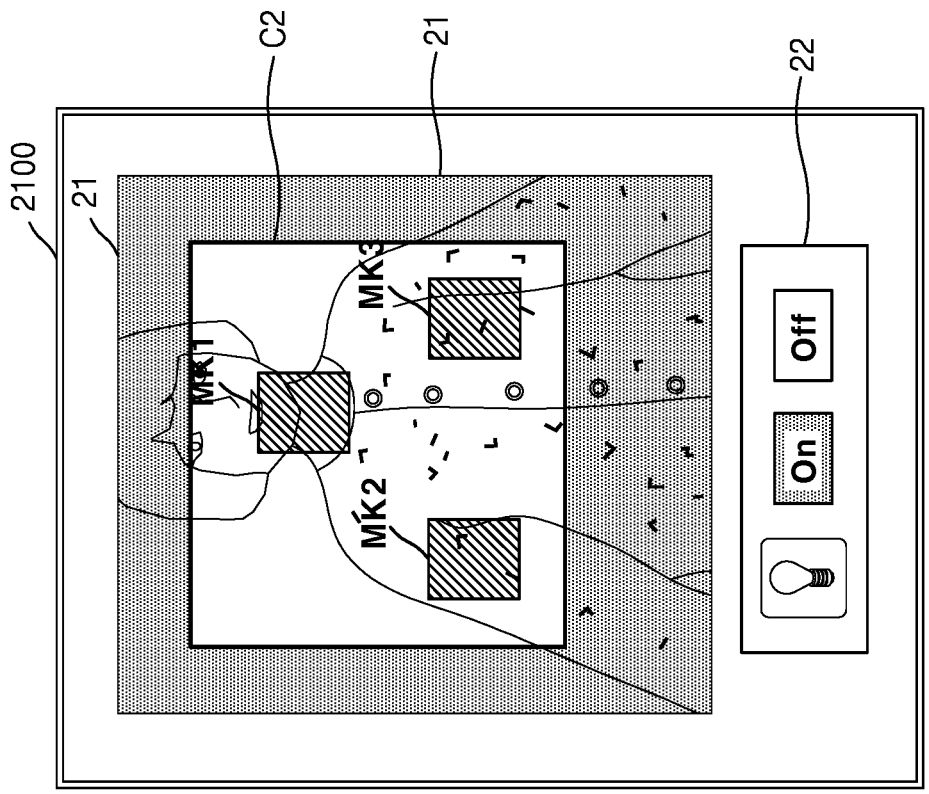
FIGS. 41A and 41B illustrate an example in which a user turns on a lamp of a collimator in the medical imaging apparatus of FIG. 9 and checks a collimation area.
Figure 41B:
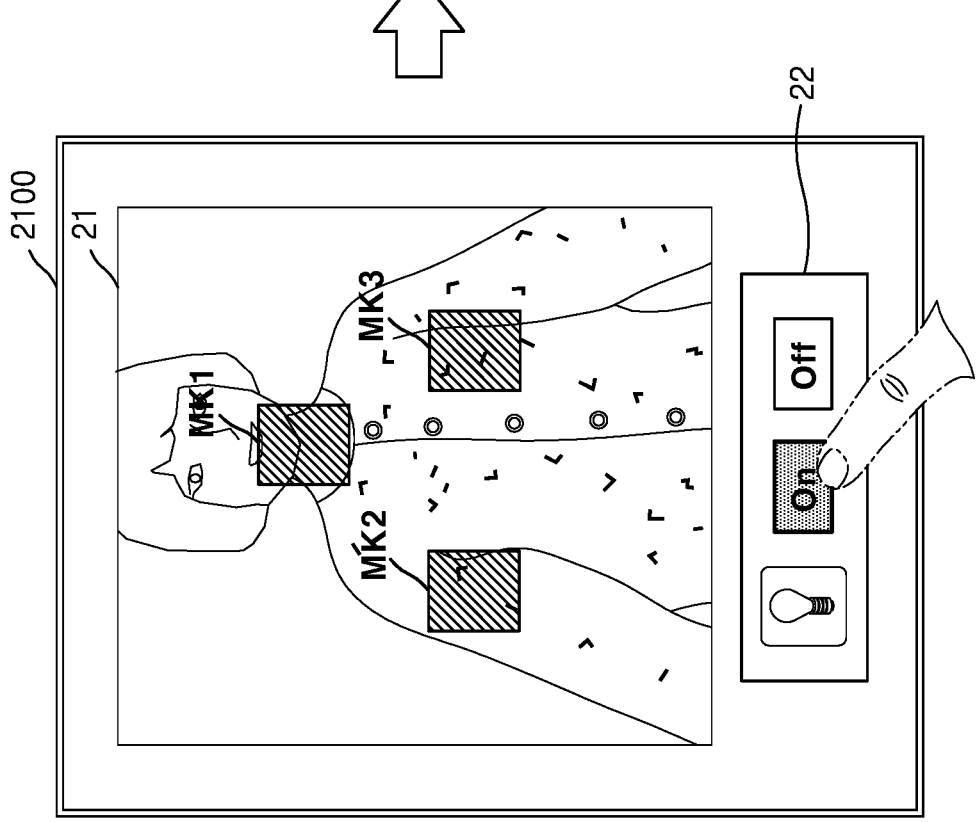

FIGS. 41A and 41B illustrate an example in which a user turns on a lamp of a collimator in the medical imaging apparatus 2000 of FIG. 9 and identifies a collimation area.

Referring to FIGS. 41A and 41B, the output unit 2100 may further display a UI 22 that enables the user to turn or off a lamp of the collimator 523, as well as an image 21 obtained by photographing an object. The UI 22 shown in FIGS. 41A and 41B is merely an example, and exemplary embodiments are not limited thereto.

Referring to FIG. 41A, the input unit 2300 may receive a user input for turning on a lamp of the collimator 523 via the UI 22. When the lamp of the collimator 523 is turned on, light is emitted onto the object, making a portion of the object irradiated with light appear bright and the remaining portion appear dark. The bright portion of the object is a collimation area.

FIG. 41B illustrates an image 21 obtained by photographing the object, which is displayed by the output unit 2100 after the lamp of the collimator 523 is turned on. A collimation area C2 may appear in the image 21 due to a shadow created by turning on the lamp. In this case, the medical imaging apparatus 2000 does not superimpose the collimation area C2 on the image 21 via image processing. The collimation area C2 is a photographed shadow created on a real-world object due to turning on of the lamp of the collimator 523.

Setting an on/off state of an AEC marker displayed on the image 21 obtained by photographing an object has been described with reference to FIGS. 37A, 37B, and 38. Setting an on/off state of an AEC marker according to another exemplary embodiment will be described in detail below.

Figure 42B:
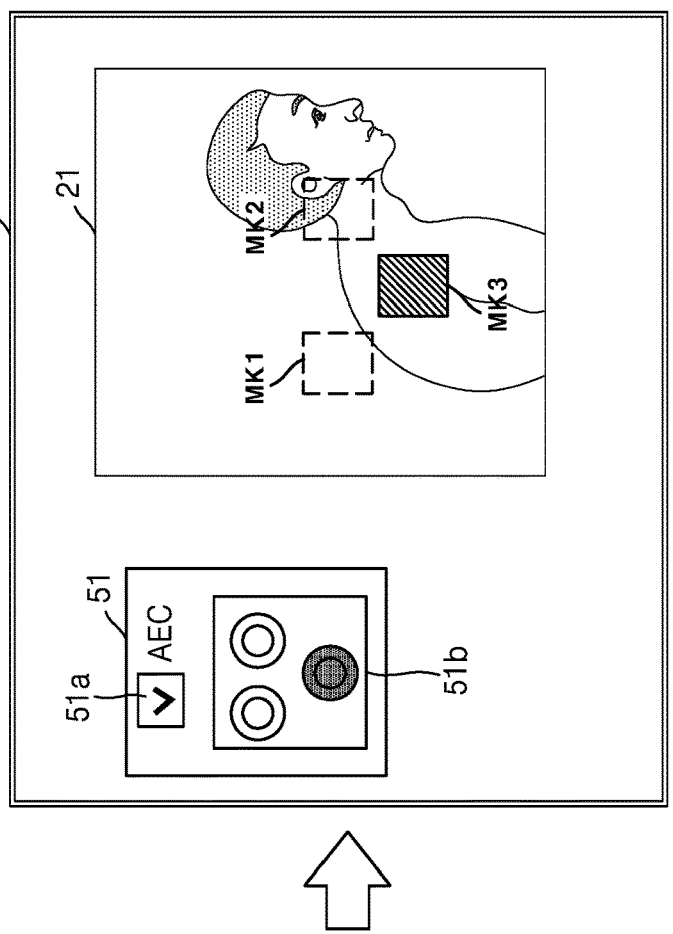
FIGS. 42A and 42B illustrate an example in which an output unit of the medical imaging apparatus of FIG. 9 further displays a UI for setting an on/off state of an AEC marker.
Figure 42A:
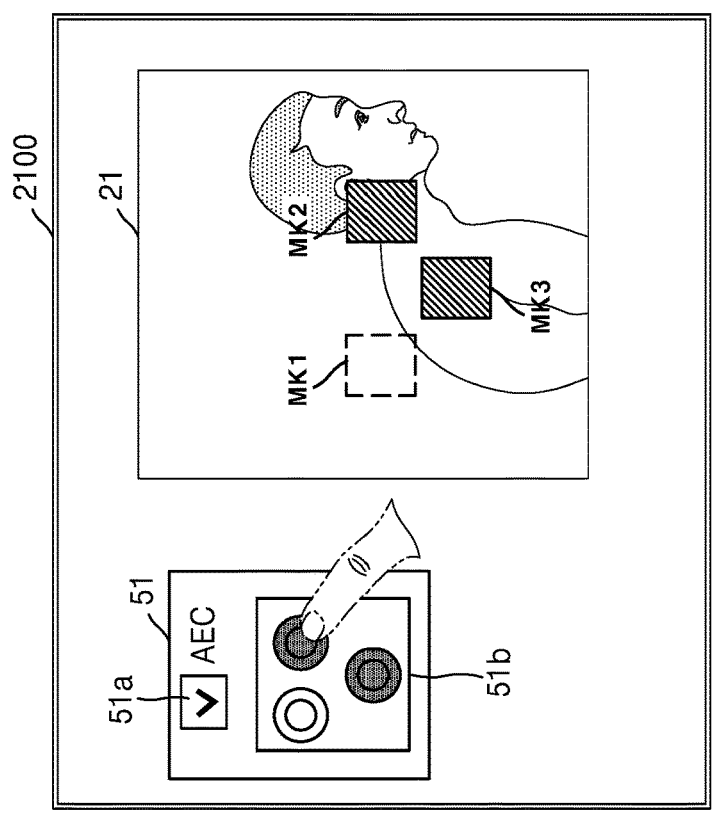

FIGS. 42A and 42B illustrate an example in which the output unit 2100 of the medical imaging apparatus 2000 of FIG. 9 further displays a UI for setting an on/off state of an AEC marker.

Referring to FIGS. 42A and 42B, the output unit 2100 may further display a UI 51 that enables a user to set on/off states of first, second, and third AEC markers MK1, MK2, and MK3, as well as an image 21 obtained by photographing an object and on which the first, second, and third AEC markers are superimposed. The UI 51 may include a first UI 51a for turning off all of the first, second, and third AEC markers MK1, MK2, and MK3 at once and a second UI 51b for separately turning on or off each of the first, second, and third AEC markers MK1, MK2, and MK3.

For example, the user may turn off all of the first, second, and third AEC markers MK1, MK2, and MK3 at once by selecting the first UI 51a via a touch, click, etc. After the first, second, and third AEC markers MK1, MK2, and MK3 are all turned off, they are respectively returned to their original on/off states before being turned off when the user selects the first UI 51a again.

The second UI 51b may include icons arranged in the same manner as the first, second, and third AEC markers MK1, MK2, and MK3. The user may turn on or off an AEC marker by selecting an icon that corresponds to the AEC marker via touch or click. The icons in the second UI 51b may be displayed so that they are distinguished from one another according to an on/off state of each of the first, second, and third AEC markers MK1, MK2, and MK3.

Referring to FIG. 42A, only the first AEC marker MK1 is turned off among the first, second, and third AEC markers MK1, MK2, and MK3. Thus, an icon that corresponds to the first AEC marker MK1 among the icons in the second UI 51b is displayed so as to distinguish it from the other icons.

The input unit 2300 may receive a user input for selecting an icon that corresponds to the second AEC marker MK2 from the second UI 51b. According to the user input, the controller 2200 may change the second AEC marker MK2 from an on-state to an off-state. The controller 2200 may control the output unit 2100 to display the second AEC marker MK2 in an off-state as shown in FIG. 41B. The output unit 2100 may also display the state of the icon that corresponds to the second AEC marker MK2 among the icons in the second UI 51b as an off-state.

While FIGS. 42A and 42B show that the output unit 2100 displays the image 21 and the UI 51 for setting on/off states of the first, second, and third AEC markers MK1, MK2, and MK3, exemplary embodiments are not limited thereto. The output unit 2100 may further display another UI or pieces of information necessary for X-ray imaging.

Figure 43:
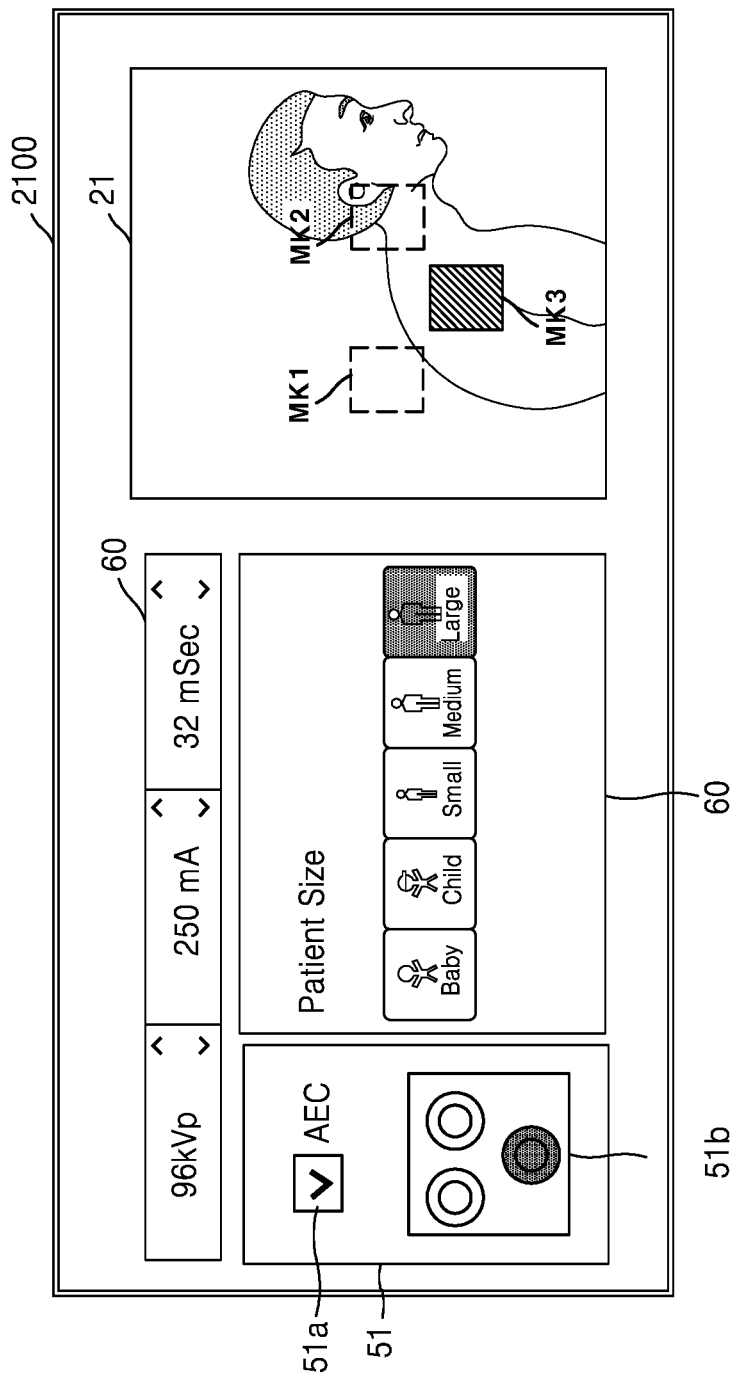
FIG. 43 is an example of an output unit of a medical imaging apparatus, according to an exemplary embodiment.

FIG. 43 is an example of an output unit 2100 of a medical imaging apparatus, according to an exemplary embodiment;

Referring to FIG. 43, the output unit 2100 may further display another UI 60 necessary for X-ray imaging, as well as an image 21 obtained by photographing an object and a UI 51 for setting on/off states of AEC markers MK1, MK2, and MK3. The UI 60 shown in FIG. 43 enables the user to set conditions for irradiation by an X-ray source or a size of the object. However, the UI 60 is merely an example, and a screen displayed by the output unit 2100 is not limited thereto.

Displaying AEC markers MK1, MK2, and MK3 via the output unit 2100 when the medical imaging apparatus is in a single imaging mode according to exemplary embodiments have been described above with reference to FIGS. 37A through 43. The above descriptions with respect to the AEC markers MK1, MK2, and MK3 may be applied to displaying AEC markers when the medical imaging apparatus is in a partial imaging mode.

Figure 44A:
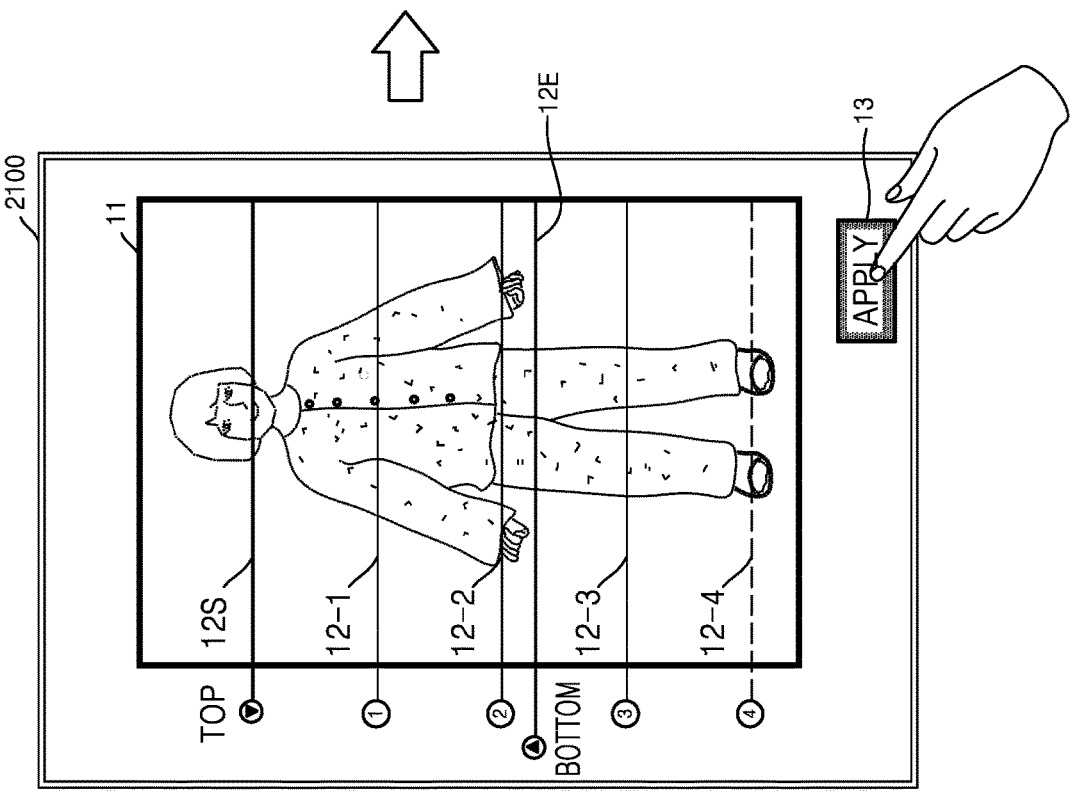
FIGS. 44A and 44B illustrate an example of a screen of an output unit on which AEC markers are displayed when the medical imaging apparatus of FIG. 9 is in a partial imaging mode.
Figure 44B:
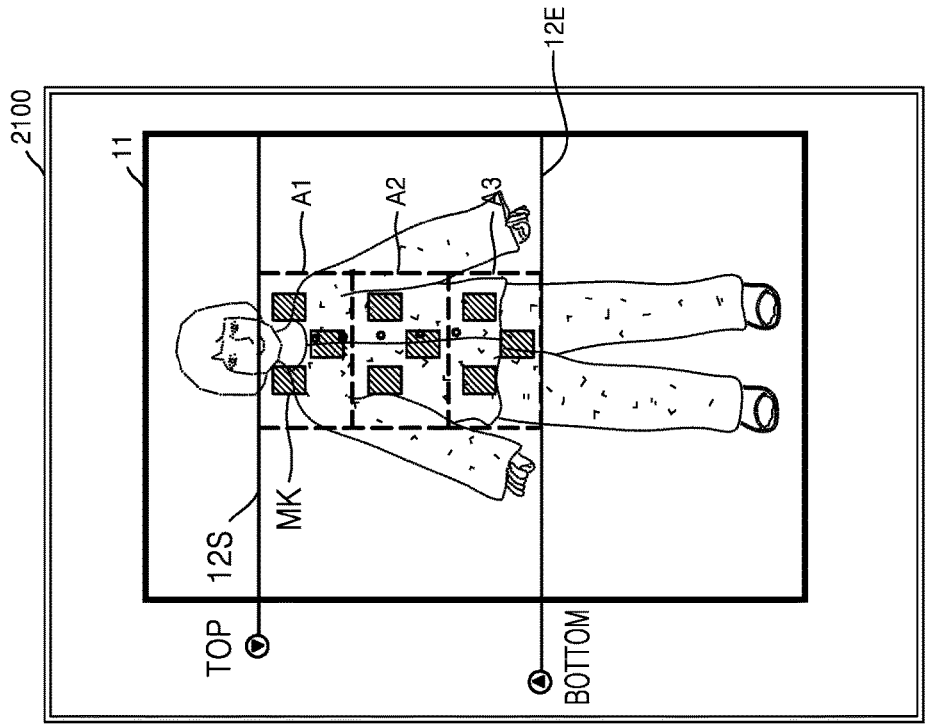

FIGS. 44A and 44B illustrate an example of a screen of an output unit 2100 on which AEC markers are displayed when the medical imaging apparatus 2000 of FIG. 9 is in a partial imaging mode. FIGS. 44A and 44B are basically the same as FIGS. 13A and 13B except for display of the AEC markers on the screen of the output unit 2100.

Referring to FIG. 44A, the output unit 2100 may display top and bottom indicators 12S and 12E and a plurality of guidelines 12-1, 12-2, 12-3, and 12-4 over an image 11 obtained by photographing an object. When positions of the top and bottom indicators 12S and 12E are adjusted by the user, the input unit 2300 may receive a user input for applying settings of the top and bottom indicators 12S and 12E via a UI 13.

When a user input for applying settings of the top and bottom indicators 12S and 12E is received, a screen of the output unit 2100 shown in FIG. 44A may change to a screen shown in FIG. 44B.

Referring to FIG. 44B, the output unit 2100 may display, over the image 11, regions A1, A2, and A3 for partial photographing operations obtained by partitioning an area to be X-rayed between the top and bottom indicators 12S and 12E whose settings have been applied. The output unit 2100 may further display a plurality of AEC markers MK on the regions A1, A2, and A3.

The AEC markers MK on the image 11 are displayed by visually associating a change in position of an AEC chamber due to movement of a detector with the object during partial photographing of the object. In particular, each of the AEC markers MK does not indicate a position of an AEC chamber relative to the object at a time point when the AEC marker MK is displayed, but rather a relationship between positions of the object and the AEC chamber during partial photographing of each of the regions A1, A2, and A3.

The controller 2200 may perform geometric registration of the image 11, thereby acquiring a position in the real-world that corresponds to each point in the image 11. Furthermore, the controller 2200 may acquire a position of an AEC chamber to be changed due to movement of the detector during partial photographing of the object. Thus, the controller 2200 may perform image processing whereby the AEC chamber is coordinated with the image 11, and an AEC marker MK that corresponds to the AEC chamber is superimposed onto the image 11.

The controller 2200 may set an on/off state of each of the AEC markers MK in each of the regions A1, A2, and A3 and turns on or off an AEC chamber in the detector which corresponds to each AEC marker MK according to the set on/off state of each AEC marker MK during a partial photographing operation.

The input unit 2300 may receive a user input for setting an on/off state of an AEC chamber. In detail, the input unit 2300 may receive a user input for setting an on/off state of an AEC marker selected from among the plurality of AEC markers MK displayed over the image 11.

Figure 45A:
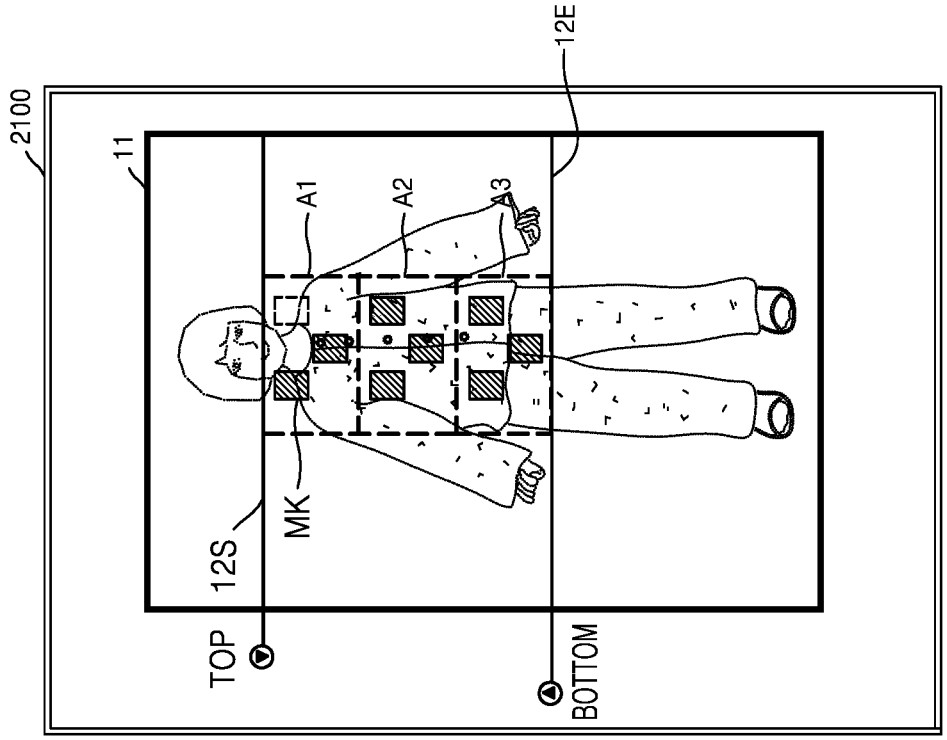
FIGS. 45A and 45B illustrate an example in which the medical imaging apparatus of FIG. 9 receives a user input for setting an on/off state of an AEC chamber when the medical imaging apparatus is in a partial imaging mode.
Figure 45B:
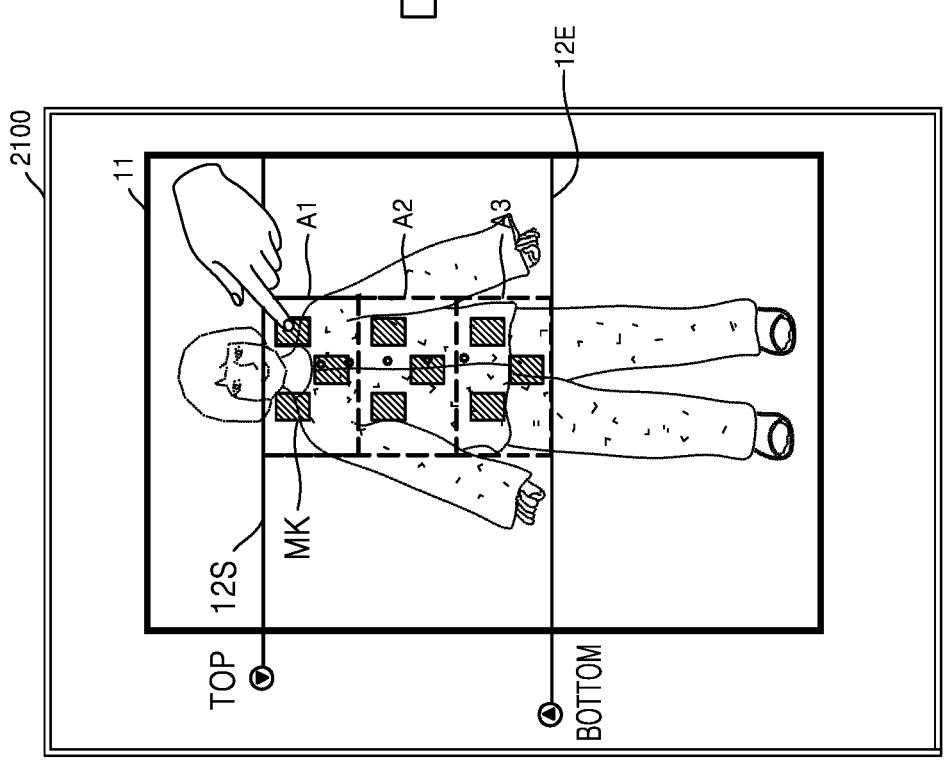

FIGS. 45A and 45B illustrate an example in which the medical imaging apparatus 2000 of FIG. 9 receives a user input for setting an on/off state of an AEC chamber when the medical imaging apparatus 2000 is in a partial imaging mode.

Referring to FIG. 45A, AEC markers MK, which are displayed on a screen of the output unit 2100, are all in an on-state. The user may select an AEC marker MK that he or she desires to turn off and turn off the selected AEC marker.

When the user selects an AEC marker MK by touching it, the screen of the output unit 2100 shown in FIG. 45A changes to a screen shown in FIG. 45B in which the selected AEC marker is displayed in an off-state.

The controller 2200 of the medical imaging apparatus 2000 may control an X-ray apparatus to perform partial photographing operations on first, second, and third regions A1, A2, and A3. During photographing of the first region A1, the medical imaging apparatus 2000 turns off an AEC chamber that corresponds to the turned-off AEC marker, among three AEC chambers of a detector. During photographing of the second and third regions A2 and A3, the medical imaging apparatus 2000 turns on all of the AEC chambers.

The output unit 2100 may further display a UI for setting on/off states of the AEC markers MK. FIGS. 46, 47, 48, 49, and 50 show examples of setting AEC markers MK via a UI.

Figure 46:
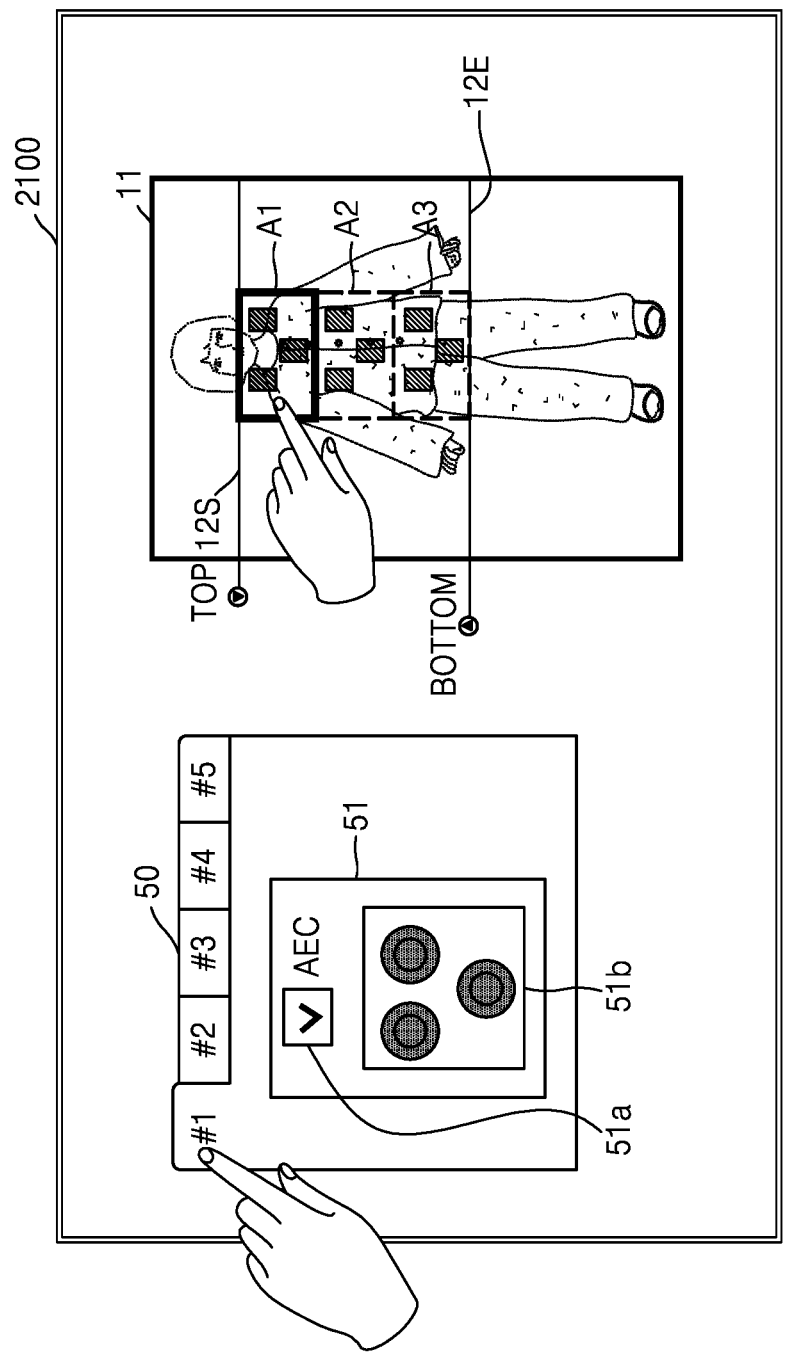
FIG. 46 illustrates an example in which the medical imaging apparatus of FIG. 9 receives a user input for selecting one of a plurality of regions for partial photographing.

FIG. 46 illustrates an example in which the medical imaging apparatus 2000 of FIG. 9 receives a user input for selecting one of a plurality of regions for partial photographing.

Referring to FIG. 46, the output unit 2100 may display AEC markers MK in first, second, and third regions A1, A2, and A3 for partial photographing operations, which are superimposed on an image 11 obtained by photographing an object. The output unit 2100 may further output a tab menu 50 that enables the user to select one of the first, second, and third regions A1, A2, and A3.

When a tab "#1" is selected from the tab menu 50, the first region A1 is selected. When a tab "#2" is selected from the tab menu 50, the second region A2 is selected. Although the tab menu 50 shown in FIG. 46 includes tabs "#1", "2", "3", "4", and "#5" as selectable regions, exemplary embodiments are not limited thereto.

When one of the first, second, and third regions A1, A2, and A3 is selected via the tab menu 50, the output unit 2100 may further display a UI 51 for setting on/off states of AEC markers MK displayed in the selected region. When the first region A1 is selected by selecting the tab "#1" from the tab menu 50 as shown in FIG. 46, the output unit 2100 may display the selected first region A1 in such a manner as to distinguish it from the other regions A2 and A3.

Alternatively, the user may directly select the first region A1 by touching or clicking the first region A1 displayed on the image 11. The input unit 2300 may receive a user input for touching or clicking the first region A1 excluding a portion where the AEC markers MK are displayed in the image 11. The output unit 2100 may display the first region A1 selected according to the user input in such a manner as to distinguish the selected first region A1 from the other regions A2 and A3. Furthermore, the output unit 2100 may display a selection of the tab "#1" corresponding to the first region A1 from the tab menu 50.

The output unit 2100 may further display, below the tab "#1" selected from the tab menu 50, a UI 51 that includes a first UI 51a for turning off all AEC markers in the first region A1 at once and a second UI 51b for separately turning on or off each of the AEC markers.

Figure 47:
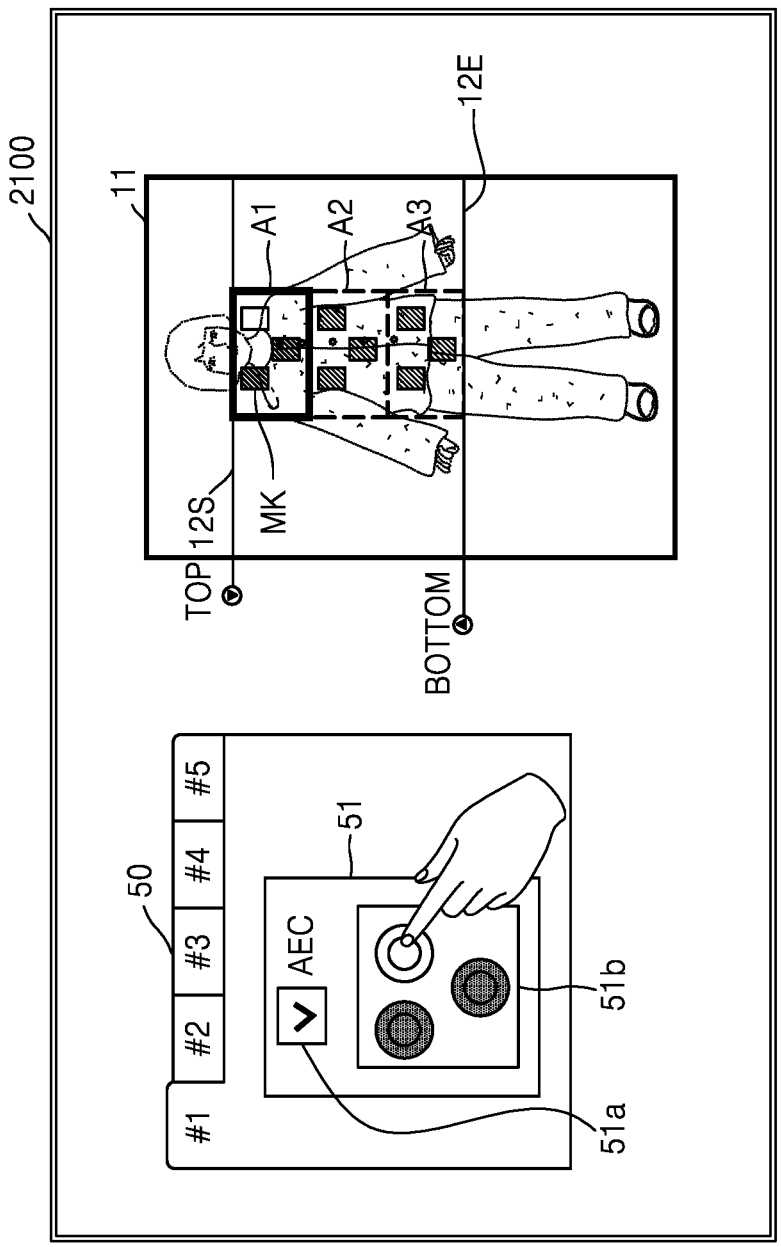
FIG. 47 is an example in which a user selects an AEC marker from among AEC markers displayed in a first region after selecting the first region, and then sets an on/off state of the selected AEC marker.

FIG. 47 is an example in which a user selects an AEC marker from among AEC markers displayed in a first region A1 after selecting the first region, and then sets an on/off state of the selected AEC marker.

Referring to FIG. 47, the user may turn off an AEC marker that he or she desires to turn off among the AEC markers displayed in the first region A1 by selecting an icon that corresponds to the AEC marker via a second UI 51b.

Figure 48:
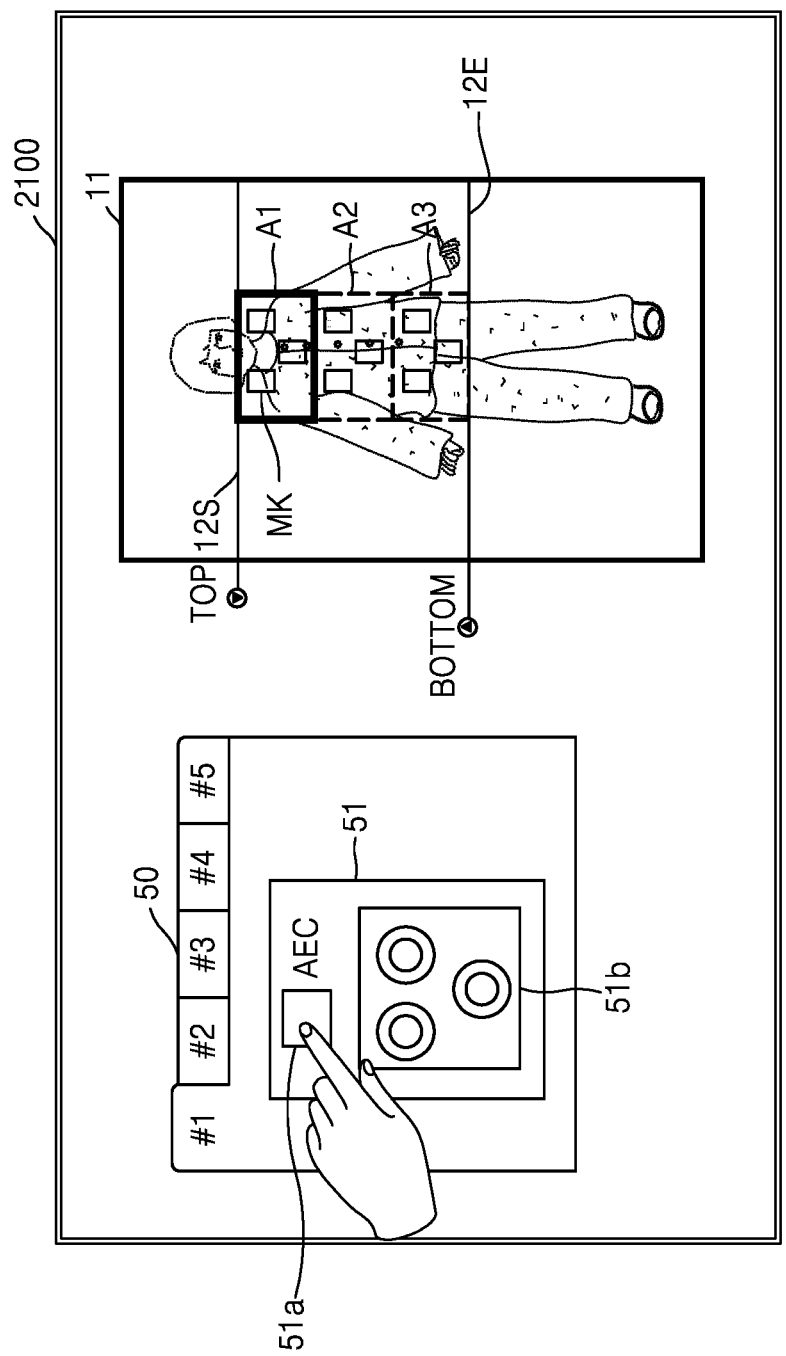
FIG. 48 is an example in which the user turns off all AEC markers via a first user interface (UI) after selecting a first region.

FIG. 48 is an example in which a user turns off all AEC markers via a first UI 51a after selecting the first region A1.

Referring to FIG. 48, if the user desires to turn off all AEC markers MK displayed on an image 11, the user may do so by selecting the first UI 51a via a touch or click.

When the input unit 2300 receives a user input for selecting the first UI 51a, the controller 2200 may turn off all of the AEC markers MK displayed on the image 11. Furthermore, the controller 2200 may control the output unit 2100 to display all of the AEC markers in an off-state. In addition, the output unit 2100 may display all of icons included in a UI 51 in an off-state.

Figure 49:
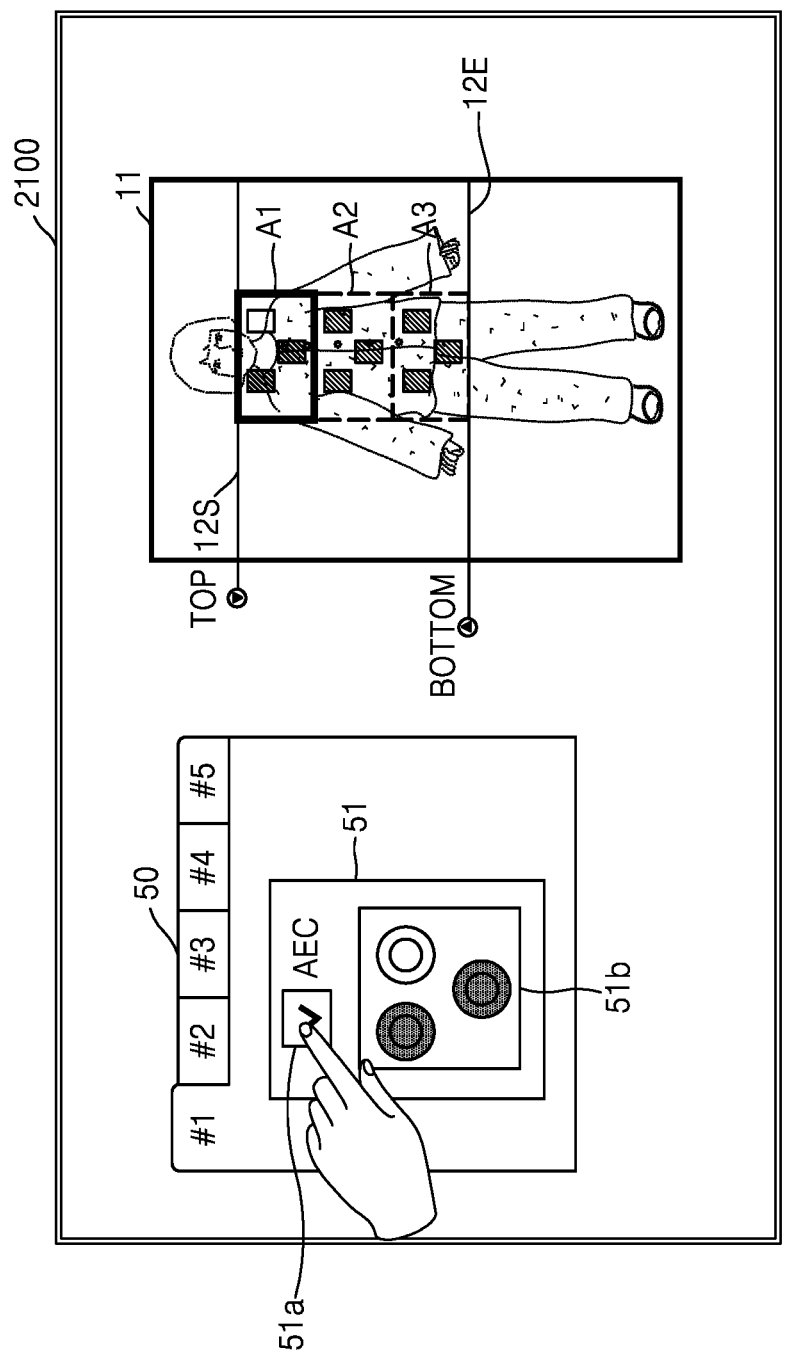
FIG. 49 illustrates an example of returning on/off states of AEC markers to their original states before being changed to an off state via a first UI after turning off all the AEC markers via the first UI as shown in FIG. 48.

FIG. 49 illustrates an example of returning on/off states of AEC markers to their original states before being changed to an off state via a first UI 51a after turning off all the AEC markers via the first UI 51a as shown in FIG. 48.

Referring to FIG. 49, after AEC markers are all turned off, when the user selects the first UI 51a again, on/off states of the AEC markers may be returned to respective states that existed before being turned off.

In detail, when the input unit 2300 receives a user input for selecting the first UI 51a, the controller 2200 may return on/off states of AEC markers displayed on the image 11 to their original states before the AEC markers are all turned off. Furthermore, the controller 2200 may control the output unit 2100 to display all the AEC markers in their original on/off states. The output unit 2100 may also display icons included in a UI 51 in their original on/off states.

Figure 50:
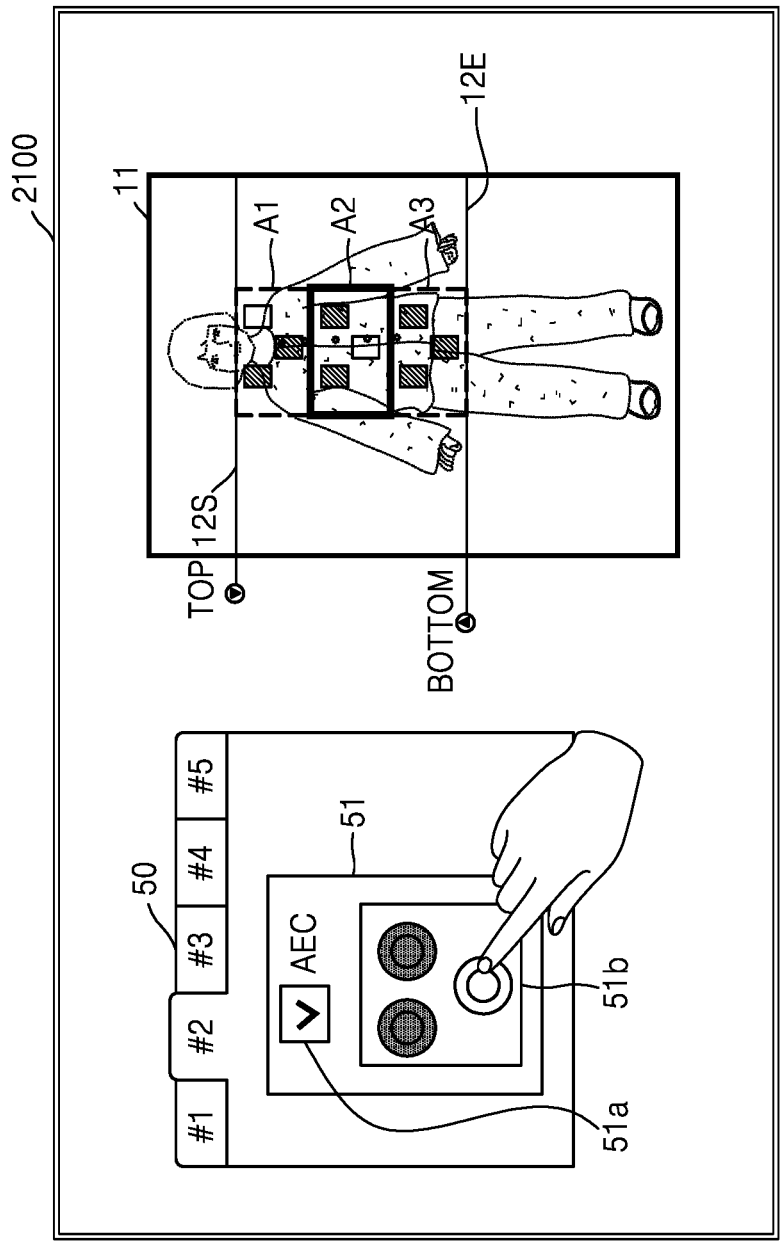
FIG. 50 is an example in which a user selects an AEC marker from among AEC markers displayed in a second region after selecting the second region, and then sets an on/off state of the selected AEC marker.

FIG. 50 is an example in which a user selects an AEC marker from among AEC markers displayed in a second region A2 after selecting the second region A2, and then sets an on/off state of the selected AEC marker.

Referring to FIG. 50, the user may select the second region A2 by selecting a tab "#2" from the tab menu 50. The output unit 2100 may display a UI 51 for setting on/off states of the AEC markers in the second region A2 below the tab "#2" selected from the tab menu 50.

The user may turn off an AEC marker which the user desires to turn off among the AEC markers in the second region A2 by selecting an icon that corresponds to the AEC marker via a second UI 51b.

The output unit 2100 may further display another UI or pieces of information necessary for X-ray imaging, as well as the UI 51 for setting on/off states of AEC markers below a tab selected from the tab menu 50.

Figure 51:
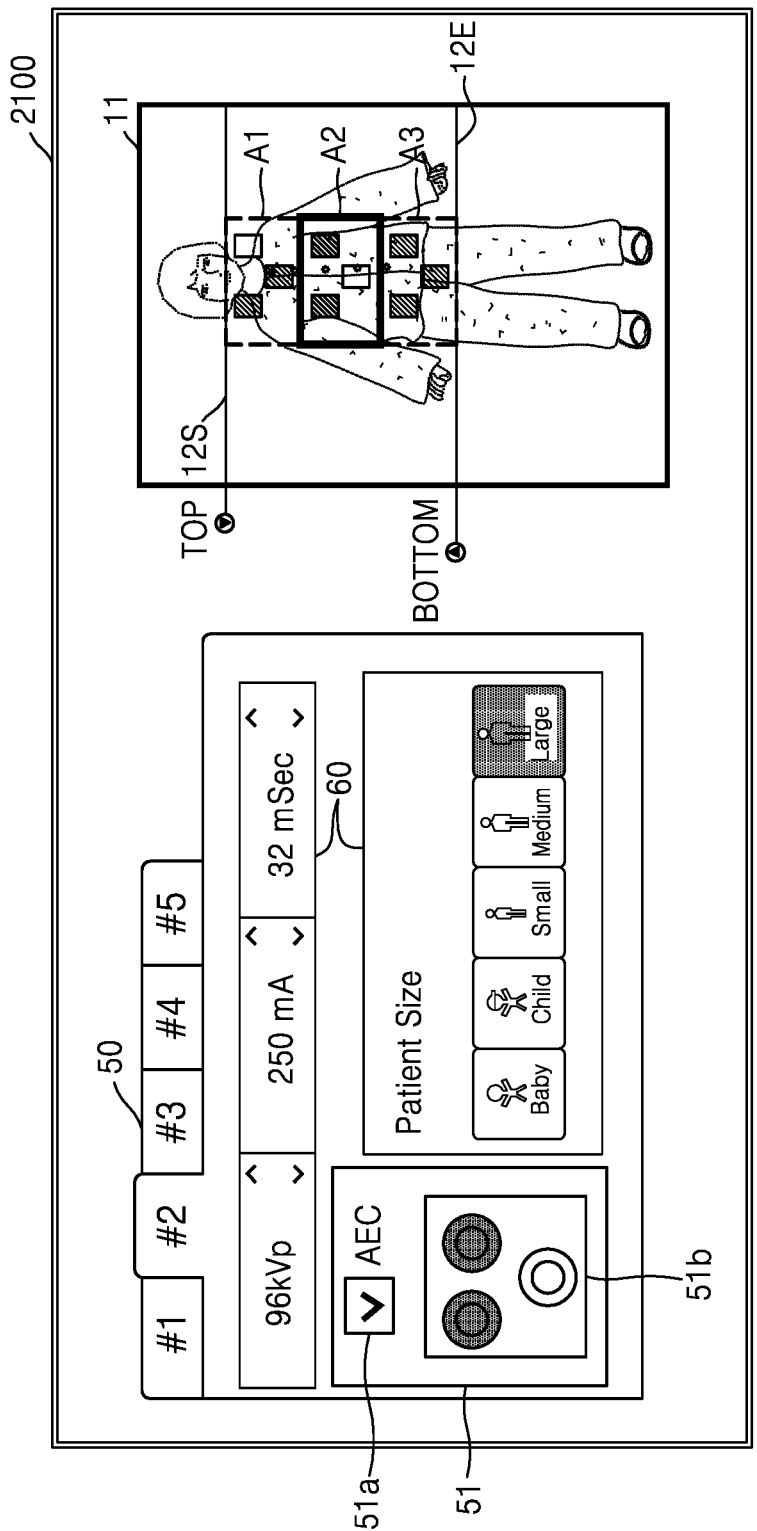
FIG. 51 is an example of an output unit of a medical imaging apparatus, according to an exemplary embodiment.

FIG. 51 is an example of the output unit 2100 of the medical imaging apparatus 2000, according to an exemplary embodiment.

Referring to FIG. 51, the user may select a second region A2 by selecting a tab "#2" from the tab menu 50. Below the selected tab "#2", the output unit 2100 may further display a UI 60 that enables the user to set conditions for irradiation of the second region A2 by an X-ray source or a size of the object, as well as a UI 51 for setting on/off states of AEC markers in the second region A2. However, FIG. 51 is merely an example, and a screen displayed by the output unit 2100 is not limited thereto.

After the on/off states of the AEC markers are set as shown in FIG. 51, the controller 2200 of the medical imaging apparatus 2000 may control an X-ray apparatus to perform partial photographing operations on first, second, and third regions A1, A2, and A3, respectively. During photographing of the first region A1, the medical imaging apparatus 2000 turns off a rightmost AEC chamber among three AEC chambers of a detector. During photographing of the second region A2, the medical imaging apparatus 2000 turns off an AEC chamber disposed below leftmost and rightmost AEC chambers among the three AEC chambers. During photographing of the third region A3, the medical imaging apparatus 2000 turns on all of the three AEC chambers of the detector.

Figure 52A:
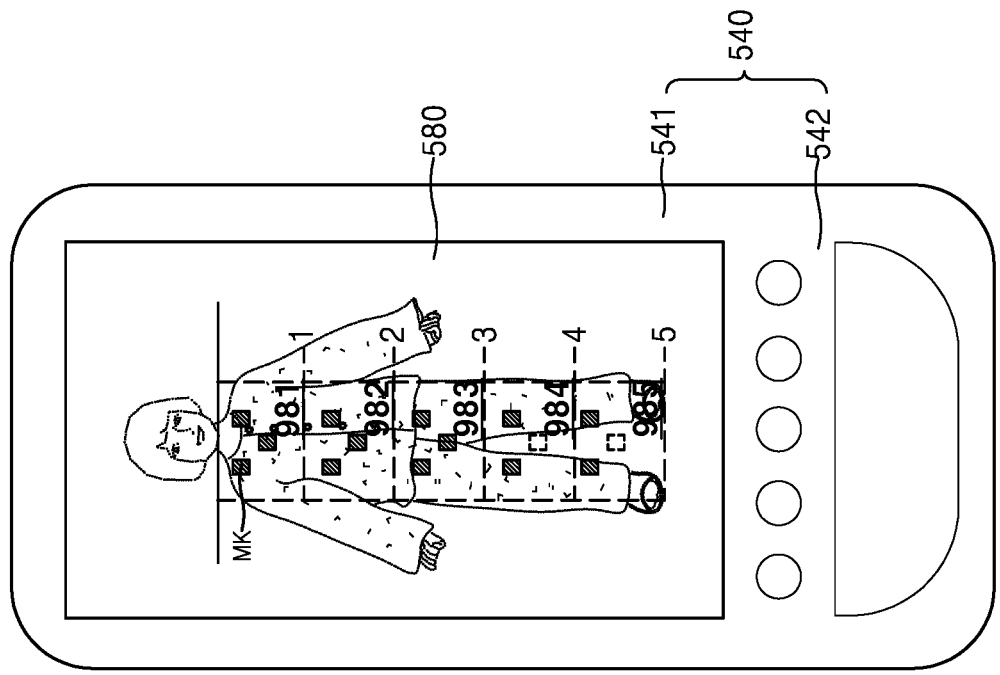
FIGS. 52A and 52B illustrate an example of an output unit of an X-ray apparatus when the X-ray apparatus is in a partial imaging mode.
Figure 52B:
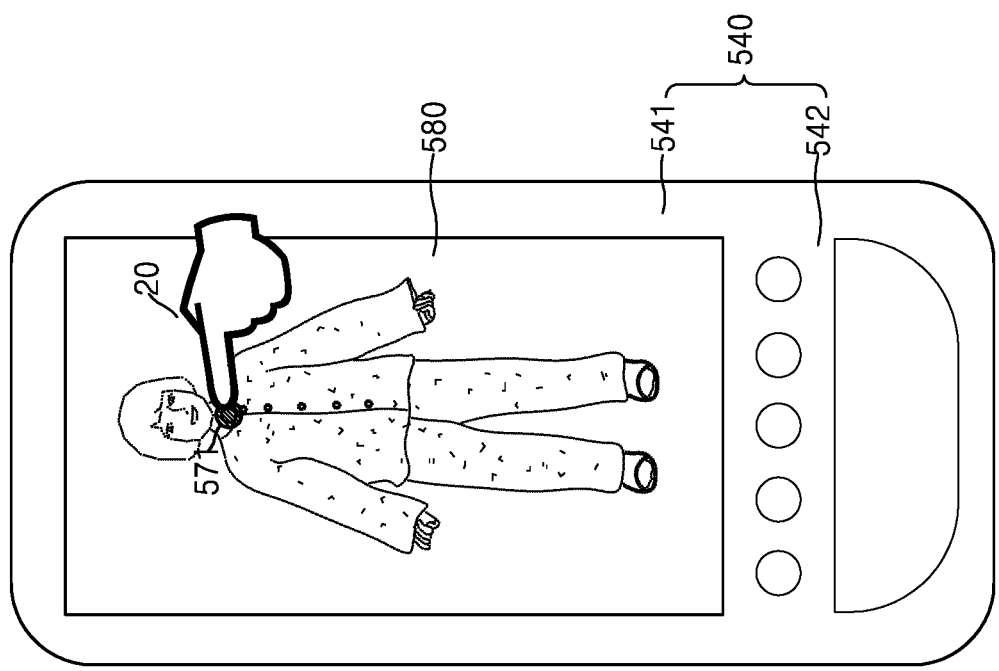

FIGS. 52A and 52B illustrate an example of the output unit 541 of an X-ray apparatus the X-ray apparatus 500 of FIG. 18 when the X-ray apparatus 500 is in a partial imaging mode.

Referring to FIG. 52A, the output unit 541 of the X-ray apparatus 500 may display an image 580 obtained by photographing an object. An input unit 542 may receive a user input for setting a top limit 571 for an area to be X-rayed. When the user input is received, a screen of the output unit 541 shown in FIG. 52A changes to a screen shown in FIG. 52B. The output unit 541 may display a top indicator for setting the top limit 571 for the area to be X-rayed and a plurality of guidelines. Furthermore, the output unit 541 may display AEC markers MK in each of regions delineated by the top indicator and the plurality of guidelines.

The output unit 541 may further display an on/off state of each of the AEC markers MK. An AEC marker MK that is located outside the object on the image 580 may be displayed as a dashed line, which indicates that the AEC marker MK is in an off-state. The X-ray apparatus 500 may detect an AEC marker MK that is located outside the object and turns off the detected AEC marker MK. The user may additionally select an on/off state of each of the AEC markers MK.

The input unit 542 may receive a user input for setting a bottom limit for an area to be X-rayed. Descriptions of operations of the X-ray apparatus 500 are the same as the above descriptions with respect to those of the X-ray apparatus 500, and thus, are not repeated.

The screen of the output unit 541 of the X-ray apparatus 500 of FIGS. 52A and 52B may also be applied to the output unit 2100 of the medical imaging apparatus 2000 or an output unit of a workstation.

Figure 53:
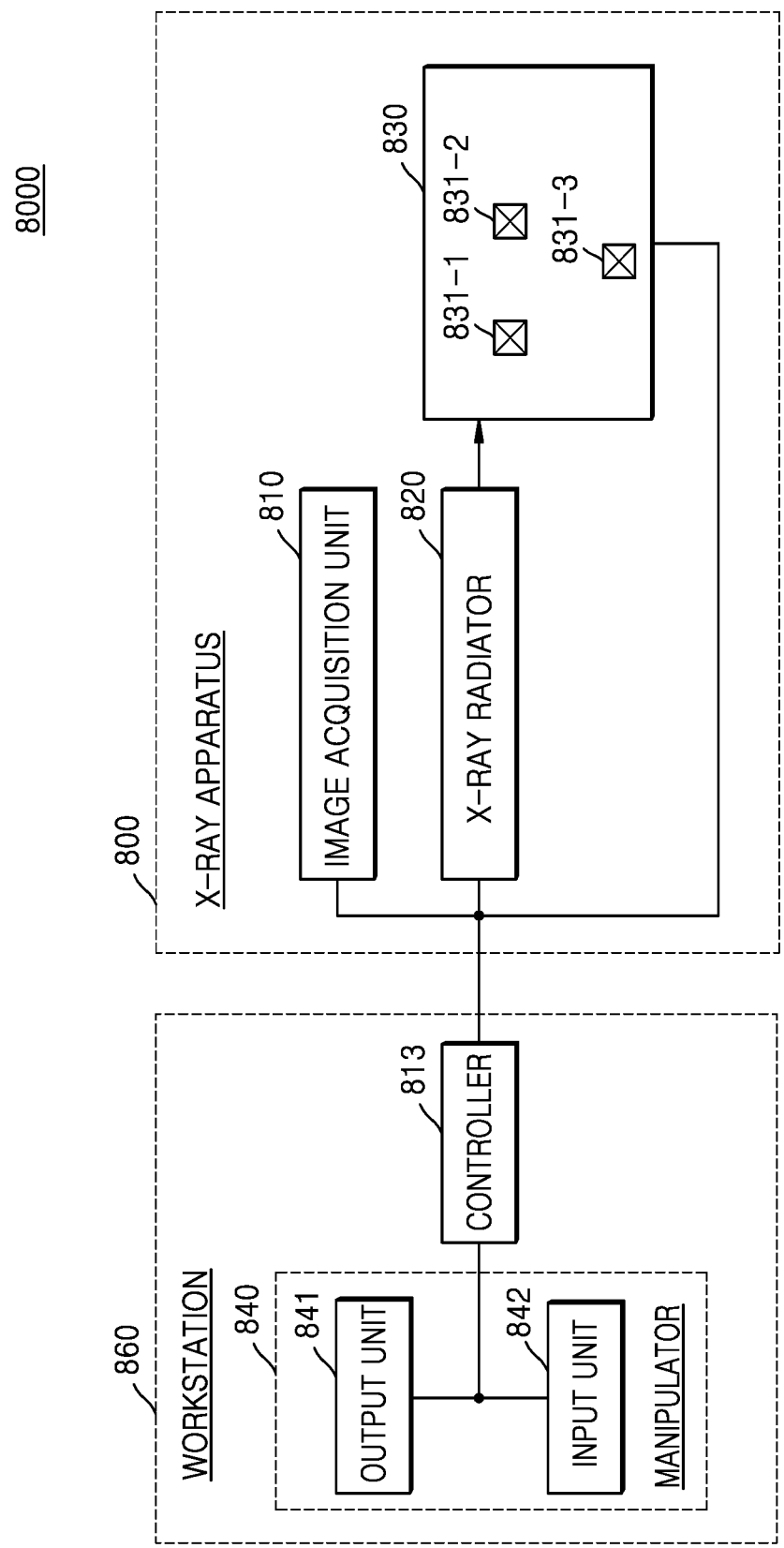
FIG. 53 is a block diagram of an X-ray system, according to an exemplary embodiment.

FIG. 53 is a block diagram of an X-ray system 8000, according to an exemplary embodiment.

Referring to FIG. 53, the X-ray system according to the present exemplary embodiment includes an X-ray apparatus 800 and a workstation 860.

The X-ray apparatus 800 includes an image acquisition unit 810 and an X-ray radiator 820. The X-ray apparatus 800 may further include a detector 830 which includes at least one AEC chamber 831-1, 831-2, and 831-3. The above descriptions of the X-ray apparatuses 100, 200, 300, 500 and 600 may be applied to the X-ray apparatus 800. Although not shown in FIG. 53, as described above, the X-ray apparatus 800 may further include a manipulator and/or a controller.

The workstation 860 may include a manipulator 840 for providing a UI. The workstation 860 may further include a controller 813.

The manipulator 841 may include an output unit 841 and an input unit 842. The above descriptions with respect to the medical imaging apparatus 2000 may all be applied to the workstation 860. The UI provided by the manipulator 841 may be the same as a UI that is used in the manipulator of the X-ray apparatus 800. Thus, a simple and intuitive UI may be provided, which enables the user to intuitively and conveniently manipulate or control the X-ray apparatus 800.

The image acquisition unit 810 of the X-ray apparatus 800 may acquire an image of an object by photographing the object.

The workstation 860 may receive the image of the object via a communication unit (not shown). When the X-ray apparatus 800 is in a partial imaging mode, the output unit 841 of the workstation 860 may display a top indicator and at least one guideline over an image. The output unit 841 may further display AEC markers. For example, if the X-ray apparatus 800 is in a single imaging mode, the output unit 841 may display AEC markers over the image. The above descriptions with respect to the output unit 2100 of the medical imaging apparatus 2000 may all be applied to the output unit 841, and thus, are not repeated.

The input unit 842 may receive a user input for adjusting a position of the top indicator on the image. The input unit 842 may also receive a user input for setting a bottom limit for an area to be X-rayed on the image.

Figure 54:
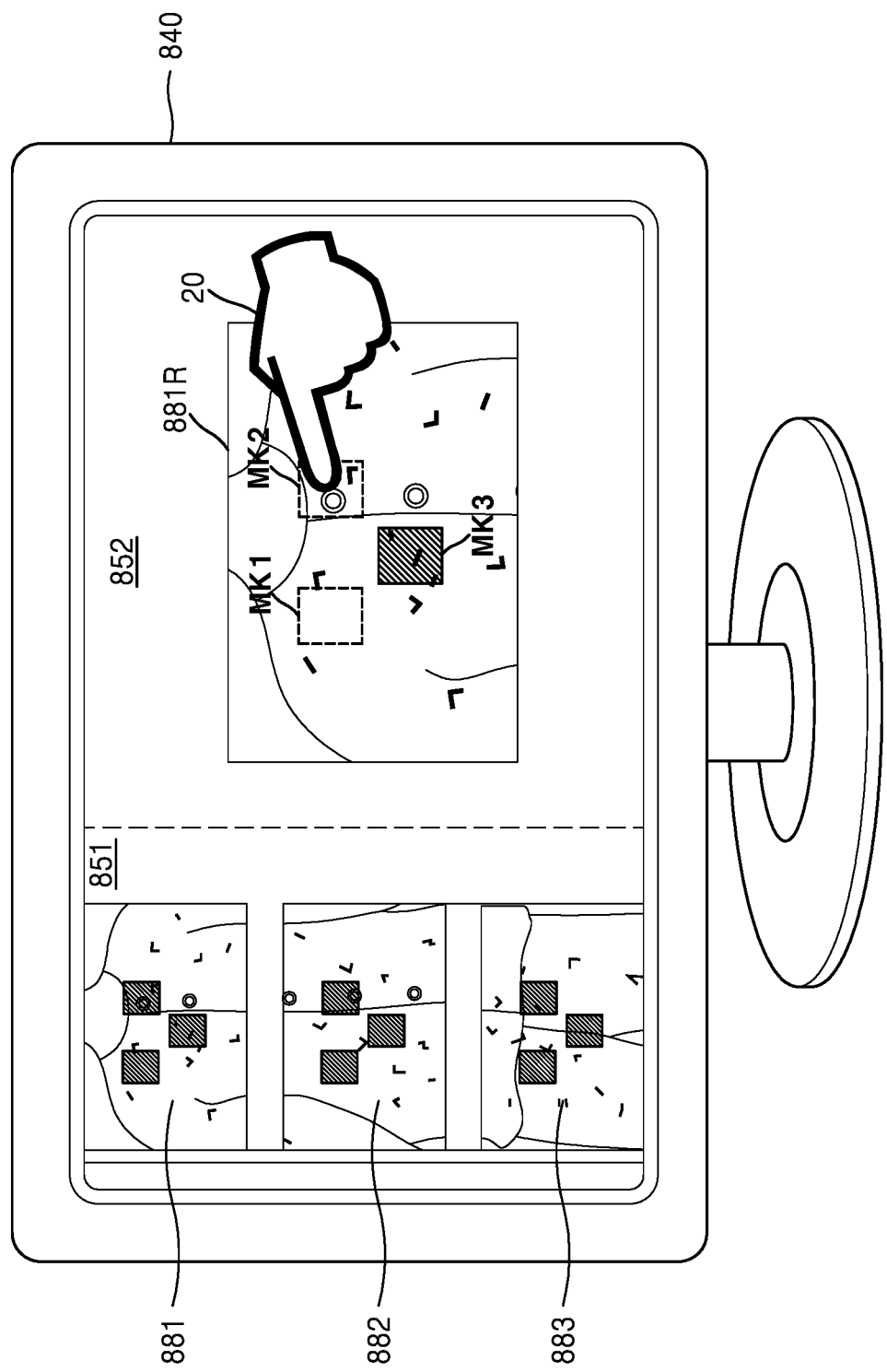
FIG. 54 is an example of a manipulator of a workstation when an X-ray system is in a partial imaging mode.

FIG. 54 is an example of a manipulator 840 of a workstation when an X-ray system is in a partial imaging mode.

FIG. 54 shows an example of the manipulator 840 when the number of partial photographing operations to be performed on an area set by the user to be X-rayed is determined as three (3). For example, the number of partial photographing operations may be determined as three (3) via the process described with reference to FIG. 44A. In this case, the screen shown in FIG. 44A may change to a screen shown in FIG. 54 and not to the screen shown in FIG. 44B.

Referring to FIG. 54, the manipulator 840 may include an input unit and output unit implemented together. The input unit may include a touch screen, and the touch screen may be formed in the output unit.

A screen of the manipulator 840 may include first and second screens 851 and 852. Regions 881, 882, and 883 are created by partitioning the area to be X-rayed in an image obtained by photographing an object according to the number of partial photographing operations and may be displayed on the first screen 851. AEC markers may also be displayed together in each of the regions 881, 882, and 883. The regions 881, 882, and 883 may respectively correspond to the regions A1, A2, and A3 shown in FIG. 44B.

The region 881 selected from among the regions 881, 882, and 883 on the first screen 851 may be displayed on the second screen 852 as an enlarged version 881R of an image. The regions 881, 882, and 883 may be sequentially enlarged to be displayed on the second screen 852, or a region selected by a user 20 may be enlarged to be displayed thereon.

AEC markers MK1, MK2, and MK3 may be displayed over the enlarged version 881R of an image. The user 20 may select a desired AEC marker MK2 whose on/off state is to be set from among the AEC markers MK1, MK2, and MK3 and set the on/off state of the selected AEC marker MK2

Although FIG. 54 shows that the manipulator 840 is a manipulator of a workstation, it will be apparent to those of ordinary skill in the art that a method of displaying a screen of the manipulator 840 may also be applied to a screen of a manipulator of an X-ray apparatus.

Figure 55:
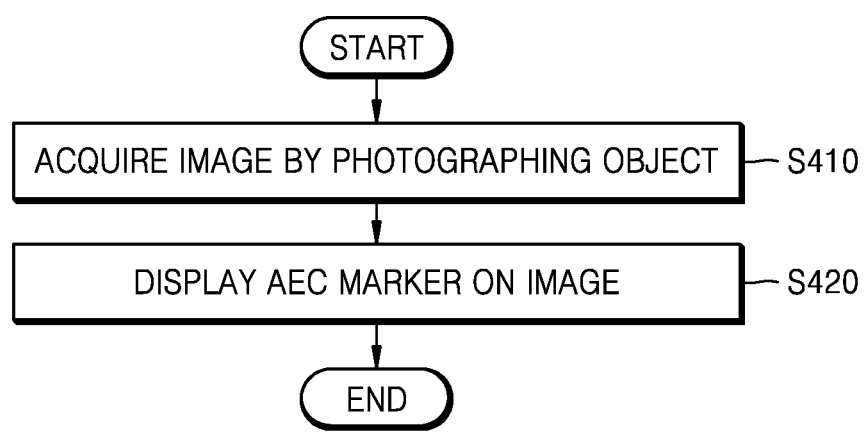
FIG. 55 is a flowchart of a method for operating a medical imaging apparatus, according to an exemplary embodiment.

FIG. 55 is a flowchart of a method for operating a medical imaging apparatus, according to an exemplary embodiment.

Referring to FIG. 55, in operation S410, the medical imaging apparatus acquires an image of an object. In operation S420, the medical imaging apparatus also displays a plurality of AEC markers over the image of the object.

The medical imaging apparatus may set an on/off state of each of the plurality of AEC markers and turn on or off an AEC chamber included in an X-ray detector, which corresponds to each AEC marker, according to a set on/off state of each AEC marker. The medical imaging apparatus may receive a user input for setting an on/off state of an AEC marker selected from among the plurality of AEC markers. The medical imaging apparatus may detect an AEC marker that is located outside the object among the plurality of AEC markers and turn off the detected AEC marker.

The medical imaging apparatus may further display a collimation area that corresponds to an X-ray irradiation region over the image. The medical imaging apparatus may also receive a user input for adjusting the collimation area on the image. The medical imaging apparatus may adjust a collimator included in an X-ray radiator according to the adjusted collimation area.

The medical imaging apparatus may receive a user input that relates to an instruction for turning on of a lamp of the collimator. The medical imaging apparatus may display a plurality of AEC markers over an image obtained by photographing an object when the lamp of the collimator is turned on.

The above descriptions with respect to previously described figures will be applied to the method for operating the medical imaging apparatus.

The exemplary embodiments can be recorded in programs that can be executed on a computer and be implemented through general purpose digital computers which can run the programs using a computer-readable recording medium.

Examples of the computer-readable recording medium include magnetic storage media (e.g., ROM, floppy disks, hard disks, etc.), optical recording media (e.g., CD-ROMs, or DVDs), etc.), and transmission media such as Internet transmission media.

While one or more exemplary embodiments have been described with reference to the figures, it will be understood by those of ordinary skill in the art that various changes in form and details may be made therein without departing from essential features and the spirit and scope as defined by the following claims.

What is claimed is:

1. A medical imaging apparatus comprising:
   a display device;
   a camera configured to obtain an image of an object by photographing the object; and
   a controller configured to:
   control the display device to display, in a first region of a screen of the display device, the image and a plurality of Automatic Exposure Control (AEC) markers that respectively indicate positions of a plurality of AEC chambers on the image, and
   control the display device to display, in a second region of the screen, a user interface (UI) for setting on/off states of the plurality of AEC markers while the image and the plurality of AEC markers are displayed in the first region of the screen,
   wherein the UI includes a plurality of icons corresponding to the plurality of AEC markers.

2. The medical imaging apparatus of claim 1, further comprising an input device configured to receive a user input for selecting at least one icon from among the displayed plurality of icons,
wherein the controller is further configured to:
set an on/off state of each of at least one AEC marker from among the plurality of AEC markers corresponding to the selected at least one icon by the user input, and
turn on or off each of at least one respective AEC chamber based on the set on/off state of the each of the at least one AEC marker.

3. The medical imaging apparatus of claim 2, wherein the controller is further configured to control the display device to display a state of each of the at least one icon corresponding to the on/off state of the each of the at least one AEC marker.

4. The medical imaging apparatus of claim 1, wherein the controller is further configured to:
detect, from among the plurality of AEC markers displayed on the image, an AEC marker which is located outside the object, and
control the display device to display a turn off state of an AEC chamber corresponding to the detected AEC marker.

5. The medical imaging apparatus of claim 1, wherein the display device is further configured to display, on the image, a collimation area that corresponds to a region to be irradiated with X-rays radiated by an X-ray radiator.

6. The medical imaging apparatus of claim 5, further comprising an input device configured to receive a user input that relates to adjusting the collimation area on the image.

7. The medical imaging apparatus of claim 6, wherein the controller is further configured to adjust a collimator included in the X-ray radiator based on the adjusted collimation area.

8. The medical imaging apparatus of claim 1, further comprising an input device configured to receive a user input that relates to an instruction for turning on of a lamp of a collimator,
wherein the display device is further configured to display the plurality of AEC markers on the image that is obtained by photographing the object when the lamp of the collimator is turned on.

9. The medical imaging apparatus of claim 1, further comprising an input device configured to receive a user input for selecting at least one AEC marker from among the plurality of AEC markers displayed on the image, and setting an on/off state of each of the selected at least one AEC marker.

10. The medical imaging apparatus of claim 1, wherein the controller is further configured to:
control the display device to display, on the image, a top indicator that relates to setting a top limit for an area to be X-rayed and a bottom indicator that relates to setting a bottom limit for the area,
divide an area between the top indicator and the bottom limit in the image into a plurality of regions for partial photographing operations based on a number of the partial photographing operations, and
control the display device to display the plurality of AEC markers in each of the plurality of regions for the partial photographing operations displayed on the image.

11. The medical imaging apparatus of claim 10, wherein the controller is further configured to:
set an on/off state of each of the plurality of AEC markers, and
turn on or off each of the respective plurality of AEC chambers based on the set on/off state of the each of the plurality of AEC markers during the partial photographing operations.

12. The medical imaging apparatus of claim 10, further comprising an input device configured to receive a user input for selecting a region from among the plurality of regions for the partial photographing operations,
wherein the controller is further configured to:
control the display device to display a tab menu user interface including a plurality of tab menus corresponding to each of the plurality of regions,
select a region from among the plurality of regions based on the user input received by the input device, and
control the display device to display AEC markers displayed on a first tab corresponding to the selected region.

13. The medical imaging apparatus of claim 10, wherein the controller is further configured to control the display device to display a tab menu user interface including a plurality of tab menus corresponding to each of the plurality of regions,
the medical imaging apparatus further comprises an input device configured to receive a user input for selecting a tab menu from among the plurality of tab menus, and
wherein the controller is further configured to:
select a first tab from among the plurality of tab menus based on the received user input received by the input device,
select a region from among the plurality of regions for the partial photographing operations corresponding to the selected first tab, and
control the display device to display user interfaces for setting on/off states of AEC markers displayed on the region.

14. A method for operating a medical imaging apparatus, the method comprising:
obtaining an image obtained by photographing an object;
displaying, in a first region of a screen of a display device of the medical imaging apparatus, the image and a plurality of Automatic Exposure Control (AEC) markers that respectively indicate positions of a plurality of AEC chambers on the image; and
displaying, in a second region of the screen, a user interface (UI) for setting on/off states of the plurality of AEC markers while the image and the plurality of AEC markers are displayed in the first region of the screen,
wherein the UI includes a plurality of icons corresponding to the plurality of AEC markers.

15. The method of claim 14, further comprising:
receiving a user input for selecting at least one icon from among the displayed plurality of icons;
setting an on/off state of each of at least one AEC marker from among the plurality of AEC markers corresponding to the selected at least one icon by the user input; and
turning on or off each of at least one respective AEC chamber based on the set on/off state of the each of the at least one AEC marker.

16. The method of claim 15, further comprising displaying a state of each of the at least one icon corresponding to the on/off state of the each of the at least one AEC marker.

17. The method of claim 14, further comprising displaying, on the image, a collimation area that corresponds to a region to be irradiated with X-rays radiated by an X-ray radiator.

18. The method of claim 17, further comprising receiving a user input that relates to adjusting the collimation area on the image.

19. The method of claim 18, further comprising adjusting a collimator included in the X-ray radiator based on the adjusted collimation area.

20. The method of claim 14, further comprising:
receiving a user input that relates to an instruction for turning on of a lamp of a collimator; and
displaying the plurality of AEC markers on the image that is obtained by photographing the object when the lamp of the collimator is turned on.

21. The method of claim 14, further comprising:
displaying, on the image, a top indicator that relates to setting a top limit for an area to be X-rayed and a bottom indicator that relates to setting a bottom limit for the area;
dividing an area between the top indicator and the bottom limit in the image into a plurality of regions for partial photographing operations based on a number of the partial photographing operations; and
displaying the plurality of AEC markers in each of the plurality of regions for the partial photographing operations on the image.

22. The method of claim 21, further comprising:
setting an on/off state of each of the plurality of AEC markers; and
turning on or off each of the respective plurality of AEC chambers based on the set on/off state of the each of the plurality of AEC markers during the partial photographing operations.

23. The method of claim 21, further comprising:
displaying a tab menu user interface including a plurality of tab menus corresponding to each of the plurality of regions for the partial photographing operations;
receiving a user input for selecting a region from among the plurality of regions;
selecting the region from among the plurality of regions based on the user input; and
displaying AEC markers displayed on a first tab corresponding to the selected region.

24. The method of claim 21, further comprising:
displaying a tab menu user interface including a plurality of tab menus corresponding to each of the plurality of regions;
receiving a user input for selecting a tab menu from among the plurality of tab menus;
selecting a first tab from among the plurality of tab menus based on the received user input;
selecting a region from among the plurality of regions for the partial photographing operations corresponding to the selected first tab; and
displaying user interfaces for setting on/off state of AEC markers displayed on the region.

* * * * *